United States Patent
Palm et al.

(10) Patent No.: US 12,226,451 B2
(45) Date of Patent: *Feb. 18, 2025

(54) FGF-21 FORMULATIONS

(71) Applicant: Bristol-Myers Squibb Company, Princeton, NJ (US)

(72) Inventors: Thomas Palm, Helmetta, NJ (US); Mehrnaz Khossravi, West Windsor, NJ (US); Sanket Patke, Belmont, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1039 days.

This patent is subject to a terminal disclaimer.

(21) Appl. No.: 17/257,530

(22) PCT Filed: Jul. 2, 2019

(86) PCT No.: PCT/US2019/040356
§ 371 (c)(1),
(2) Date: Dec. 31, 2020

(87) PCT Pub. No.: WO2020/010117
PCT Pub. Date: Jan. 9, 2020

(65) Prior Publication Data
US 2021/0260161 A1    Aug. 26, 2021

Related U.S. Application Data

(60) Provisional application No. 62/693,847, filed on Jul. 3, 2018.

(51) Int. Cl.
| | | |
|---|---|---|
| *A61K 38/18* | (2006.01) | |
| *A61K 9/00* | (2006.01) | |
| *A61K 9/08* | (2006.01) | |
| *A61K 47/22* | (2006.01) | |
| *A61K 47/26* | (2006.01) | |
| *A61K 47/54* | (2017.01) | |
| *A61K 47/60* | (2017.01) | |
| *A61K 47/64* | (2017.01) | |
| *A61K 47/68* | (2017.01) | |

(52) U.S. Cl.
CPC ........ *A61K 38/1825* (2013.01); *A61K 9/0019* (2013.01); *A61K 9/08* (2013.01); *A61K 47/22* (2013.01); *A61K 47/26* (2013.01); *A61K 47/542* (2017.08); *A61K 47/547* (2017.08); *A61K 47/60* (2017.08); *A61K 47/64* (2017.08); *A61K 47/6811* (2017.08)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,683,195 A | 7/1987 | Mullis et al. |
| 4,683,202 A | 7/1987 | Mullis |
| 4,800,159 A | 1/1989 | Mullis et al. |
| 4,904,584 A | 2/1990 | Shaw |
| 4,965,188 A | 10/1990 | Mullis et al. |
| 5,218,092 A | 6/1993 | Sasaki et al. |
| 5,252,714 A | 10/1993 | Harris et al. |
| 5,643,575 A | 7/1997 | Martinez et al. |
| 5,648,260 A | 7/1997 | Winter et al. |
| 5,658,570 A | 8/1997 | Newman et al. |
| 5,739,277 A | 4/1998 | Presta et al. |
| 5,834,250 A | 11/1998 | Wells et al. |
| 5,846,951 A | 12/1998 | Gregoriadis |
| 5,869,046 A | 2/1999 | Presta et al. |
| 6,030,613 A | 2/2000 | Blumberg et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,242,195 B1 | 6/2001 | Idusogie et al. |
| 6,277,375 B1 | 8/2001 | Ward |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,716,626 B1 | 4/2004 | Itoh et al. |
| 6,737,056 B1 | 5/2004 | Presta |

(Continued)

FOREIGN PATENT DOCUMENTS

| | | |
|---|---|---|
| WO | WO-8807089 A1 | 9/1988 |
| WO | WO-9614339 A1 | 5/1996 |

(Continued)

OTHER PUBLICATIONS

Kamerzell et al., Advanced Drug Delivery Reviews 63: 1118-1159 (Year: 2011).*
Armour, K.L., et al., "Recombinant Human IgG Molecules Lacking Fc gamma Receptor I Binding and Monocyte Triggering Activities," European Journal of Immunology 29(8):2613-2624, Wiley-VCH, Germany (Aug. 1999).
Arnau, J., et al., "Current Strategies for the use of Affinity Tags and Tag Removal for the Purification of Recombinant Proteins," Protein Expression and Purification 48(1):1-13, Elsevier Inc., United States (Jul. 2006).

(Continued)

*Primary Examiner* — Phuong Huynh
(74) *Attorney, Agent, or Firm* — Sterne, Kessler, Goldstein & Fox P.L.L.C.

(57) ABSTRACT

The present application provides pharmaceutical formulations comprising a FGF-21 polypeptide, e.g., a modified FGF-21 polypeptide such as PEG-FGF-21, and one or more stabilizers such as the chelator DPTA. The formulations can be can further stabilized by including a surfactant such as polysorbate 80 and/or adjusting the pH to about 7.1. Also provided are methods of manufacture, methods of treatment, and kits.

4 Claims, 9 Drawing Sheets

Specification includes a Sequence Listing.

(56) References Cited

U.S. PATENT DOCUMENTS

| | | |
|---|---|---|
| 6,821,505 B2 | 11/2004 | Ward |
| 6,998,253 B1 | 2/2006 | Presta et al. |
| 7,083,784 B2 | 8/2006 | Dall'Acqua et al. |
| 7,317,091 B2 | 1/2008 | Lazar et al. |
| 7,348,004 B2 | 3/2008 | Peters et al. |
| 7,404,956 B2 | 7/2008 | Peters et al. |
| 7,862,820 B2 | 1/2011 | Peters et al. |
| 8,012,931 B2 * | 9/2011 | Cujec .................... C12N 15/70 435/255.2 |
| 8,188,040 B2 | 5/2012 | Belouski et al. |
| 8,361,963 B2 | 1/2013 | Belouski et al. |
| 8,541,369 B2 | 9/2013 | Dickinson et al. |
| 8,722,622 B2 | 5/2014 | Das et al. |
| 9,120,871 B2 | 9/2015 | Slaaby et al. |
| 9,266,935 B2 | 2/2016 | Boettcher et al. |
| 9,273,106 B2 | 3/2016 | Belouski et al. |
| 9,434,778 B2 * | 9/2016 | Morin ...................... A61P 3/00 |
| 9,434,788 B2 | 9/2016 | Yadav et al. |
| 9,458,214 B2 | 10/2016 | Boettcher et al. |
| 9,744,213 B2 | 8/2017 | Wieczorek et al. |
| 9,895,417 B2 | 2/2018 | Wieczorek et al. |
| 2001/0011082 A1 * | 8/2001 | Diederich ............... A61P 19/00 514/102 |
| 2001/0012628 A1 | 8/2001 | Agarwal et al. |
| 2002/0164713 A1 | 11/2002 | Itoh et al. |
| 2003/0069395 A1 | 4/2003 | Sato et al. |
| 2003/0235536 A1 | 12/2003 | Blumberg |
| 2004/0185494 A1 | 9/2004 | Itoh et al. |
| 2004/0259780 A1 | 12/2004 | Glasebrook et al. |
| 2005/0037457 A1 | 2/2005 | Itoh et al. |
| 2005/0176631 A1 | 8/2005 | Heuer et al. |
| 2007/0191597 A1 | 8/2007 | Jain et al. |
| 2007/0212306 A1 * | 9/2007 | Quay .................... A61K 9/0043 424/85.5 |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0265200 A1 * | 11/2007 | Glaesner ................. A61P 3/10 514/6.9 |
| 2007/0286859 A1 | 12/2007 | Lazar et al. |
| 2007/0293430 A1 | 12/2007 | Frye et al. |
| 2008/0004206 A1 | 1/2008 | Rosen et al. |
| 2008/0057056 A1 | 3/2008 | Lazar et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0261877 A1 | 10/2008 | Ballance et al. |
| 2009/0305986 A1 | 12/2009 | Belouski et al. |
| 2010/0216715 A1 | 8/2010 | Tagmose et al. |
| 2010/0239554 A1 | 9/2010 | Schellenberger et al. |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2011/0195895 A1 | 8/2011 | Walker et al. |
| 2012/0035099 A1 | 2/2012 | Garibay et al. |
| 2013/0085098 A1 | 4/2013 | Dickinson et al. |
| 2013/0164310 A1 | 6/2013 | Annathur et al. |
| 2013/0231277 A1 | 9/2013 | Mohammadi et al. |
| 2017/0189486 A1 | 7/2017 | Morin et al. |
| 2017/0210777 A1 | 7/2017 | Minami |
| 2017/0334954 A1 | 11/2017 | Rodrigo et al. |

FOREIGN PATENT DOCUMENTS

| | | |
|---|---|---|
| WO | WO-9805787 A1 | 2/1998 |
| WO | WO-9823289 A1 | 6/1998 |
| WO | WO-9903887 A1 | 1/1999 |
| WO | WO-9951642 A1 | 10/1999 |
| WO | WO-9958572 A1 | 11/1999 |
| WO | WO-9967291 A2 | 12/1999 |
| WO | WO-0009560 A2 | 2/2000 |
| WO | WO-0026354 A1 | 5/2000 |
| WO | WO-0032767 A1 | 6/2000 |
| WO | WO-0042072 A2 | 7/2000 |
| WO | WO-0118172 A2 | 3/2001 |
| WO | WO-0136640 A2 | 5/2001 |
| WO | WO-0187922 A2 | 11/2001 |
| WO | WO-0244215 A2 | 6/2002 |
| WO | WO-02060919 A2 | 8/2002 |
| WO | WO-03011213 A2 | 2/2003 |
| WO | WO-03059270 A2 | 7/2003 |
| WO | WO-03074569 A2 | 9/2003 |
| WO | WO-03077834 A2 | 9/2003 |
| WO | WO-2004016750 A2 | 2/2004 |
| WO | WO-2004029207 A2 | 4/2004 |
| WO | WO-2004035752 A2 | 4/2004 |
| WO | WO-2004044859 A1 | 5/2004 |
| WO | WO-2004063351 A2 | 7/2004 |
| WO | WO-2004074455 A2 | 9/2004 |
| WO | WO-2004099249 A2 | 11/2004 |
| WO | WO-2004110472 A2 | 12/2004 |
| WO | WO-2005040217 A2 | 5/2005 |
| WO | WO-2005047327 A2 | 5/2005 |
| WO | WO-2005061712 A1 | 7/2005 |
| WO | WO-2005070963 A1 | 8/2005 |
| WO | WO-2005072769 A1 | 8/2005 |
| WO | WO-2005077981 A2 | 8/2005 |
| WO | WO-2005091944 A2 | 10/2005 |
| WO | WO-2005092925 A2 | 10/2005 |
| WO | WO-2005113606 A2 | 12/2005 |
| WO | WO-2005123780 A2 | 12/2005 |
| WO | WO-2006019447 A1 | 2/2006 |
| WO | WO-2006028595 A2 | 3/2006 |
| WO | WO-2006028714 A1 | 3/2006 |
| WO | WO-2006047350 A2 | 5/2006 |
| WO | WO-2006050247 A2 | 5/2006 |
| WO | WO-2006065582 A2 | 6/2006 |
| WO | WO-2006078463 A2 | 7/2006 |
| WO | WO-2006085967 A2 | 8/2006 |
| WO | WO-2007021494 A2 | 2/2007 |
| WO | WO-2008033413 A2 | 3/2008 |
| WO | WO-2008121563 A2 | 10/2008 |
| WO | WO-2008155134 A1 | 12/2008 |
| WO | WO-2009058322 A1 | 5/2009 |
| WO | WO-2009149171 A2 | 12/2009 |
| WO | WO-2010042747 A2 | 4/2010 |
| WO | WO-2010065439 A1 | 6/2010 |
| WO | WO-2010091122 A1 | 8/2010 |
| WO | WO-2010144502 A2 | 12/2010 |
| WO | WO-2010144508 A1 | 12/2010 |
| WO | WO-2011028228 A1 | 3/2011 |
| WO | WO-2011028229 A1 | 3/2011 |
| WO | WO-2011028344 A2 | 3/2011 |
| WO | WO-2011154349 A2 | 12/2011 |
| WO | WO-2012066075 A1 | 5/2012 |
| WO | WO-2013052311 A1 | 4/2013 |
| WO | WO-2013188181 A1 | 12/2013 |
| WO | WO-2016048999 A2 | 3/2016 |
| WO | WO-2016065326 A2 * | 4/2016 ............ A61K 38/00 |
| WO | WO-2017069158 A1 | 4/2017 |
| WO | WO-2017093465 A1 | 6/2017 |
| WO | WO-2017220706 A1 | 12/2017 |
| WO | WO-2020010117 A2 | 1/2020 |

OTHER PUBLICATIONS

Baird, A., et al., "The Fibroblast Growth Factor Family," Cancer Cells 3(6):239-243, Cold Spring Harbor Laboratory, United States (Jun. 1991).

Benhar, I. and Pastan, I., "Cloning, Expression and Characterization of the Fv Fragments of the Anti-carbohydrate mAbs B1 and B5 as Single-chain Immunotoxins," Protein Engineering Design and Selection 7(11):1509-1515, Oxford University Press, United Kingdom (Dec. 1994).

Burgess, W. H., et al., "The Heparin-binding (Fibroblast) Growth Factor Family of Proteins," Annual Review of Biochemistry 58:575-606, Annual Reviews, United States (1989).

(56) References Cited

OTHER PUBLICATIONS

Caliceti, P., et al., "Biopharmaceutical Properties of Uricase Conjugated to Neutral and Amphiphilic Polymers," Bioconjugate Chemistry 10(4):638-646, American Chemical Society, United States (Jul. 1999).
Capon, D.J., et al., "Designing CD4 Immunoadhesins for AIDS Therapy," Nature 337(6207):525-531, Nature Publishing Group, United Kingdom (Feb. 1989).
Cho, J.W. and Troy, F.A. II, "Polysialic Acid Engineering: Synthesis of Polysialylated Neoglycosphingolipids by using the Polysialyltransferase from Neuroinvasive Escherichia coli K1," Proceedings of the National Academy of Sciences USA 91(24):11427-11431, National Academy of Sciences, United States (Nov. 1994).
Delgado, C., et al., "The Uses and Properties of PEG-Linked Proteins," Critical Reviews in Therapeutic Drug Carrier Systems 9(3-4):249-304, CRC Press, Inc., United States (1992).
Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (Sep. 2002).
Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (Dec. 1999).
Genbank, "Transferrin precursor [*Homo sapiens*]" Accession AAA61140.1, accessed at http://www.ncbi.nlm.nih.gov/protein/AAA61140, accessed on Mar. 29, 2016, 3 pages.
Genbank, "Human Transferrin mRNA, Complete cds," Accession No. M12530.1, published on Jan. 14, 1995, accessed at https://www.ncbi.nlm.nih.gov/nuccore/339452/, accessed on Jan. 14, 1995, 2 pages.
Genbank, "*Homo sapiens* Transferrin (TF), mRNA," Accession No. NM001063.3 published on May 25, 2014, accessed at http://www.ncbi.nlm.nih.gov/nuccore/NM_001063, accessed on Sep. 24, 2014, 5 pages.
Genbank, "Transferrin [human, liver, mRNA, 2347 nt], " Accession No. S95936.1, published on May 7, 1993, accessed at https://www.ncbi.nlm.nih.gov/nuccore/S95936, accessed on Sep. 24, 2014, 2 pages.
Genbank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
Genbank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
Genbank, "*Homo sapiens* Transferrin (TF), mRNA," Accession No. XM039847 published on Jul. 16, 2001, accessed at https://www.ncbi.nlm.nih.gov/nuccore/XM_039847.1?report=genbank, accessed on Sep. 24, 2014, 2 pages.
Gimeno, R. E., and Moller, D. E, "FGF21-based pharmacotherapy—potential utility for metabolic disorders," Trends in Endocrinology and Metabolism 25(6):303-311, Elsevier, United Kingdom (Jun. 2014).
Hecht, R., et al., "Rationale-Based Engineering of a Potent Long-Acting FGF21 Analog for the Treatment of Type 2 Diabetes," PLoS One 7(11):e49345, Public Library of Science, United States (Nov. 2012).
Ho, S.N., et al., "Site-directed Mutagenesis by Overlap Extension using the Polymerase Chain Reaction," Gene 77(1):51-59, Elsevier Science Publishers B.V., Netherlands (Apr. 1989).
Horton, R.M., et al., "Gene Splicing by Overlap Extension," Methods in Enzymology 217:270-279, Academic Press, United States (Jan. 1993).
International Search Report and Written Opinion for International Application No. PCT/US2019/040356, European Patent Office, Netherlands, mailed on Jan. 7, 2020, 11 pages.

Kharitonenkov, A., et al., "FGF-21 as a Novel Metabolic Regulator," The Journal of Clinical Investigation 115(6):1627-1635, American Society for Clinical Investigation, United States (Jun. 2005).
Konig, T. and Skerra, A., "Use of an Albumin-binding Domain for the Selective Immobilisation of Recombinant Capture Antibody Fragments on ELISA Plates," Journal of Immunological Methods 218(1-2):73-83, Elsevier Science B.V., Netherlands (Sep. 1998).
Larrick, J.W., et al., "Rapid Cloning of Rearranged Immunoglobulin Genes from Human Hybridoma Cells using Mixed Primers and the Polymerase Chain Reaction," Biochemical and Biophysical Research Communications 160(3):1250-1256, Academic Press, United States (May 1989).
McKeehan, W. L., et al., "The heparan sulfate-fibroblast growth factor family: diversity of structure and function," Progress in Nucleic Acid Research and Molecular Biology 59:135-176, Academic Press, United States (Jan. 1997).
Morpurgo, M., et al., "Covalent Modification of Mushroom Tyrosinase with Different Amphiphic Polymers for Pharmaceutical and Biocatalysis Applications," Applied Biochemistry and Biotechnology 56(1):59-72, Humana Press, Inc., United States (Jan. 1996).
Nishimura, T., et al., "Identification of a Novel FGF, FGF-21, Preferentially Expressed in the Liver," Biochimica et Biophysica Acta 1492(1):203-206, Elsevier, Netherlands (Jun. 2000).
Ornitz, D. M., and Itoh, N., "Fibroblast Growth Factors," Genome Biology 2(3):reviews3005.1-3005.12, BioMed Central Ltd., United States (Mar. 2001).
Reuss, B., et al., "Fibroblast Growth Factors and Their Receptors in the Central Nervous System," Cell and Tissue Research 313(2):139-157, Springer-Verlag, Germany (Aug. 2003).
Roth, J., et al., "Expression of polysialic acid in human tumors and its significance for tumor growth," in *Polysialic Acid: From Microbes to Man*, Roth J., et al., eds., pp. 335-348, Birkhauser Verlag, Basel, Switzerland (1993).
Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (Oct. 1995).
Ruberti, F., et al., "The Use of the RACE Method to Clone Hybridoma cDNA when V Region Primers Fail," Journal of Immunological Methods 173(1):33-39, Elsevier, United States (Jul. 1994).
Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).
Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987), with English Language Abstract.
U.S. Department of Health and Human Services, "Immunogenicity Assessment for Therapeutic Protein Products," Guidance Document, Docket No. FDA-2013-D-0092, Issued by: Center for Drug Evaluation and Research and Center for Biologics Evaluation and Research, U.S. Food & Drug Administration, United States, 39 pages (Aug. 2014).
Vorobjev, P.E., et al., "Oligonucleotide Conjugated to Linear and Branched High Molecular Weight Polyethylene Glycol as Substrates for RNase H," Nucleosides & Nucleotides 18(11-12):2745-2750, Marcel Dekker, Inc., United States (Nov. 1999).
Wan, L. S., and Lee, P. F., "CMC of Polysorbates," Journal of Pharmaceutical Sciences 63(1):136-137, Elsevier, United States (Jan. 1974).
Wang, W., "Protein Aggregation and Its Inhibition in Biopharmaceutics," International Journal of Pharmaceutics 289(1-2):1-30, Elsevier/North-Holland Biomedical Press, Netherlands (Jan. 2005).
Ward, E.S. and Ghetie, V., "The Effector Functions of Immunoglobulins: Implications for Therapy," Therapeutic Immunology 2(2):77-94, Blackwell Science Ltd., United Kingdom (Apr. 1995).
Weidler, B., et al., "Pharmakokinetische Merkmale als Kriterien fur

(56) References Cited

OTHER PUBLICATIONS den klinischen Einsatz von Hydroxyethylstarke," Arzneimittel-Forschung 41(5):494-498, Editio Cantor, Germany (May 1991).

* cited by examiner

SEQUENCE LISTING

```
<160> NUMBER OF SEQ ID NOS: 3

<210> SEQ ID NO 1
<211> LENGTH: 182
<212> TYPE: PRT
<213> ORGANISM: Artificial Sequence
<220> FEATURE:
<223> OTHER INFORMATION: Q109 modified FGF-21
<220> FEATURE:
<221> NAME/KEY: misc_feature
<222> LOCATION: (109)..(109)
<223> OTHER INFORMATION: Wild-type Q109 replaced with para-acetyl-L-
      phenylalanine

<400> SEQUENCE: 1

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Xaa Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 2
<211> LENGTH: 182
<212> TYPE: PRT
```

<213> ORGANISM: Artificial Sequence
<220> FEATURE:
<223> OTHER INFORMATION: PEG-FGF-21 PEGYLATED Q109 modified FGF-21
<220> FEATURE:
<221> NAME/KEY: misc_feature
<222> LOCATION: (109)..(109)
<223> OTHER INFORMATION: Para-acetyl-L-phenylalanine linked to a 30 kDa poly(ethylene glycol) via oxime link

<400> SEQUENCE: 2

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Xaa Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 3
<211> LENGTH: 182
<212> TYPE: PRT
<213> ORGANISM: Artificial Sequence
<220> FEATURE:
<223> OTHER INFORMATION: FGF-21 wild type sequence

<400> SEQUENCE: 3

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
```

```
            115                 120                 125
Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
            165                 170                 175

Ser Pro Ser Tyr Ala Ser
        180
```

FGF-21 FORMULATIONS

REFERENCE TO SEQUENCE LISTING SUBMITTED ELECTRONICALLY VIA EFS-WEB

The content of the electronically submitted sequence listing (Name: 3338_133PC01_SeqListing.txt; Size: 5,532 bytes; and Date of Creation: Jun. 26, 2019) filed with the application is incorporated herein by reference in its entirety.

BACKGROUND

Field

This application pertains to, among other things, formulations comprising a FGF-21 polypeptide, e.g., a modified FGF-21 polypeptide, stabilized using chelators (e.g., DTPA), surfactants (e.g., PS80), and having specific pH ranges (e.g., about 7.1), for administration via various routes, including, for example, subcutaneous administration.

Background

Fibroblast growth factors (FGF) are polypeptides widely expressed in developing and adult tissues (Baird et al., Cancer Cells, 3:239-243, 1991) that play crucial roles in multiple physiological functions (McKeehan et al., Prog. Nucleic Acid Res. Mol. Biol. 59:135-176, 1998; Burgess, W. H. et al., Annu. Rev. Biochem. 58:575-606 (1989). According to the literature, the FGF family consists of at least twenty-two members (Reuss et al., Cell Tissue Res. 313: 139-157 (2003)).

FGF-21 can be used for the treatment of diseases and conditions associated with fibrosis. Fibrosis is the formation of excess fibrous connective tissue in an organ or tissue. Excess deposition of fibrous tissue is associated with pathological conditions that can lead to impairment of organ or tissue function. Affected organs can include the lungs (lung or pulmonary fibrosis), liver (liver or hepatic fibrosis), kidney (kidney or renal fibrosis), and heart (cardiac fibrosis). Fibrosis can also affect other tissues and organs including joints, skin, intestine, bone marrow, and others. Exemplary fibrotic conditions or diseases include, but are not limited to, nonalcoholic steatohepatitis (NASH), which affects the liver; diabetic kidney disease and diabetic nephropathy, which affect the kidney; and metabolic heart failure, which affects the heart. For example, NASH is characterized by fat accumulation, inflammation and damage in the liver of people who consume little or no alcohol, and the disease can lead to liver cirrhosis. NASH tends to be diagnosed in overweight or obese middle-aged people who often have elevated blood levels of certain lipids and diabetes or prediabetes.

FGF-21 has been reported to have a propensity to undergo proteolysis in vivo, form aggregates in vitro, and undergo deamidation (Gimeno and Moller, Trends Endocrinol Metab. 2014 June; 25 (6): 303-11; U.S. Pat. No. 8,361,963; Hecht et al., PLOS One. 2012; 7 (11): e49345; U.S. Patent Publication No. 2007/0293430; WO 2006/0065582), potentially limiting the shelf-life of pharmaceutical compositions containing FGF-21. Aggregates and deamidated forms of therapeutic polypeptides may potentially increase immunogenicity (see U.S. Department of Health and Human Services, "Immunogenicity Assessment for Therapeutic Protein Products," August 2014; Subramanyam (ed.), "Therapeutic Protein Immunogenicity Focus Group Newsletter," American Association of Pharmaceutical Scientists, Vol. 1, Issue 3 (December 2011)).

The present disclosure addresses, among other things, the need for pharmaceutical formulations that address the problems associated with the production of pharmaceutical formulations comprising FGF-21 polypeptides, and in particular, modified FGF-21 polypeptides.

BRIEF SUMMARY

The present disclosure provides pharmaceutical formulations comprising a fibroblast growth factor 21 (FGF-21) polypeptide, e.g., a modified FGF-21 polypeptide, and an aminopolycarboxylic acid cation chelator, such as diethylenetriaminepentaacetic acid (also known as pentetic acid or DTPA), wherein the formulation has improved stability compared to a reference formulation that does not contain the aminopolycarboxylic acid cation chelator. These pharmaceutical formulations exhibit one or more enhancements with respect to alternative formulations know in the art, for example, lower rates of deamidation, e.g., when stored at 40° C. for about a month, and/or lower rates of high molecular weight (HMW) aggregation when stored, e.g., at 40° C. for about a month.

The presence of an aminopolycarboxylic acid cation chelator in the disclosed formulation also mitigates FGF-21 polypeptide oxidation, and in particular methionine oxidation. For example, the presence of DTPA in the formulation can mitigate or prevent the oxidation of one or more FGF-21 methionines corresponding to amino acid 1 and/or amino acid 169 of SEQ ID NO: 3 (or corresponding methionines in SEQ ID NO: 1 and 2) at 25° C. and/or 40° C.

In some aspects, the DTPA cation chelator is present in an amount between about 10 μM and about 100 μM DTPA, between about 20 μM and about 90 μM DTPA, between about 30 μM and about 80 μM DTPA, between about 25 μM and about 75 μM DTPA, between about 40 μM and about 60 μM DTPA, between about 30 μM and about 70 μM DTPA, or between about 40 μM and about 70 μM DTPA. In other aspects, the DTPA cation chelator is present in an amount of about 40 μM, about 45 μM, about 50 μM, about 55 μM, or about 60 μM DTPA.

In some aspects of the pharmaceutical formulations disclosed herein, the pH of the formulation is above 6.5, above 6.6, above 6.7, above 6.8, above 6.9, above 7.0, above 7.1, above 7.2, above 7.3, above 7.4, or above 7.5.

In some aspects, the pH is between about 6.7 and about 7.5, between about 6.8 and about 7.5, between about 6.9 and about 7.4, between about 7.0 and about 7.3, between about 7.1 and 7.2, between about 7.1 and about 7.3, between about 7.1 and about 7.4, or between about 7.1 and about 7.5. In some aspects, the pH is about 6.7, about 6.8, about 6.9, about 7.0, about 7.1, about 7.2, about 7.3, about 7.4, or about 7.5. In some aspects, the pharmaceutical formulation is more stable than a reference formulation with a pH of 6.5.

In some aspects, the pharmaceutical formulations disclosed herein further comprise a surfactant, e.g., a nonionic surfactant. In some aspects, the nonanionic surfactant is a polysorbate, e.g., polyoxyethylene (20) sorbitan monooleate (polysorbate 80). In some aspects, the polysorbate 80 surfactant is present in an amount of about 0.01% to about 0.1% (w/v), about 0.02% to about 0.09% (w/v), about 0.03% to about 0.08% (w/v), about 0.04% to about 0.07% (w/v), or about 0.05% to about 0.06% (w/v).

In some aspects, the polysorbate 80 surfactant is present in an amount of at least about 0.01% (w/v), at least about 0.02% (w/v), at least about 0.03% (w/v), at least about 0.04% (w/v), at least about 0.05% (w/v), at least about 0.06% (w/v), at least about 0.07% (w/v), at least about 0.08% (w/v), at least about 0.09% (w/v or at least about 0.1% (w/v). In some aspects, the surfactant mitigates particulate and/or air bubble formation, e.g., when agitated on a shaker.

In some aspects, the pharmaceutical formulations disclosed herein further comprise an amino acid buffering agent, e.g., histidine. In some aspects, the histidine buffering agent is present in an amount of about 10 mM to about 100 mM histidine, about 20 mM to about 90 mM histidine, about 30 mM to about 80 mM histidine, about 40 mM to about 70 mM histidine, about 10 mM to about 30 mM histidine, about 15 mM to about 25 mM histidine, about 17.5 to about 22.5 histidine, or about 40 mM to about 60 mM histidine. In some aspects, the histidine buffering agent is present in an amount of about 10 mM histidine, about 15 mM histidine, about 20 mM histidine, about 25 mM histidine, about 30 mM histidine, about 35 mM histidine, about 40 mM histidine, about 45 mM histidine or about 50 mM histidine.

In some aspects, the pharmaceutical formulations disclosed herein further comprise an osmotic regulator, e.g., a sugar. In some aspects, the sugar is sucrose. In some aspects, the sucrose osmotic regulator is present in an amount of about 100 mM to about 1 M sucrose, about 200 mM to about 900 mM sucrose, about 300 mM to about 800 mM sucrose, about 400 mM to about 700 mM sucrose, or about 500 mM to about 600 mM sucrose. In some aspects, the sucrose osmotic regulator is present in an amount of about 100 mM sucrose, about 200 mM sucrose, about 300 mM sucrose, about 400 mM sucrose, about 500 mM sucrose, about 600 mM sucrose, about 700 mM sucrose, about 800 mM sucrose, about 900 mM sucrose, or about 1M sucrose.

In some aspects of the pharmaceutical formulations disclosed herein, the FGF-21 polypeptide comprises, consists, or consists essentially of a modified FGF-21 polypeptide. In some aspects, the modified FGF-21 polypeptide comprises a polypeptide having at least about 80%, at least about 85%, at least about 90%, at least about 95%, at least about 96%, at least about 97%, at least about 98%, or at least about 99% amino acid sequence identity to the amino acid sequence of SEQ ID NO: 3, wherein the polypeptide has a FGF-21 activity.

In some aspects, the modified FGF-21 polypeptide is linked to a half-life extending moiety. In some aspects, the modified FGF-21 polypeptide is linked to the half-life extending moiety via the side chain of a non-naturally encoded amino in the sequence of the FGF-21 polypeptide. In some aspects, the half-life extending moiety comprises albumin, an immunoglobulin constant region or a portion thereof, an immunoglobulin-binding polypeptide, an immunoglobulin G (IgG), albumin-binding polypeptide (ABP), a PASylation moiety, a HESylation moiety, XTEN, an Fc region, and any combination thereof. In some aspects, the half-life extending moiety comprises a water soluble polymer. In some aspects, the water soluble polymer is a polyethylene glycol (PEG). In some aspects, the PEG has an average molecular weight between about 10 kDa and about 40 kDa. In some aspects, the PEG has an average molecular weight of about 30 kDa.

In some aspects of the formulations disclosed herein, the non-naturally encoded amino acid is a phenylalanine derivative. In some aspects, the phenylalanine derivative is para-acetyl-L-phenylalanine. In some aspects, the half-life extending moiety is linked to the non-naturally encoded amino acid via an oxime linkage. In some aspects, the non-naturally encoded amino acid replaces amino acid Glutamine 109 of SEQ ID NO: 3.

In some aspects of the formulations disclosed herein, the FGF-21 polypeptide is present at a concentration between about 1 mg/ml and about 40 mg/ml. In some aspects, the FGF-21 polypeptide is present at a concentration of about 10 mg/ml or about 20 mg/ml. In some aspects, the FGF-21 polypeptide is present in an amount between about 1 mg and about 40 mg per dose. In some aspects, the FGF-21 polypeptide is present in an amount of about 1 mg per dose, about 5 mg per dose, about 10 mg per dose, about 20 mg per dose, or about 40 mg per dose.

In some aspects, the formulation is formulated for subcutaneous administration. In some aspects, the formulation is formulated for subcutaneous administration with a safety syringe. In some aspects, the formulation is formulated for daily or weekly administration. In some aspects, the formulation is an aqueous formulation. In some aspects of the formulations disclosed herein, the FGF-21 polypeptide is a PEG-FGF-21 (SEQ ID NO: 2).

The present disclosure provides a pharmaceutical formulation comprising (i) a FGF-21 polypeptide; (ii) histidine at a concentration between about 10 mM and about 50 mM; (iii) sucrose at a concentration between about 100 mM and about 1M; (iv) Polysorbate 80 at a concentration between about 0.01% and about 0.1% (w/v); and, (v) DTPA at a concentration between about 10 µM and about 100 µM; wherein the pH of the formulation is between about 6.7 and about 7.5.

The present disclosure also provides a pharmaceutical formulation comprising (i) a FGF-21 polypeptide; (ii) histidine at a concentration of about 20 mM; (iii) sucrose at a concentration of about 600 mM; (iv) Polysorbate 80 at a concentration of about 0.05% (w/v); and (v) DTPA at a concentration of about 50 µM; wherein the pH is about 7.1. Also provided is a pharmaceutical formulation comprising (i) a FGF-21 polypeptide; (ii) histidine at a concentration of 20 mM; (iii) sucrose at a concentration of 600 mM; (iv) Polysorbate 80 at a concentration of 0.05% (w/v); and (v) DTPA at a concentration of 50 µM; wherein the pH is 7.1.

The present disclosure also provides a pharmaceutical formulation comprising (i) a FGF-21 polypeptide; (ii) histidine at a concentration of about 20 mM; and (iii) sucrose at a concentration of about 600 mM; wherein the pH is about 7.0. Also provided is a pharmaceutical formulation comprising (i) a FGF-21 polypeptide; (ii) histidine at a concentration of 20 mM; and (iii) sucrose at a concentration of 600 mM; wherein the pH is 7.0.

Also provided is a pharmaceutical formulation comprising (i) PEG-FGF-21 at a concentration of about 10 mg/mL; (ii) histidine at a concentration of about 20 mM; (iii) sucrose at a concentration of about 600 mM; (iv) Polysorbate 80 at a concentration of about 0.05% (w/v); and (v) DTPA at a concentration of about 50 µM; wherein the pH is about 7.1.

Also provided is a pharmaceutical formulation comprising (i) PEG-FGF-21 at a concentration of about 20 mg/mL; (ii) histidine at a concentration of about 20 mM; (iii) sucrose at a concentration of about 600 mM; (iv) Polysorbate 80 at a concentration of about 0.05% (w/v); and (v) DTPA at a concentration of about 50 µM; wherein the pH is about 7.1.

Also provided is a pharmaceutical formulation comprising (i) PEG-FGF-21 at a concentration of 10 mg/mL; (ii) histidine at a concentration of 20 mM; (iii) sucrose at a concentration of 600 mM; (iv) Polysorbate 80 at a concentration of 0.05% (w/v); and (v) DTPA at a concentration of 50 µM; wherein the pH is 7.1.

Also provided is a pharmaceutical formulation comprising (i) PEG-FGF21 at a concentration of 20 mg/mL; (ii) histidine at a concentration of 20 mM; (iii) sucrose at a concentration of 600 mM; (iv) Polysorbate 80 at a concentration of 0.05% (w/v); and (v) DTPA at a concentration of 50 μM; wherein the pH is 7.1.

The present disclosure also provides methods to improve the stability of a pharmaceutical formulation comprising a FGF-21 polypeptide comprising admixing an aminopolycarboxylic acid cation chelator, wherein the formulation has improved stability compared to a reference formulation that does not contain the aminopolycarboxylic acid cation chelator. In one aspect, the improvement in stability comprises (i) an increase in physical stability, (ii) an increase in chemical stability, or (iii) a combination thereof. In one aspect, the increase in physical stability comprises (i) prevention or decrease of polypeptide aggregation, (ii) prevention or decrease of polypeptide fragmentation, or (iii) a combination thereof. In some aspects, the increase in chemical stability comprises (i) prevention or decrease of deamidation, (ii) prevention or decrease of oxidation, or (iii) a combination thereof. In some aspects, the improvement in stability comprises one or more of:
  (a) a lower rate of deamidation when stored at 40° C. for about a month with respect to the reference formulation;
  (b) a lower rate of high molecular weight (HMW) aggregation when stored at 40° C. for about a month with respect to the reference formulation; or
  (c) both (a) and (b).

In some aspects of the methods to improve the stability of a pharmaceutical formulation disclosed herein, the aminopolycarboxylic acid cation chelator mitigates oxidation of one or more methionines corresponding to amino acid 1 and/or amino acid 169 of SEQ ID NO: 3 (or corresponding methionines in SEQ ID: 1 or SEQ ID NO: 2, or other modified FGF-21 polypeptides) at 25° C. and/or 40° C. In some aspects, the aminopolycarboxylic acid cation chelator is DTPA. In some aspects, the DTPA cation chelator is present in an amount between about 10 UM and about 100 μM DTPA, between about 20 μM and about 90 μM DTPA, between about 25 μM and about 75 μM DTPA, between about 40 μM and about 60 μM DTPA, between about 30 μM and about 70 μM DTPA, between about 30 M and about 80 μM DTPA, or between about 40 μM and about 70 μM DTPA. In some aspects, the DTPA cation chelator is present in an amount of about 40 M, about 45 μM, about 50 μM, about 55 μM, or about 60 μM DTPA.

In some aspects, the methods to improve the stability of a pharmaceutical formulation disclosed herein further comprise adjusting the pH of the formulation above 6.5, above 6.6, above 6.7, above 6.8, above 6.9, or above 7.0. In some aspects, the pH is adjusted to a pH value between about 6.8 and about 7.5, or about 6.9 and about 7.4, or about 7.0 and about 7.3, or about 7.1 and 7.2, or about 7.1 and about 7.3, or about 7.1 and about 7.4, or about 7.1 and about 7.5. In some aspects, the adjusted pH is about 6.8, about 6.9, about 7.0, about 7.1, about 7.2, about 7.3, about 7.4, or about 7.5. In some aspects, the pH-adjusted formulation is more stable than a reference formulation (i.e., a formulation with the same components at the same concentrations but having a different pH) having a pH of 6.5.

In some aspects, the methods to improve the stability of a pharmaceutical formulation disclosed herein further comprise admixing a surfactant. In some aspects, the surfactant is a nonionic surfactant, e.g., a polysorbate. In some aspects, the polysorbate is polysorbate 80. In some aspects, the polysorbate 80 surfactant is admixed in an amount of about 0.01% to about 0.1% (w/v), about 0.02% to about 0.09% (w/v), about 0.03% to about 0.08% (w/v), about 0.04% to about 0.07% (w/v), or about 0.05% to about 0.06% (w/v). In some aspects, the polysorbate 80 surfactant is admixed in an amount of at least about 0.01% (w/v), at least about 0.02% (w/v), at least about 0.03% (w/v), at least about 0.04% (w/v), at least about 0.05% (w/v), at least about 0.06% (w/v), at least about 0.07% (w/v), at least about 0.08% (w/v), at least about 0.09% (w/v) or at least about 0.1% (w/v). In some aspects, the surfactant mitigates particulate and/or air bubble formation when the formulation is agitated, e.g., on a shaker.

In some aspects, the methods to improve the stability of a pharmaceutical formulation disclosed herein further comprise admixing an amino acid buffering agent, e.g., histidine. In some aspects, the histidine buffering agent is admixed in an amount of about 10 mM to about 100 mM histidine, about 20 mM to about 90 mM histidine, about 30 mM to about 80 mM histidine, about 40 mM to about 70 mM histidine, about 10 mM to about 30 mM histidine, about 15 mM to about 25 mM histidine, about 17.5 mM to about 22.5 mM histidine, or about 40 mM to about 60 mM histidine. In some aspects, the histidine buffering agent is admixed in an amount of about 10 mM histidine, about 15 mM histidine, about 20 mM histidine, about 25 mM histidine, about 30 mM histidine, about 35 mM histidine, about 40 mM histidine, about 45 mM histidine, or about 50 mM histidine.

In some aspects, the methods to improve the stability of a pharmaceutical formulation disclosed herein further comprise admixing an osmotic regulator, e.g., a sugar. In some aspects, the sugar is sucrose. In some aspects, the sucrose osmotic regulator is admixed in an amount of about 100 mM to about 1 M sucrose, about 200 mM to about 900 mM sucrose, about 300 mM to about 800 mM sucrose, about 400 mM to about 700 mM sucrose, or about 500 mM to about 600 mM sucrose. In some aspects, the sucrose osmotic regulator is admixed in an amount of about 100 mM sucrose, about 200 mM sucrose, about 300 mM sucrose, about 400 mM sucrose, about 500 mM sucrose, about 600 mM sucrose, about 700 mM sucrose, about 800 mM sucrose, about 900 mM sucrose, or about 1M sucrose.

In some aspects of the methods to improve the stability of a pharmaceutical formulation disclosed herein the FGF-21 polypeptide is a modified FGF-21 polypeptide. In some aspects, the modified FGF-21 polypeptide comprises a FGF-21 polypeptide sequence having at least about 80%, at least about 85%, at least about 90%, at least about 95%, at least about 96%, at least about 97%, at least about 98%, or at least about 99% amino acid sequence identity to the amino acid sequence of SEQ ID NO: 3, wherein the polypeptide has a FGF-21 activity. In some aspects, the modified FGF-21 polypeptide is linked to a half-life extending moiety. In some aspects, modified FGF-21 polypeptide is linked to the half-life extending moiety via the side chain of a non-naturally encoded amino in the sequence of the FGF-21 polypeptide.

In some aspects, the half-life extending moiety comprises, e.g., albumin, an immunoglobulin constant region or a portion thereof, an immunoglobulin-binding polypeptide, an IgG, ABP, a PASylation moiety, a HESylation moiety, XTEN, an Fc region, and any combination thereof. In some aspects, the half-life extending moiety comprises a water soluble polymer. In some aspects, the water soluble polymer is a PEG. In some aspects, the PEG has an average molecular weight between about 10 kDa and about 40 kDa. In some aspects, the PEG has an average molecular weight of about 30 kDa. In some aspects, the non-naturally encoded amino acid is a phenylalanine derivative. In some aspects, the phenylalanine derivative is para-acetyl-L-phenylalanine. In some aspects, the half-life extending moiety is linked to the non-naturally encoded amino acid via an oxime linkage. In some aspects, the non-naturally encoded amino acid replaces amino acid Glutamine 109 of SEQ ID NO: 3. In some aspects, the FGF-21 polypeptide is present at a concentration between about 1 mg/ml and about 40 mg/ml. In some aspects, the FGF-21 polypeptide is present at a concentration of about 10 mg/ml or about 20 mg/ml. In some aspects, the formulation is an aqueous formulation. In some aspects of the methods disclosed above, the FGF-21 polypeptide is PEG-FGF-21 (SEQ ID NO: 2).

The present disclosure also provides a method to improve the stability of a formulation comprising a FGF-21 polypeptide, wherein the method comprises admixing (i) histidine at a concentration between about 10 mM and about 50 mM; (ii) sucrose at a concentration between about 100 mM and about 1M; (iii) Polysorbate 80 at a concentration between about 0.01% and about 0.1% (w/v); and, (iv) DTPA at a concentration between about 10 UM and about 100 µM; wherein the pH of the formulation is between about 6.7 and about 7.5. Also provided is a method to improve the stability of a formulation comprising a FGF-21 polypeptide, wherein the method comprises admixing (i) histidine at a concentration of about 20 mM; (ii) sucrose at a concentration of about 600 mM; (iii) Polysorbate 80 at a concentration of about 0.05% (w/v); and (iv) DTPA at a concentration of about 50 µM; wherein the pH is about 7.1. Also provided is a method to improve the stability of a formulation comprising a FGF-21 polypeptide, wherein the method comprises admixing (i) histidine at a concentration of 20 mM; (ii) sucrose at a concentration of 600 mM; (iii) Polysorbate 80 at a concentration of 0.05% (w/v); and (iv) DTPA at a concentration of 50 µM; wherein the pH is 7.1.

The present disclosure also provides a method to improve the stability of a formulation comprising a FGF-21 polypeptide, wherein the method comprises admixing (i) histidine at a concentration of about 20 mM; (ii) sucrose at a concentration of about 600 mM; wherein the pH is about 7.0. The present disclosure also provides a method to improve the stability of a formulation comprising a FGF-21 polypeptide, wherein the method comprises admixing (i) histidine at a concentration of 20 mM; (ii) sucrose at a concentration of 600 mM; wherein the pH is 7.0. Also provided is a method to improve the stability of a formulation comprising PEG-FGF-21 at a concentration of about 10 mg/mL, wherein the method comprises admixing (i) histidine at a concentration of about 20 mM; (ii) sucrose at a concentration of about 600 mM; (iii) Polysorbate 80 at a concentration of about 0.05% (w/v); and (iv) DTPA at a concentration of about 50 M; wherein the pH is about 7.1.

The present disclosure also provides a method to improve the stability of a formulation comprising PEG-FGF-21 at a concentration of about 20 mg/mL, wherein the method comprises admixing (i) histidine at a concentration of about 20 mM; (ii) sucrose at a concentration of about 600 mM; (iii) Polysorbate 80 at a concentration of about 0.05% (w/v); and (iv) DTPA at a concentration of about 50 µM; wherein the pH is about 7.1. Also provided is a method to improve the stability of a formulation comprising PEG-FGF-21 at a concentration of about 10 mg/mL, wherein the method comprises admixing (i) histidine at a concentration of 20 mM; (ii) sucrose at a concentration of 600 mM; (iii) Polysorbate 80 at a concentration of 0.05% (w/v); and (iv) DTPA at a concentration of 50 M; wherein the pH is 7.1.

Also provided is a method to improve the stability of a formulation comprising PEG-FGF-21 at a concentration of about 20 mg/mL, wherein the method comprises admixing (i) histidine at a concentration of 20 mM; (ii) sucrose at a concentration of 600 mM; (iii) Polysorbate 80 at a concentration of 0.05% (w/v); and (iv) DTPA at a concentration of 50 µM; wherein the pH is 7.1.

The present disclosure also provides a pharmaceutical formulation prepared according to any of the methods to improve the stability of a formulation comprising FGF-21 (e.g., a modified FGF-21 such as PEG-FGF-21) disclosed herein. Also provided is a kit comprising (i) a pharmaceutical formulation comprising FGF-21 (e.g., a modified FGF-21 such as PEG-FGF-21) disclosed herein, and (ii) instructions for use.

The present disclosure also provides methods of treating or preventing a disease or condition associated with fibrosis and/or diabetes in a subject in need thereof comprising administering to the subject an effective amount of a pharmaceutical formulation comprising FGF-21 (e.g., a modified FGF-21 such as PEG-FGF-21) disclosed herein. In some aspects, the disease or condition is diabetes. In some aspects, the diabetes is type 2 diabetes. In some aspects, the disease or condition is nonalcoholic steatohepatitis (NASH). In some aspects, administration of an effective amount of the pharmaceutical formulation comprising FGF-21 (e.g., a modified FGF-21 such as PEG-FGF-21) disclosed herein to the subject decreases liver stiffness, decreases percentage body fat, decreases body weight, decreases liver-to-body weight ratio, decreases liver lipid content, decreases liver fibrosis area, decreases fasting blood glucose levels, decreases fasting triglyceride levels, decreases LDL cholesterol levels, decreases ApoB levels, decreases ApoC levels, increases HDL cholesterol, or any combination thereof. In some aspects, between about 1 mg and about 40 mg of FGF-21 polypeptide is administered per dose. In some aspects, about 1 mg, about 5 mg, about 10 mg, about 20 mg, or about 40 mg of FGF-21 polypeptide is administered per dose. In some aspects, the pharmaceutical formulation is administered subcutaneously. In some aspects, the pharmaceutical formulation is administered subcutaneously using a safety syringe. In some aspects, the pharmaceutical formulation is administered daily or weekly.

In some aspects, the administration of the pharmaceutical formulation comprising FGF-21 (e.g., a modified FGF-21 such as PEG-FGF-21) disclosed herein according to the methods of treatment disclosed herein to the subject results in (i) reduction in levels of liver fat; (ii) reduction in levels of liver injury; (iii) reduction in levels of fibrosis; (iv) decrease in levels of fibrosis biomarker serum Pro-C3 (N-terminal type III collagen propeptide); (v) decrease in levels of alanine aminotransferase (ALT); (vi) decrease in levels of aspartate aminotransferase (AST); (vii) increase in levels of serum adiponectin; (viii) decrease in levels of plasma LDL, increase in levels of plasma HDL; (ix) decrease in levels of plasma triglyceride; (x) reduction in level of liver stiffness; or (xi) any combination thereof, compared to the levels in untreated subjects or to the subject prior to the administration of the pharmaceutical formulation.

In some aspects, the pharmaceutical formulation is made by the process of admixing (i) PEG-FGF-21 in amount to achieve a final concentration of about 10 mg/mL; (ii) histidine in amount to achieve a final concentration of about 20 mM; (iii) sucrose in amount to achieve a final a concentration of about 600 mM; (iv) Polysorbate 80 in amount to achieve a final concentration of about 0.05% (w/v); and (v) DTPA in amount to achieve a final concentration of about 50 µM; and adjust the pH at about 7.1.

In some aspects, the pharmaceutical formulation is made by the process of admixing (i) PEG-FGF-21 in amount to achieve a final concentration of about 20 mg/mL; (ii) histidine in amount to achieve a final concentration of about 20 mM; (iii) sucrose in amount to achieve a final a concentration of about 600 mM; (iv) Polysorbate 80 in amount to achieve a final concentration of about 0.05% (w/v); and (v) DTPA in amount to achieve a final concentration of about 50 µM; and adjust the pH at about 7.1.

In some aspects, the pharmaceutical formulation is made by the process of admixing (i) PEG-FGF-21 in amount to achieve a final concentration of 10 mg/mL; (ii) histidine in amount to achieve a final concentration of 20 mM; (iii) sucrose in amount to achieve a final a concentration of 600 mM; (iv) Polysorbate 80 in amount to achieve a final concentration of 0.05% (w/v); and (v) DTPA in amount to achieve a final concentration of 50 µM; and adjust the pH at 7.1.

In some aspects, the pharmaceutical formulation is made by the process of admixing (i) PEG-FGF-21 in amount to achieve a final concentration of 20 mg/mL; (ii) histidine in amount to achieve a final concentration of 20 mM; (iii) sucrose in amount to achieve a final a concentration of 600 mM; (iv) Polysorbate 80 in amount to achieve a final concentration of 0.05% (w/v); and (v) DTPA in amount to achieve a final concentration of 50 M; and adjust the pH at 7.1.

BRIEF DESCRIPTION OF THE DRAWINGS

FIG. 1A shows deamidation in a formulation without pentetic acid (DTPA) or polysorbate 80. FIG. 1B shows deamidation in a formulation comprising pentetic acid (DTPA) and polysorbate 80.

FIG. 3A shows aggregation as a function of time, pH, and buffer system used. FIG. 3B shows aggregation at different temperatures and times (5° C., 14 months; 25° C., 1 month; 40° C., 1 day) and different pH.

FIG. 4A shows aggregation in a formulation without pentetic acid (DTPA) or polysorbate 80. FIG. 4B shows aggregation in a formulation with pentetic acid (DTPA) and polysorbate 80.

DETAILED DESCRIPTION

Figure 1A:
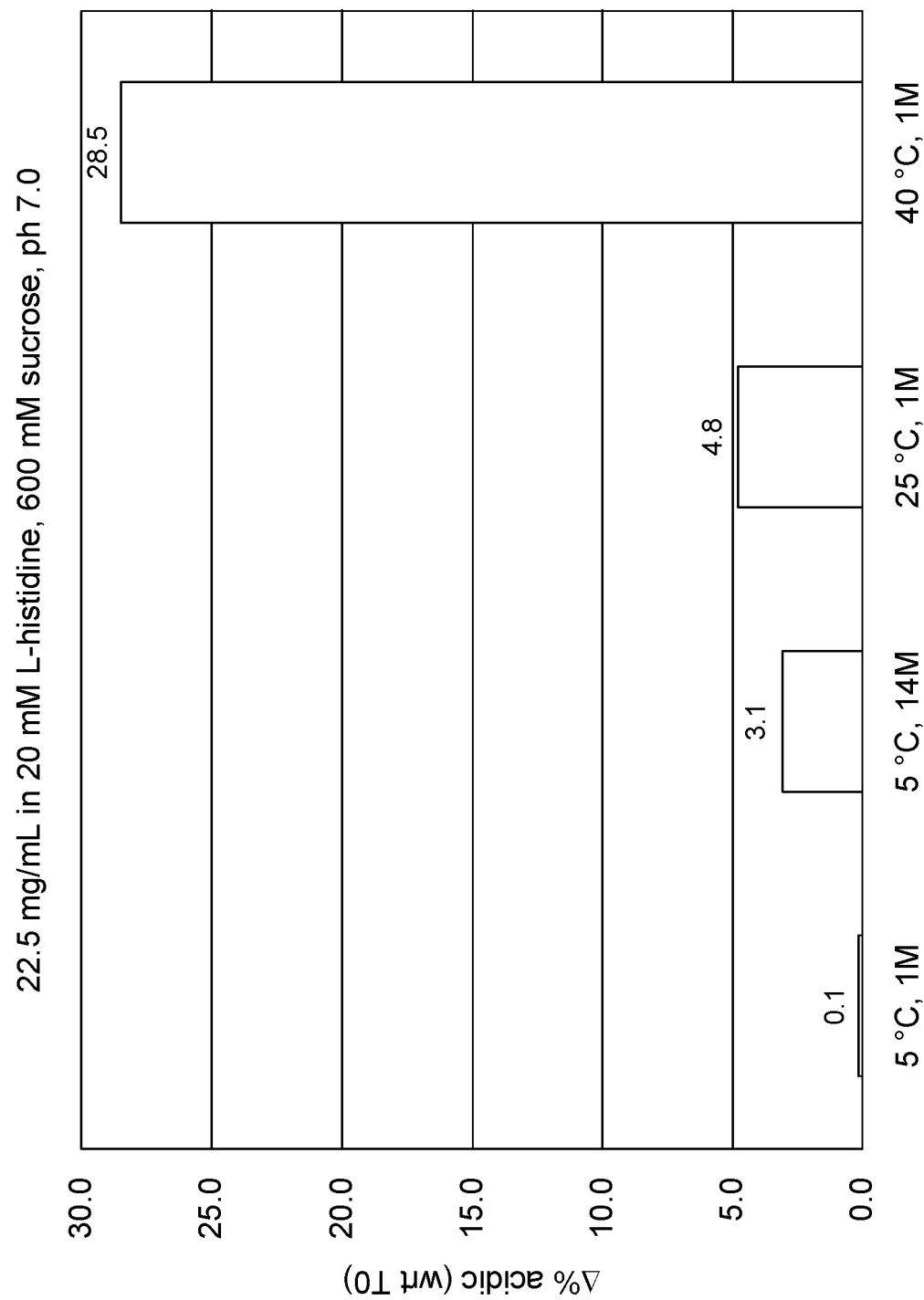
FIGS. 1A and 1B show deamidation of PEG-FGF-21 as a function of formulation composition.
Figure 1B:
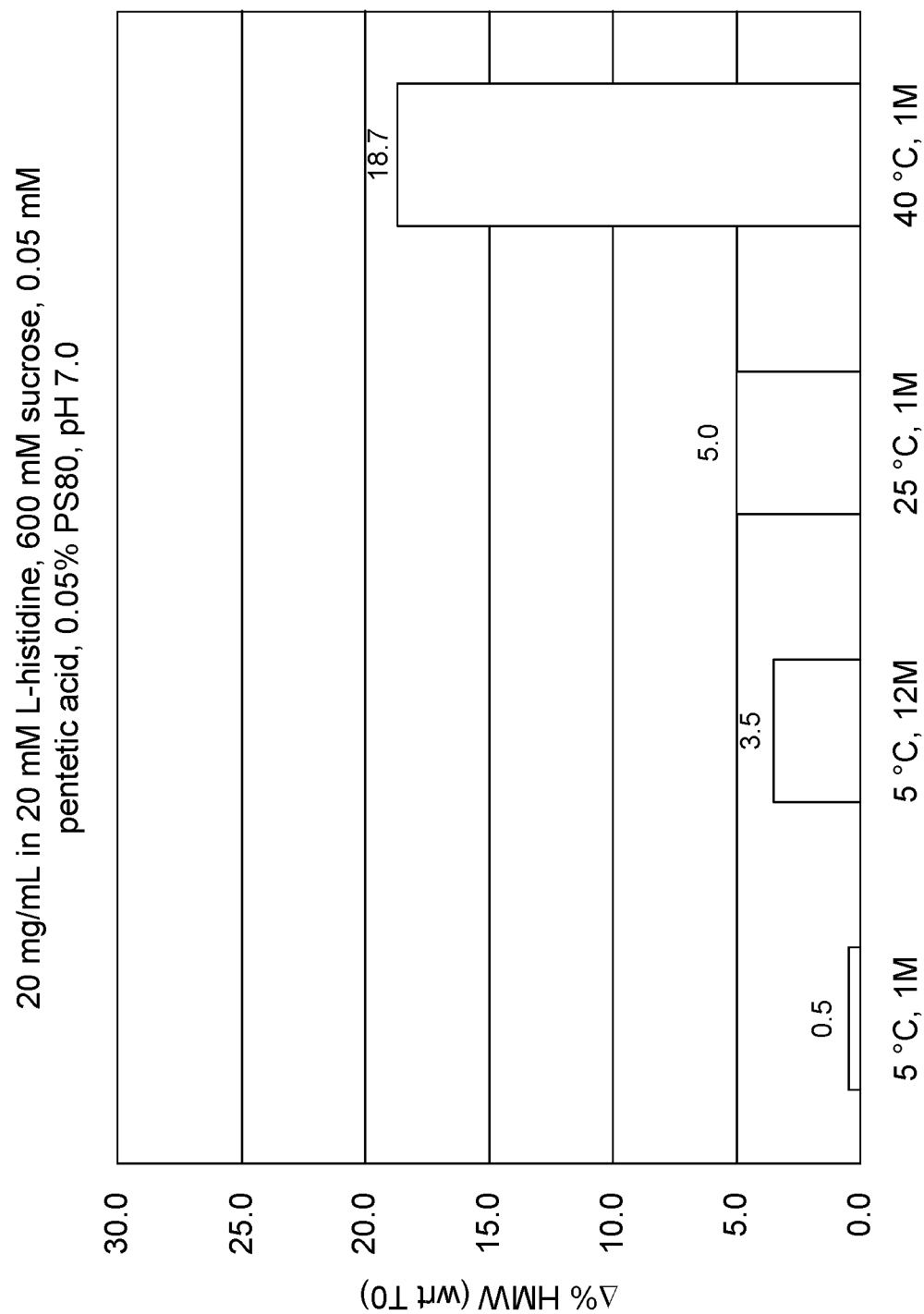

The present disclosure provides a stabilized pharmaceutical formulation comprising a fibroblast grow factor 21 (FGF-21) polypeptide, e.g., a modified FGF-21 polypeptide such as PEG-FGF-21 (SEQ ID NO: 2). The presence of an aminopolycarboxylic acid cation chelator such as DTPA has been observed to mitigate oxidation of one or more amino acid residues in the FGF-21 polypeptide, for example, methionines. Incorporation of DTPA in the FGF-21 formulation also lowers the rate of deamidation of the FGF-21 polypeptide during storage, and also reduces the rate of high molecular weight aggregation during storage. Further stabilization can be achieved by adjusting the pH of the formulation to 7.1. Also, the formulation can be further stabilized by adding a surfactant such as polysorbate 80.

The disclosure also provides methods to manufacture the disclosed formulation, as well as formulations produced by applying the disclosed method. Also provided are methods of treatment or prophylaxis of diseases associated with fibrosis, e.g., NASH and diabetes, comprising the administration of the disclosed stabilized formulations to a subject in need thereof.

Definitions

In order that the present disclosure can be more readily understood, certain terms are first defined. As used in this application, except as otherwise expressly provided herein, each of the following terms shall have the meaning set forth below. Additional definitions are set forth throughout the application.

The disclosure includes aspects in which exactly one member of the group is present in, employed in, or otherwise relevant to a given product or process. The disclosure includes aspects in which more than one, or all of the group members are present in, employed in or otherwise relevant to a given product or process.

The singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple." Thus, for example, reference to a "FGF-21" or "FGF-21 polypeptide" is a reference to one or more such proteins and includes equivalents thereof known to those of ordinary skill in the art, and so forth.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" as used herein to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

It is understood that wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

Aggregation: The term "aggregation" refers to the tendency of a polypeptide, e.g., an FGF-21 polypeptide disclosed herein to form non-covalently linked complexes with other molecules (such as other molecules of the same polypeptide) thereby forming high molecular weight complexes. Exemplary methods of measuring the formation of aggregates include analytical size exclusion chromatography as described in the Examples herein. Relative amounts of aggregation may be determined with respect to a reference compound, e.g., to identify a polypeptide having reduced aggregation. Relative amounts of aggregation can also be determined with respect to a reference formulation, e.g., to identify a formulation in which an FGF-21 polypeptide has reduced aggregation.

Amino acid substitution: The term "amino acid substitution" refers to replacing an amino acid residue present in a parent or reference sequence (e.g., a wild type sequence) with another amino acid residue. An amino acid can be substituted in a parent or reference sequence (e.g., a wild type polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position n, and Y and Z are alternative substituting amino acid residues that can replace A.

In the context of the present disclosure, substitutions (even when they are referred to as amino acid substitution) are conducted at the nucleic acid level, i.e., substituting an amino acid residue with an alternative amino acid residue is conducted by substituting the codon encoding the first amino acid with a codon encoding the second amino acid.

Approximately: As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association may, but need not, be causatively linked to the disease.

Biologically active: The term "biologically active" as applied to a molecule disclosed herein, e.g., an FGF-21 polypeptide, means any substance which can affect any physical or biochemical properties of a biological system, pathway, molecule, or interaction relating to a living organism. In particular, as used herein, biologically active molecules include, but are not limited to, any substance intended for diagnosis, cure, mitigation, treatment, or prevention of disease or conditions, e.g., diseases or conditions associated with fibrosis, in humans or other animals, or to otherwise enhance physical or mental well-being of humans or animals.

Conservative amino acid substitution: A "conservative amino acid substitution" is one in which the amino acid residue is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can also be used. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to amino acid residues of a polypeptide sequence, respectively, that are those that occur unaltered in the same position of two or more sequences being compared. Amino acids that are relatively conserved are those that are conserved amongst more related sequences than nucleotides or amino acids appearing elsewhere in the sequences.

In some aspects, two or more sequences are said to be "completely conserved" or "identical" if they are 100% identical to one another. In some aspects, two or more sequences are said to be "highly conserved" if they are at least 70% identical, at least 80% identical, at least 90% identical, or at least 95% identical to one another. In some aspects, two or more sequences are said to be "highly conserved" if they are about 70% identical, about 80% identical, about 90% identical, about 95%, about 98%, or about 99% identical to one another. In some aspects, two or more sequences are said to be "conserved" if they are at least 30% identical, at least 40% identical, at least 50% identical, at least 60% identical, at least 70% identical, at least 80% identical, at least 90% identical, or at least 95% identical to one another. In some aspects, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of a polynucleotide or polypeptide or may apply to a portion, region or feature thereof.

Deamidation: The term "deamidation" refers to the tendency of amino acid residues within a polypeptide to spontaneously undergo a deamidation reaction, thereby changing the chemical structure of the amino acid, and potentially affecting the function of the polypeptide. Exemplary methods of measuring deamidation are disclosed in the Examples herein. The relative amount of deamidation may be determined with respect to a reference compound, e.g., to identify a polypeptide having decreased deamidation. Relative amounts of deamidation can also be determined with respect to a reference formulation, e.g., to identify a formulation in which an FGF-21 polypeptide has reduced deamidation.

Disease associated with fibrosis: The term "disease associated with fibrosis" includes diseases, disorders, and conditions in which fibrosis has been observed to occur or in which fibrosis is known or thought to be associated with or contribute to disease etiology, progression, or symptoms, or in which fibrosis is known or thought to occur as the disease progresses.

The fibrosis may affect an organ or tissue such as the pancreas, lung, heart, kidney, liver, eyes, nervous system, bone marrow, lymph nodes, endomyocardium, or retroperitoneum. Exemplary diseases associated with fibrosis include, but are not limited to nonalcoholic steatohepatitis (NASH), liver fibrosis, pre-cirrhosis, cirrhosis, diffuse parenchymal lung disease, cystic fibrosis, lung or pulmonary fibrosis, progressive massive fibrosis, idiopathic pulmonary fibrosis, injection fibrosis, kidney or renal fibrosis, chronic kidney disease, diabetic kidney disease, focal segmental glomerulosclerosis, membranous nephropathy, IgA nephropathy, myelofibrosis, heart failure, metabolic heart failure, cardiac fibrosis, cataract fibrosis, cataract, ocular scarring, pancreatic fibrosis, skin fibrosis, intestinal fibrosis, intestinal strictures, endomyocardial fibrosis, atrial fibrosis, mediastinal fibrosis, Crohn's disease, retroperitoneal fibrosis, keloid, nephrogenic systemic fibrosis, scleroderma, systemic sclerosis, arthrofibrosis, Peyronie's syndrome, Dupuytren's contracture, diabetic neuropathy, adhesive capsulitis, alcoholic liver disease, hepatosteatosis, viral hepatitis, biliary disease, primary hemochromatosis, drug-related cirrhosis, cryptogenic cirrhosis, Wilson's disease, and, alpha 1-antitrypsin deficiency, interstitial lung disease (ILD), human fibrotic lung disease, macular degeneration, retinal retinopathy, vitreal retinopathy, myocardial fibrosis, Grave's ophthalmopathy, drug induced ergotism, cardiovascular disease, atherosclerosis/restenosis, hypertrophic scars, primary or idiopathic myelofibrosis, and inflammatory bowel disease (including, but not limited to, collagenous colitis). In some aspects, the disease associated with fibrosis can include liver fibrosis, kidney or renal fibrosis, lung or pulmonary fibrosis and heart or cardiac fibrosis. In some aspects, the disease associated with fibrosis can be liver fibrosis. In some aspects, the disease associated with fibrosis can be NASH.

Effective Amount: As used herein, the term "effective amount" of an FGF-21 formulation disclosed herein, is that amount sufficient to effect beneficial or desired results, for example, clinical results, and, as such, an "effective amount" depends upon the context in which it is being applied. For example, in the context of administering an FGF-21 polypeptide that treats NASH, an effective amount of the FGF-21 polypeptide is, for example, an amount sufficient to improve liver fat, liver injury or fibrosis (e.g., a reduction in liver fat, liver injury or fibrosis with respect to levels in untreated subjects or with respect to levels in the subject prior to the administration of the treatment).

In some aspects, an effective amount of an FGF-21 polypeptide, e.g., a modified FGF-21 polypeptide, to treat NASH can change the level of one or more fibrosis biomarkers: for example, decrease serum Pro-C3; decrease ALT or AST; increase serum adiponectin; decrease plasma LDL; increase plasma HDL; decrease plasma triglyceride levels, or any combination thereof, with respect to levels in untreated subjects or with respect to levels in the subject prior to the administration of the treatment.

The term "effective amount" can be used interchangeably with "effective dose," "therapeutically effective amount," or "therapeutically effective dose."

FGF-21 activity: The term "FGF-21 activity" refers to at least one biological activity of a FGF-21 polypeptide. The term "biological activity" refers to the ability of a molecule, e.g., an FGF-21 polypeptide to affect any physical or biochemical properties of a biological system, pathway, molecule, or interaction relating to an organism, including but not limited to, viruses, bacteria, bacteriophage, transposon, prion, insects, fungi, plants, animals, and humans.

For example, in the context of an unmodified or modified FGF-21, biological activity includes any of the biological functions performed by FGF-21. Exemplary methods of determining whether a molecule possesses at least one biological activity of wild-type FGF-21 (such as the wild-type FGF-21 polypeptide of SEQ ID NO: 3) can include any functional assays known in the art, including the methods disclosed in Example 5 and 17 of U.S. Appl Publ. No. 2017/0189486, which is herein incorporated by reference in its entirety.

The relative level of biological activity can be determined with respect to a reference compound, e.g., to identify a polypeptide having biological activity or having sufficiently high biological activity for an intended therapeutic use, e.g., having an $EC_{50}$ less than 5-fold, less than 10-fold, less than 20-fold, less than 50-fold, or less than 100-fold higher than the $EC_{50}$ of a reference compound. The relative level of biological activity can also be determined with respect to a reference formulation, e.g., to identify a formulation in which an FGF-21 polypeptide has biological activity or has sufficiently high biological activity for an intended therapeutic use, e.g., having an $EC_{50}$ less than 5-fold, less than 10-fold, less than 20-fold, less than 50-fold, or less than 100-fold higher than the $EC_{50}$ of a FGF-21 polypeptide in the reference formulation.

The reference compound described herein can be a FGF-21 sequence lacking a modification, such as a modification described herein. For example, the reference compound can be wild type FGF-21 or same modified FGF-21 polypeptide sequence without a fusion partner, e.g., without PEG. Exemplary reference compounds for PEG-FGF-21 include without limitation the wild-type FGF-21 polypeptide of SEQ ID NO: 3, and the modified FGF-21 polypeptide of SEQ ID NO: 1.

In some aspects, the reference compound can contain at least one non-naturally encoded amino acid, which can be linked to a linker, polymer, biologically active molecule, peptide, polypeptide, or half-life extending moiety described herein (e.g. PEG). In some aspects, a reference compound can contain at least one non-naturally encoded amino acid, which cannot be linked to a linker, polymer, biologically active molecule, peptide, polypeptide, or half-life extending moiety described herein (e.g. PEG). In some aspects, a reference compound may contain additional amino acid substitutions, deletions, and/or insertions. In some aspects, the comparison can be performed with a pegylated or non-pegylated form of the polypeptide; in the former instance, the comparison can be performed with a polypeptide comprising or not comprising a non-naturally encoded amino acid.

FGF-21 Polypeptide: The term "FGF-21 Polypeptide" refers to wild-type FGF-21 polypeptide and modified FGF-21 polypeptide.

Half-life extending moiety: The term "half-life extending moiety" refers to a pharmaceutically acceptable moiety, domain, or molecule covalently linked ("conjugated" or "fused") to an FGF-21 polypeptide, e.g., a modified FGF-21 polypeptide described herein, optionally via a non-naturally encoded amino acid, directly or via a linker, that prevents or mitigates in vivo proteolytic degradation or other activity-diminishing chemical modification of the modified FGF-21 polypeptide, increases half-life, and/or improves or alters other pharmacokinetic or biophysical properties including but not limited to increasing the rate of absorption, reducing toxicity, improving solubility, reducing protein aggregation, increasing biological activity and/or target selectivity of the modified FGF-21 polypeptide, increasing manufacturability, and/or reducing immunogenicity of the modified FGF-21 polypeptide, compared to a reference compound such as an unconjugated form of the modified FGF-21 polypeptide or wild-type FGF-21 polypeptide.

Identity: As used herein, the term "identity" refers to the overall monomer conservation between polymeric molecules, e.g., between polypeptide molecules. The term "identical" without any additional qualifiers, e.g., protein A is identical to protein B, implies the sequences are 100% identical (100% sequence identity). Describing two sequences as, e.g., "70% identical," is equivalent to describing them as having, e.g., "70% sequence identity."

Calculation of the percent identity of two polypeptide sequences, for example, can be performed by aligning the two sequences for optimal comparison purposes (e.g., gaps can be introduced in one or both of a first and a polypeptide sequences for optimal alignment and non-identical sequences can be disregarded for comparison purposes). In certain aspects, the length of a sequence aligned for comparison purposes is at least 30%, at least 40%, at least 50%, at least 60%, at least 70%, at least 80%, at least 90%, at least 95%, or 100% of the length of the reference sequence. The amino acids at corresponding amino acid positions are then compared.

When a position in the first sequence is occupied by the same amino acid as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa. Sequence alignments can be conducted using methods known in the art such as MAFFT, Clustal (ClustalW, Clustal X or Clustal Omega), MUSCLE, etc.

Different regions within a single polypeptide target sequence that aligns with a polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity (% ID) or of a first amino acid sequence to a second amino acid sequence is calculated as % ID=100× (Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

In vivo proteolytic degradation: The term "in vivo proteolytic degradation" refers to the cleavage of a polypeptide when introduced into a living system (e.g., when injected into an organism) which may result from proteases occurring in said organism. Proteolysis can potentially affect the biological activity or half-life of a polypeptide. For example, wild-type FGF-21 can undergo cleavage at the C-terminus, resulting in a truncated, inactive polypeptide. An exemplary method of measuring in vivo proteolysis of FGF-21 is the Meso Scale Discovery (MSD)-based electrochemiluminescent immunosorbent assay (ECLIA) described in Example 10 of U.S. Appl. Publ. No. US2017/0189486. The relative amount of in vivo or in vitro proteolysis may be determined with respect to a reference compound, e.g., to identify a polypeptide having decreased in vivo proteolysis. The relative amount of in vivo proteolysis can also be determined with respect to a reference formulation, i.e., to identify a formulation in which the FGF-21 polypeptide has decrease in vitro proteolysis.

Isolated: As used herein, the term "isolated" refers to a substance or entity (e.g., a polypeptide) that has been separated from at least some of the components with which it was associated (whether in nature or in an experimental setting). Isolated substances (e.g., proteins) can have varying levels of purity in reference to the substances from which they have been associated.

Linked: The terms "linked" or "attached" as used herein refers to an amino acid sequence covalently or non-covalently joined to a molecule, e.g., a water soluble polymer. The term "linked" means not only a fusion or a concatenation of an amino acid sequence (e.g., an FGF-21 polypeptide) with a second amino acid sequence (e.g., an albumin half-life extender), at the C-terminus or the N-terminus. It also includes insertion of a whole amino acid sequence (e.g., an XTEN half-life extender) into any two amino acids in a second amino acid sequence (e.g., an FGF-21 polypeptide). In some aspects, the linking can take place between a side chain of an amino acid in a first amino acid sequence (e.g., an FGF-21 polypeptide) and a second molecule (e.g., a second amino acid sequence or a soluble polymer such as PEG). In the context of the present disclosure, the terms "fused" or "fusion" indicate that at least two polypeptide chains have been operably linked and recombinantly expressed. In some aspects, two polypeptide chains can be "fused" as a result of chemical synthesis. In the context of the present disclosure, the terms "conjugate" or "conjugation" denote that two molecular entities (e.g., two polypeptides, or a polypeptide and a polymer such as PEG) have been chemically linked.

Modified FGF-21 polypeptide: As used herein, "modified FGF-21 polypeptide," "modified fibroblast growth factor 21" or "modified FGF-21" and unhyphenated forms thereof are used interchangeably and shall include those polypeptides and proteins that differ from wild-type FGF-21 (e.g., wild-type human FGF-21 of SEQ ID NO: 3) and typically have at least one biological activity of a fibroblast growth factor 21, as well as FGF-21 analogs, FGF-21 isoforms, FGF-21 mimetics, FGF-21 fragments, hybrid FGF-21 proteins, fusion proteins, oligomers and multimers, homologues, glycosylation pattern variants, variants, splice variants, and muteins thereof, regardless of the biological activity of the same. Modified FGF-21 polypeptides encompassed by this definition are described more in detail below.

Mutation: In the content of the present disclosure, the terms "mutation" and "amino acid substitution" as defined above (sometimes referred simply as a "substitution") are considered interchangeable.

Non-naturally encoded amino acid: A "non-naturally encoded amino acid" refers to an amino acid that is not one of the 20 common amino acids or pyrrolysine or selenocysteine. Other terms that can be used synonymously with the term "non-naturally encoded amino acid" are "non-natural amino acid," "unnatural amino acid," "non-naturally occurring amino acid," and various hyphenated and non-hyphenated versions thereof. The term "non-naturally encoded amino acid" also includes, but is not limited to, amino acids that occur by modification (e.g., post-translational modifications) of a naturally encoded amino acid (including but not limited to, the 20 common amino acids) but are not themselves naturally incorporated into a growing polypeptide chain by the translation complex. Examples of such non-naturally encoded amino acids include, but are not limited to, N-acetylglucosaminyl-L-serine, N-acetylglucosaminyl-L-threonine, and O-phosphotyrosine. In one specific aspect of the present disclosure, a non-naturally encoded amino acid is para-acetyl-L-phenylalanine.

Patient: As used herein, "patient" refers to a subject who can seek or be in need of treatment, requires treatment, is receiving treatment, will receive treatment, or a subject who is under care by a trained professional for a particular disease or condition.

Pharmaceutical composition: The term "pharmaceutical composition" refers to a preparation which is in such form as to permit the biological activity of the active ingredient (an FGF-21 polypeptide, e.g., a modified FGF-21 polypeptide such as PEG-FGF-21) to be effective, and which contains no additional components (e.g., excipients and water) which are unacceptably toxic to a subject to which the composition would be administered. Such composition can be sterile.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio. In general, approval by a regulatory agency of the Federal or state governments (or listed in the U.S. Pharmacopeia or other generally recognized pharmacopeia) for use in animals, and more particularly in humans implies that those compounds, materials, compositions, and/or dosage forms are pharmaceutically acceptable. Compounds, materials, compositions, and/or dosage forms that are generally acceptable as safe for therapeutically purposes are "therapeutically acceptable."

Pharmaceutically acceptable excipients: The phrase "pharmaceutically acceptable excipient," as used herein, refers any ingredient other than the active compounds described herein (for example, a vehicle capable of suspending or dissolving the active compound) and having the properties of being substantially nontoxic and non-inflammatory in a subject. Excipients can include, for example chelators, surfactants, buffering agents, osmotic regulators, antioxidants, emulsifiers, fillers (diluents), preservatives, sorbents, suspending or dispersing agents, sweeteners, and waters of hydration. Excipients that are generally accepted as safe for therapeutic purposes are "therapeutically acceptable excipients."

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some aspects, a "peptide" can be less than or equal to 50 amino acids long, e.g., about 5, 10, 15, 20, 25, 30, 35, 40, 45, or 50 amino acids long.

Preventing: As used herein, the term "preventing" refers to partially or completely delaying onset of an disease, disorder and/or condition; partially or completely delaying onset of one or more symptoms, features, or clinical manifestations of a particular disease, disorder, and/or condition; partially or completely delaying onset of one or more symptoms, features, or manifestations of a particular disease, disorder, and/or condition; partially or completely delaying progression from a particular disease, disorder and/or condition; and/or decreasing the risk of developing pathology associated with the disease, disorder, and/or condition. In some aspects, the pharmaceutical formulation disclosed in the present application can be used to prevent the onset, prevent the symptoms, or prevent complications of diseases or conditions associated with fibrosis such as NASH or diabetes.

Prophylactic: As used herein, "prophylactic" refers to a therapeutic or course of action used to prevent the onset of a disease or condition, or to prevent or delay a symptom of a disease or condition associated with fibrosis, e.g., NASH. In some aspect, the pharmaceutical formulations disclosed in the present application can be used prophylactically.

Prophylaxis: As used herein, a "prophylaxis" refers to a measure taken to maintain health and prevent or delay the onset of a disease or condition associates with fibrosis, e.g., NASH or diabetes, or to prevent or delay symptoms associated with a disease or condition.

Recombinant: A "recombinant" polypeptide or protein refers to a polypeptide or protein produced via recombinant DNA technology. Recombinantly produced polypeptides and proteins expressed in engineered host cells are considered isolated for the purpose of the disclosure, as are native or recombinant polypeptides which have been separated, fractionated, or partially or substantially purified by any suitable technique. The FGF-21 polypeptides disclosed herein can be recombinantly produced using methods known in the art. The proteins and peptides disclosed herein can also be chemically synthesized.

Similarity: As used herein, the term "similarity" refers to the overall relatedness between polymeric molecules, e.g. between polypeptide molecules. Calculation of percent similarity of polymeric molecules to one another can be performed in the same manner as a calculation of percent identity, except that calculation of percent similarity takes into account conservative substitutions as is understood in the art.

Solubility: The term "solubility" refers to the amount of a substance that can dissolve in another substance, e.g., the amount of an unmodified or modified FGF-21 polypeptide that can dissolve in an aqueous solution. An exemplary method of measuring the solubility of an unmodified or modified FGF-21 polypeptide is the plug flow solubility test described in Example 8 of U.S. Appl. Publ. No. US2017/0189486. Relative solubility can be determined with respect to a reference compound, e.g., to identify a polypeptide having increased solubility. In some aspects, relative solubility can be determined with respect to a reference formulation, e.g., to identify a formulation in which the polypeptide has increase solubility.

Subject: By "subject" or "individual" or "animal" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain aspects, the mammal is a human subject. In other aspects, a subject is a human patient. In a particular aspect, a subject is a human patient or cells thereof whether in vivo, in vitro or ex vivo, amenable to the methods described herein.

Suffering from: An individual who is "suffering from" a disease, disorder, and/or condition has been diagnosed with or displays one or more symptoms of the disease, disorder, and/or condition. In some aspects, the pharmaceutical formulations disclosed herein can administered to a subject suffering from a disease or condition associated with fibrosis such as NASH or diabetes.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some aspects, an individual who is susceptible to a disease, disorder, and/or condition (for example, cancer) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition.

In some aspects, an individual who is susceptible to a disease, disorder, and/or condition will develop the disease, disorder, and/or condition. In some aspects, an individual who is susceptible to a disease, disorder, and/or condition will not develop the disease, disorder, and/or condition. In some aspects, the pharmaceutical formulations disclosed herein can be administered to a subject susceptible to a disease or condition associated with fibrosis such as NASH or diabetes.

Therapeutic Agent: The terms "therapeutic agent" or "agent" refers to a molecular entity that, when administered to a subject, has a therapeutic, diagnostic, and/or prophylactic effect and/or elicits a desired biological and/or pharmacological effect. For example, in some aspects, a FGF-21 polypeptide disclosed herein (e.g., PEG-FGF-21) can be a therapeutic agent. In some aspects, an agent is another molecule which is co-administered as part of a combination therapy with at least one of the FGF-21 polypeptides disclosed herein.

Therapeutically effective amount: As used herein, the term "therapeutically effective amount" means an amount of an agent to be delivered (e.g., a FGF-21 polypeptide disclosed herein or a formulation comprising the polypeptide) that is sufficient, when administered to a subject suffering from or susceptible to an infection, disease, disorder, and/or condition, to treat, improve symptoms of, diagnose, prevent, and/or delay the onset of the infection, disease, disorder, and/or condition. Generally, the administration of the therapeutically effective amount is expected to result in a therapeutically effective outcome. Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Treat, treatment, therapy: As used herein, the terms "treat" or "treatment" or "therapy" or grammatical variants thereof refer to partially or completely, preventing, alleviating, ameliorating, improving, relieving, delaying onset of, inhibiting progression of, reducing severity of, and/or reducing incidence of one or more symptoms or features of a disease or condition associated with fibrosis, e.g., NASH or diabetes. For example, "treating" a disease associated with fibrosis can refer to preventing symptoms, ameliorating symptoms, delaying the onset of the disease or condition or its symptoms, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

ug, uM, uL: As used herein, the terms "ug," "uM," and "uL" are used interchangeably with "µg," "µM," and "µL" respectively.

Water Soluble Polymer: As used herein, the term "water soluble polymer" refers to any polymer that is soluble in aqueous solvents. Linkage of water soluble polymers to modified FGF-21 polypeptides can result in changes including, but not limited to, increased or modulated serum (in vivo) half-life, or increased or modulated therapeutic half-life relative to the unmodified form, modulated immunogenicity or toxicity, modulated physical association characteristics such as aggregation and multimer formation, altered receptor binding, altered binding to one or more binding partners, and altered receptor dimerization or multimerization.

The water soluble polymer can or cannot have its own biological activity, and can be utilized as a linker for attaching modified FGF-21 to other substances, including but not limited to one or more unmodified or modified FGF-21 polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, discrete PEG, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly [(2-hydroxyethyl)-DL-aspartamide, and the like, or mixtures thereof. Examples of such water soluble polymers include, but are not limited to, polyethylene glycol and serum albumin.

Various aspects of the disclosure are described in further detail in the following subsections.

I. FGF-21 Formulations

The present disclosure provides pharmaceutical formulations comprising a fibroblast growth factor 21 (FGF-21) polypeptide, e.g., a modified FGF-21 polypeptide such as PEG-FGF-21, and an aminopolycarboxylic acid cation chelator, e.g., diethylenetriaminepentaacetic acid (DTPA), wherein the formulations have improved stability compared to a reference formulation, i.e., a corresponding formulation containing the same components except that it does not contain the aminopolycarboxylic acid cation chelator.

The terms "chelator" or "cation chelator" are interchangeable and refer to any substance that is able to remove a metal ion from a solution system by forming a new complex ion that has different chemical properties than those of the original metal ion. In particular, the cation chelators disclosed herein are chelators that specifically bind divalent metals, e.g., $Ca^{++}$.

In some aspects, the pharmaceutical formulations disclosed herein exhibit one or more improvements in stability, e.g., a lower rate of deamidation, and/or a lower rate of aggregation. For example, the inclusion of an aminopolycarboxylic acid cation chelator such as DTPA in the pharmaceutical formulation can lower the rate of deamidation of the FGF-21 polypeptide (e.g., a modified FGF-21 polypeptide such as PEG-FGF-21) when stored at a certain temperature (e.g., 40° C.) for a certain period of time (e.g., 1 month) with respect to the reference formulation.

In some aspects, the aminopolycarboxylic acid cation chelator (e.g., DTPA) can lower the rate of deamidation of a FGF-21 polypeptide (e.g., a modified FGF-21 polypeptide such as PEG-FGF-21) in a pharmaceutical formulation stored at about 25° C., at about 30° C., at about 35° C., at about 40° C., or at about 45° C. with respect to the reference formulation. In some aspects, the aminopolycarboxylic acid cation chelator (e.g., DTPA) can lower the rate of deamidation of a FGF-21 polypeptide (e.g., a modified FGF-21 polypeptide such as PEG-FGF-21) in a pharmaceutical formulation stored at a temperature above 25° C., above 30° C., above 35° C., about 40° C., or about 45° C. with respect to the reference formulation.

In some aspects, the aminopolycarboxylic acid cation chelator (e.g., DTPA) can lower the rate of deamidation of a FGF-21 polypeptide (e.g., a modified FGF-21 polypeptide such as PEG-FGF-21) in a pharmaceutical formulation stored between about 20° C. and about 25° C., about 25° C. and about 30° C., about 30° C. and about 35° C., or about 40° C. and about 45° C. with respect to the reference formulation.

In some aspects, the aminopolycarboxylic acid cation chelator (e.g., DTPA) can lower the rate of deamidation of a FGF-21 polypeptide (e.g., a modified FGF-21 polypeptide such as PEG-FGF-21) in a pharmaceutical formulation at a temperature or temperature range disclosed above after storage for about 1 week, about 2 weeks, about 3 weeks, about 1 month, about 2 months, about 3 months, or about 4 months with respect to the reference formulation. In a specific aspect, the aminopolycarboxylic acid cation chelator (e.g., DTPA) can lower the rate of deamidation of a FGF-21 polypeptide (e.g., a modified FGF-21 polypeptide such as PEG-FGF-21) in a pharmaceutical formulation stored at 40° C. for about a month with respect to the reference formulation.

In some aspects, the aminopolycarboxylic acid cation chelator (e.g., DTPA) can lower the rate of high molecular weight (HMW) aggregation of a FGF-21 polypeptide (e.g., a modified FGF-21 polypeptide such as PEG-FGF-21) in a pharmaceutical formulation stored at about 25° C., at about 30° C., at about 35° C., at about 40° C., or at about 45° C. with respect to the reference formulation. In some aspects, the aminopolycarboxylic acid cation chelator (e.g., DTPA) can lower the rate of HMW aggregation of a FGF-21 polypeptide (e.g., a modified FGF-21 polypeptide such as PEG-FGF-21) in a pharmaceutical formulation stored at a temperature above 25° C., above 30° C., above 35° C., about 40° C., or about 45° C. with respect to the reference formulation.

In some aspects, the aminopolycarboxylic acid cation chelator (e.g., DTPA) can lower the rate of HMW aggregation of a FGF-21 polypeptide (e.g., a modified FGF-21 polypeptide such as PEG-FGF-21) in a pharmaceutical formulation stored between about 20° C. and about 25° C., about 25° C. and about 30° C., about 30° C. and about 35° C., or about 40° C. and about 45° C. with respect to the reference formulation.

In some aspects, the aminopolycarboxylic acid cation chelator (e.g., DTPA) can lower the rate of HMW aggregation of a FGF-21 polypeptide (e.g., a modified FGF-21 polypeptide such as PEG-FGF-21) in a pharmaceutical formulation at a temperature or temperature range disclosed above after storage for about 1 week, about 2 weeks, about 3 weeks, about 1 month, about 2 months, about 3 months, or about 4 months with respect to the reference formulation. In a specific aspect, the aminopolycarboxylic acid cation chelator (e.g., DTPA) can lower the rate of HMW aggregation of a FGF-21 polypeptide (e.g., a modified FGF-21 polypeptide such as PEG-FGF-21) in a pharmaceutical formulation stored at 40° C. for about a month with respect to the reference formulation.

In some aspects, the aminopolycarboxylic acid cation chelator, e.g., DTPA, prevents or mitigates oxidation of one or more amino acids, e.g., methionines, in the FGF-21 polypeptide (e.g., a modified FGF-21 polypeptide such as PEG-FGF-21). In particular aspects, the aminopolycarboxylic acid cation chelator, e.g., DTPA, prevents or mitigates oxidation of amino acid 1 and/or amino acid 169 of SEQ ID NO: 3 (or the corresponding amino acids in SEQ ID NO: 1 or SEQ ID NO: 2 or any other FGF-21 polypeptide) at 25° C. and/or 40° C.

In some specific aspects, the aminopolycarboxylic acid cation chelator is DTPA. Pentetic acid or diethylenetriaminepentaacetic acid (DTPA) is an aminopolycarboxylic acid consisting of a diethylenetriamine backbone with five carboxymethyl groups. The conjugate base of DTPA has a high affinity for metal cations. Thus, the penta-anion DTPA5− is potentially an octadentate ligand assuming that each nitrogen centre and each $COO^-$-group counts as a centre for coordination. The formation constants for its complexes are about 100 greater than those for EDTA. As a chelating agent, DTPA wraps around a metal ion by forming up to eight bonds. Transition metals, however, usually form less than eight coordination bonds. So, after forming a complex with a metal, DTPA still has the ability to bind to other reagents, as is shown by its derivative pendetide. For example, in its complex with copper (II), DTPA binds in a hexadentate manner utilizing the three amine centres and three of the five carboxylates.

In some other aspects, the aminopolycarboxylic acid cation chelator can be another aminopolycarboxylic acid cation chelator, such as ethylenediaminetetraacetic acid (EDTA), ethylene glycol-bis(β-aminoethyl ether)-N,N,N′,N′-tetraacetic acid (EGTA), 1,4,7,10-tetraazacyclododecane-1,4,7,10-tetraacetic acid (DOTA), or related compound, e.g., tiuxetan (a modified version of DTPA whose carbon backbone contains an isothiocyanatobenzyl and a methyl group). Other chelating agents related to DTPA and EDTA known in the art are those in which the nitrogens of the amide groups may be substituted by one or more $C_{1-18}$ alkyl groups, e.g. DTPA.BMA and EDTA.BMA.

In some aspects, the DTPA cation chelator is present in an amount between about 10 μM and about 100 μM, between 15 μM and about 95 μM, between about 20 μM and about 90 μM, between about 25 μM and about 85 μM, between about 30 μM and about 80 μM, between about 35 μM and about 75 μM, between about 40 μM and about 70 μM, between about 45 μM and about 65 μM, between about 50 μM and about 60 μM, between about 25 μM and about 75 μM, between about 40 UM and about 60 µM, between about 30 µM and about 70 µM, or between about 40 µM and about 75 µM.

In some aspects, the DTPA cation chelator is present in an amount of about 10 µM, about 15µ, about 20µ, about 25µ, about 30µ, about 35µ, about 40µ, about 45µ, about 50µ, about 55µ, about 60µ, about 65µ, about 70µ, about 75 µM, about 80 µM, about 85 µM, about 90 µM, about 95 µM or about 100 µM.

In some aspects, the DTPA cation chelator is present in an amount of at least about 15 µM, at least about 20 µM, at least about 25 µM, at least about 30 µM, at least about 35 UM, at least about 40 µM, at least about 45 µM, at least about 50 µM, at least about 55 µM, at least about 60 µM, at least about 65 µM, at least about 70 µM, or at least about 75 µM.

In a specific aspect, the aminopolycarboxylic acid cation chelator, e.g., DTPA, is present in an amount of 50 µM.

In some aspects, the pH of a formulation disclosed herein is above about 6.5, above about 6.6, above about 6.7, above about 6.8, above about 6.9, above about 7.0, above about 7.1, above about 7.2, above about 7.3, above about 7.4, or above about 7.5. In some aspects, the pH of the formulation is above 6.5, above 6.6, above 6.7, above 6.8, above 6.9, above 7.0, above 7.1, above 7.2, above 7.3, above 7.4, or above 7.5. In some aspects, the pH of the formulation is about 6.5, about 6.6, about 6.7, about 6.8, about 6.9, about 7.0, about 7.1, about 7.2, about 7.3, about 7.4, or about 7.5.

In some aspects, the pH of the formulation is between about 6.5 and about 7.5, about 6.6 and about 7.5, about 6.7 and about 7.5, about 6.8 and about 7.5, about 6.9 and about 7.5, about 7.0 and about 7.5, about 7.1 and about 7.5, about 7.2 and about 7.5, about 7.3 and about 7.5, about 7.4 and about 7.5, about 6.5 and about 7.4, about 6.5 and about 7.3, about 6.5 and about 7.2, about 6.5 and about 7.1, about 6.5 and about 7.0, about 6.5 and about 6.9, about 6.5 and about 6.8, about 6.5 and about 6.7, about 6.6 and about 7.4, about 6.7 and about 7.4, about 6.8 and about 7.4, about 6.9 and about 7.4, about 7.0 and about 7.4, about 7.1 and about 7.4, about 7.2 and about 7.4, about 7.3 and about 7.4, about 6.5 and about 7.3, about 6.6 and about 7.3, about 6.7 and about 7.3, about 6.8 and about 7.3, about 6.9 and about 7.3, about 7.0 and about 7.3, about 7.1 and about 7.3, about 7.2 and about 7.3, about 6.5 and about 7.2, about 6.6 and about 7.2, about 6.7 and about 7.2, about 6.8 and about 7.2, about 6.9 and about 7.2, about 7.0 and about 7.2, about 7.1 and about 7.2, about 6.9 and about 7.1, or about 7.0 and about 7.1.

In some aspects, the pH of the formulation is about 6.8, about 6.9, about 7.0, about 7.1, about 7.2, about 7.3, about 7.4, or about 7.5. In some aspects, the pharmaceutical formulation is more stable than a reference formulation with a pH of 6.5.

In some aspects, pharmaceutical formulation further comprises a surfactant. The term "surfactant" as used herein means any compound, typically an amphipathic molecule, that reduces surface tension when dissolved or suspended in water or water solutions, or which reduces interfacial tension between two liquids, or between a liquid and a solid. In the context of the present disclosure, a surfactant is any compound that decreases interfacial stress and shear in a solution comprising a FGF-21 polypeptide, e.g., a modified FGF-21 polypeptide such as PEG-FGF-21.

In some aspects, the surfactant is a nonionic surfactant, i.e., is a surfactant that tends to have no net charge in neutral solutions. In some aspects, the nonanionic surfactant is a polysorbate. Polysorbates are an important class of non-ionic surfactants used widely in protein pharmaceuticals to stabilize the proteins against interface-induced aggregation and to minimize surface adsorption of proteins (Wang W 2005. Protein aggregation and its inhibition in biopharmaceutics. Int J Pharm 289 (1-2): 1-30). Polysorbates are amphiphilic, non-ionic surfactants composed of fatty acid esters of polyoxyethylene (POE) sorbitan. Commercially available polysorbates are chemically diverse mixtures containing mainly sorbitan POE fatty acid esters.

As used herein, the term "polysorbate" refers to oleate esters of sorbitol and its anhydrides, typically copolymerized with ethylene oxide. Exemplary polysorbates include Polysorbate 20 (TWEEN 20; PS20) (polyoxyethylene (20) sorbitan monolaurate); Polysorbate 40 (TWEEN 40; PS40) (polyoxyethylene (20) sorbitan monopalmitate); Polysorbate 60 (TWEEN 60; PS60) (polyoxyethylene (20) sorbitan monostearate); and Polysorbate 80 (TWEEN 80; PS80) (polyoxyethylene (20) sorbitan monooleate).

The number 20 following the 'polyoxyethylene' part refers to the total number of oxyethylene —$(CH_2CH_2O)$— groups found in the molecule. The number following the 'polysorbate' part is related to the type of fatty acid associated with the polyoxyethylene sorbitan part of the molecule. Monolaurate is indicated by 20, monopalmitate is indicated by 40, monostearate by 60, and monooleate by 80. In some aspects, the non-ionic surfactant is present in an amount above the critical micelle concentration (CMC), which for polyoxyethylene sorbitan fatty acid esters is approximately an amount of at least 0.01 mg/ml. See Wan and Lee, Journal of Pharm Sci, 63, p. 136, 1974.

In some aspects, the polysorbate is polysorbate 80 (PS80). In some aspects, the polysorbate 80 surfactant is present in an amount of about 0.01% to about 0.1% (w/v), about 0.02% to about 0.1% (w/v), about 0.03% to about 0.1% (w/v), about 0.04% to about 0.1% (w/v), about 0.05% to about 0.1% (w/v), about 0.06% to about 0.1% (w/v), about 0.07% to about 0.1% (w/v), about 0.08% to about 0.1% (w/v), about 0.09% to about 0.1% (w/v), about 0.02% to about 0.09% (w/v), about 0.03% to about 0.09% (w/v), about 0.04% to about 0.09% (w/v), about 0.05% to about 0.09% (w/v), about 0.06% to about 0.09% (w/v), about 0.07% to about 0.09% (w/v), about 0.08% to about 0.09% (w/v), about 0.03% to about 0.08% (w/v), about 0.04% to about 0.08% (w/v), about 0.05% to about 0.08% (w/v), about 0.06% to about 0.08% (w/v), about 0.07% to about 0.08% (w/v), about 0.04% to about 0.07% (w/v), about 0.05% to about 0.07% (w/v), about 0.06% to about 0.07% (w/v), or about 0.05% to about 0.06% (w/v).

In some aspects, the polysorbate 80 surfactant is present in an amount of at least about 0.01% (w/v), at least about 0.02% (w/v), at least about 0.03% (w/v), at least about 0.04% (w/v), at least about 0.05% (w/v), at least about 0.06% (w/v), at least about 0.07% (w/v), at least about 0.08% (w/v), at least about 0.09% (w/v) or at least about 0.1% (w/v).

In some aspects, the surfactant, e.g., polysorbate 80, mitigates particulate and/or air bubble formation, e.g., when the formulation agitated on a shaker. In some aspects, the presence of the surfactant, e.g., polysorbate 80, in the formulation can reduce particulate formation by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% compared to the level of particulate formation in a reference formulation. In some aspects, the presence of the surfactant, e.g., polysorbate 80, in the formulation can reduce air bubble formation by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% compared to the level of bubble formation in a reference formulation.

In some aspects, the pharmaceutical formulation further comprises an amino acid buffering agent. Amino acids may be advantageously used as buffers in pharmaceutical applications because they naturally present substances which are easily metabolizable. Furthermore, amino acids used as buffers can also protect proteins in the amorphous phase if the formulation is freeze-dried. A suitable amino acid buffer can contain histidine, lysine, and/or arginine. Histidine has a good buffering capacity around pH 7.

As used herein, the term "histidine" comprises either L-histidine or D-histidine, a solvated form of histidine, a hydrated form (e.g., monohydrate) of histidine, or an anhydrous form of histidine, or a mixture thereof. Other suitable buffers in the formulations of the present disclosure glutamate, Tris, or succinate, to mention just a few.

In some specific aspects, the amino acid buffering agent is L-histidine.

In some aspects, the histidine buffering agent is present in an amount of about 10 mM to about 100 mM histidine, about 15 mM to about 100 mM histidine, about 20 mM to about 100 mM histidine, about 25 mM to about 100 mM, about 30 mM to about 100 mM histidine, about 35 mM to about 100 mM histidine, about 40 mM to about 100 mM histidine, about 45 mM to about 100 mM histidine, about 50 mM to about 100 mM histidine, about 55 mM to about 100 mM histidine, about 60 mM to about 100 mM histidine, about 65 mM to about 100 mM histidine, about 70 mM to about 100 mM histidine, about 75 mM to about 100 mM histidine, about 80 mM to about 100 mM histidine, about 85 mM to about 100 mM histidine, about 90 mM to about 100 mM histidine, or about 95 mM to about 100 mM histidine.

In some aspects, the histidine buffering agent is present in an amount of about 20 mM to about 90 mM histidine, about 25 mM to about 90 mM histidine, about 30 mM to about 90 mM histidine, about 35 mM to about 90 mM histidine, about 40 mM to about 90 mM histidine, about 45 mM to about 90 mM histidine, about 50 mM to about 90 mM histidine, about 55 mM to about 90 mM histidine, about 60 mM to about 90 mM histidine, about 65 mM to about 90 mM histidine, about 70 mM to about 90 mM histidine, about 75 mM to about 90 mM histidine, about 80 mM to about 90 mM histidine, about 85 mM to about 90 mM histidine, about 30 mM to about 80 mM histidine, about 35 mM to about 80 mM histidine, about 40 mM to about 80 mM histidine, about 45 mM to about 80 mM histidine.

In some aspects, the histidine buffering agent is present in an amount of about 50 mM to about 80 mM histidine, about 55 mM to about 80 mM histidine, about 60 mM to about 80 mM histidine, about 65 mM to about 80 mM histidine, about 70 mM to about 80 mM histidine, about 75 mM to about 80 mM histidine, about 40 mM to about 70 mM histidine, about 45 mM to about 70 mM histidine, about 50 mM to about 70 mM histidine, about 55 mM to about 70 mM histidine, about 60 mM to about 70 mM histidine, about 65 mM to about 70 mM histidine, about 10 mM to about 30 mM histidine, about 15 mM to about 30 mM histidine, about 20 mM to about 30 mM histidine, about 25 mM to about 30 mM histidine, about 15 mM to about 25 mM histidine, or about 20 mM to about 25 mM.

In some aspects, the histidine buffering agent is present in an amount of about 15 mM to about 20 mM histidine, about 40 mM to about 60 mM histidine, about 45 mM to about 60 mM histidine, about 50 mM to about 60 mM histidine, about 15.5 mM to about 24.5 mM histidine, about 16 mM to about 24 mM histidine, about 16.5 mM to about 23.5 mM histidine, about 17 mM to about 23 mM histidine, about 17.5 mM to about 22.5 mM histidine, about 18 mM to about 22 mM histidine, about 18.5 mM to about 21.5 mM histidine, about 19 mM to about 21 mM histidine, or about 19.5 mM to about 20.5 mM histidine.

In some aspects, the histidine buffering agent is present in an amount of about 10 mM histidine, about 11 mM histidine, about 12 mM histidine, about 13 mM histidine, about 14 mM histidine, about 15 mM histidine, about 16 mM histidine, about 17 mM histidine, about 18 mM histidine, about 19 mM histidine, about 20 mM histidine, about 21 mM histidine, about 22 mM histidine, about 23 mM histidine, about 24 mM histidine, about 25 mM histidine, about 26 mM histidine, about 27 mM histidine, about 28 mM histidine, about 29 mM histidine, about 30 mM histidine, about 31 mM histidine, about 32 mM histidine, about 33 mM histidine, about 34 mM histidine, about 35 mM histidine, about 36 mM histidine, about 37 mM histidine, about 38 mM histidine, about 39 mM histidine, about 40 mM histidine, about 41 mM histidine, about 42 mM histidine, about 43 mM histidine, about 44 mM histidine, about 45 mM histidine, about 46 mM histidine, about 47 mM histidine, about 48 mM histidine, about 49 mM histidine, or about 50 mM histidine.

In some aspects, the pharmaceutical formulation further comprises an osmotic regulator (also known in the art tonicity agents). According to the present disclosure the osmotic regulator (tonicity agent) can comprises a polyol, a saccharide, a carbohydrate, a salt, such as sodium chloride, or mixtures thereof. Exemplary polyols comprise those with a molecular weight that is less than about 600 kD (e.g., in the range from 120 to 400 kD), e.g., mannitol, trehalose, sorbitol, erythritol, isomalt, lactitol, maltitol, xylitol, glycerol, lactitol, propylene glycol, polyethylene glycol, inositol, or mixtures thereof.

Saccharide or carbohydrate osmotic regulators comprise monosaccharides, disaccharides and polysaccharides or mixtures thereof. In some aspects, the saccharide or carbohydrate is selected from the group consisting of fructose, glucose, mannose, sucrose, sorbose, xylose, lactose, maltose, sucrose, dextran, pullulan, dextrin, cyclodextrins, soluble starch, hydroxyethyl starch, water-soluble glucans, and mixtures thereof.

In some aspects, the osmotic regulator comprises a saccharide selected from the group of reducing sugar or non reducing sugar or mixtures thereof. In some aspects, the osmotic regulator the tonicity agent comprises a saccharide which is a non-reducing sugar, preferably a sugar selected from the group consisting of sucrose, trehalose, and mixtures thereof. In some specific aspects, the non-reducing sugar is sucrose.

In some aspects, the sucrose osmotic regulator is present in an amount of about 100 mM to about 1 M sucrose, about 200 mM to about 1 M sucrose, about 300 mM to about 1 M sucrose, about 400 mM to about 1 M sucrose, about 500 mM to about 1 M sucrose, about 600 mM to about 1 M sucrose, about 700 mM to about 1 M sucrose, about 800 mM to about 1 M sucrose, about 900 mM to about 1 M sucrose, about 200 mM to about 900 mM sucrose, about 300 mM to about 900 mM sucrose, about 400 mM to about 900 mM sucrose, about 500 mM to about 900 mM sucrose, about 600 mM to about 900 mM sucrose, about 700 mM to about 900 mM sucrose, about 800 mM to about 900 mM sucrose, about 300 mM to about 800 mM sucrose, about 400 mM to about 800 mM sucrose, about 500 mM to about 800 mM sucrose, about 600 mM to about 800 mM sucrose, about 700 mM to about 800 mM sucrose, about 400 mM to about 700 mM sucrose, about 500 mM to about 700 mM sucrose, about 600 mM to about 700 mM sucrose, or about 500 mM to about 600 mM sucrose.

In some aspects, the sucrose osmotic regulator is present in an amount of about 100 mM sucrose, about 150 mM sucrose, about 200 mM sucrose, about 250 mM sucrose, about 300 mM sucrose, about 350 mM sucrose, about 400 mM sucrose, about 450 mM sucrose, about 500 mM sucrose, about 550 mM sucrose, about 600 mM sucrose, about 650 mM sucrose, about 700 mM sucrose, about 750 mM sucrose, about 800 mM sucrose, about 850 mM sucrose, about 900 mM sucrose, about 950 mM sucrose, or about 1M sucrose.

In some aspects of the pharmaceutical formulations disclosed herein the FGF-21 polypeptide is a modified FGF-21 polypeptide. Numerous modified FGF-21 polypeptides known in the art can be used in the formulations disclosed herein, for example those disclosed in U.S. Pat. Nos. 8,012,931 and 9,434,788, both of which are herein incorporated by reference in their entireties. Fibroblast growth factor 21 (FGF-21) has been described in the literature (Nishimura et al., Biochimica et Biophysica Acta, 1492:203-206 (2000); WO 01/36640; and WO 01/18172, and U.S. Patent Publication No. 20040259780, each of which is incorporated by reference herein in its entirety). Unlike other FGFs, FGF-21 has been reported not to have proliferative and tumorigenic effects (Ornitz and Itoh, Genome Biology 2001, 2 (3): reviews3005.1-3005.12).

Certain FGF-21 polypeptides and uses thereof are described in U.S. Patent Publication No. 20010012628, U.S. Pat. No. 6,716,626, U.S. Patent Publication No. 2004/0259780, WO 03/011213, Kharitonenkov et al. J Clin Invest. 2005 June; 115 (6): 1627-35, WO 03/059270, U.S. Patent Publication No. 2005/0176631, WO 2005/091944, WO 2007/0293430, U.S. Patent Publication No. 2007/0293430, WO/2008/121563, U.S. Pat. No. 4,904,584, WO 99/67291, WO 99/03887, WO 00/26354, and U.S. Pat. No. 5,218,092 each of which is incorporated by reference herein in its entirety.

Additional FGF-21 that can be formulated as disclosed in the present application as described more in detail below.

In some aspects, the modified FGF-21 polypeptide comprises a polypeptide having at least about 70%, at least about 75%, at least about 80%, at least about 85%, at least about 90%, at least about 95%, at least about 96%, at least about 97%, at least about 98%, or at least about 99% amino acid sequence identity to the amino acid sequence of SEQ ID NO: 1 or SEQ ID NO: 3, wherein the polypeptide has a FGF-21 activity.

In some aspects, the modified FGF-21 polypeptide consists or consists essentially of a polypeptide having at least about 70%, at least about 75%, at least about 80%, at least about 85%, at least about 90%, at least about 95%, at least about 96%, at least about 97%, at least about 98%, or at least about 99% amino acid sequence identity to the amino acid sequence of SEQ ID NO: 1 or SEQ ID NO: 3, wherein the polypeptide has a FGF-21 activity.

In some aspects, the modified FGF-21 polypeptide is linked to a half-life extending moiety, e.g., via the side chain of a non-naturally encoded amino in the sequence of the FGF-21 polypeptide. Half-life extending moieties that can be linked to a modified FGF-21 polypeptide of the present disclosure, e.g., the FGF-21 polypeptide of SEQ ID NO: 1, comprise, e.g., albumin, an immunoglobulin constant region or a portion thereof, an immunoglobulin-binding polypeptide, an immunoglobulin G (IgG), albumin-binding polypeptide (ABP), a PASylation moiety, a HESylation moiety, XTEN, an Fc region, and any combination thereof. Half-life extending moieties that can be used to modify FGF-21 polypeptides are described more in detail below.

In some aspects, the half-life extending moiety comprises a water soluble polymer, e.g., a polyethylene glycol (PEG). In some aspects, the PEG has an average molecular weight between about 10 kDa and about 40 kDa. Thus, in some aspects, the PEG has an average molecular weight of about 10 kDa, about 15 kDa, about 20 kDa, about 25 kDa, about 30 kDa, about 35 kDa, or about 40 kDa.

In some aspects, the PEG has an average molecular weight of about 30 kDa. In some aspects, the PEG is an average molecular weight between about 15 kDa and about 40 kDa, between about 20 kDa and about 40 kDa, between about 25 kDa and about 40 kDa, between about 30 kDa and about 40 kDa, between about 35 kDa and about 40 kDa, between about 15 kDa and about 35 kDa, between about 15 kDa and about 30 kDa, between about 15 kDa and about 25 kDa, between about 15 kDa and about 20 kDa, between about 20 kDa and about 35 kDa, between about 25 kDa and about 35 kDa, or between about 30 kDa and about 35 kDa.

In some aspects, the half-life extending moiety, e.g., PEG, is linked to the FGF-21 polypeptide (e.g., a modified FGF-21 polypeptide of SEQ ID NO: 1 or SEQ ID NO: 2) via a non-naturally encoded amino acid, e.g., a phenylalanine derivative. In some aspects, the phenylalanine derivative is para-acetyl-L-phenylalanine. In some aspects, the half-life extending moiety is linked to the non-naturally encoded amino acid via an oxime linkage. In some aspects, the non-naturally encoded amino acid replaces amino acid Glutamine 109 of SEQ ID NO: 3 (wild type FGF-21).

In some specific aspects of the present disclosure, the FGF-21 polypeptide is PEG-FGF-21 (SEQ ID NO: 2), i.e., a derivative of the modified FGF-21 of SEQ ID NO: 1 in which glutamine 109 of wild type FGF-21 (SEQ ID NO: 3) has been replaced with para-acetyl-L-phenylalanine and a 30 kDa PEG chain has been covalently attached to the para-acetyl-L-phenylalanine at position 109 via an oxime linkage.

In some aspects, the FGF-21 polypeptide (e.g., modified FGF-21 polypeptide such as PEG-FGF-21) is present at a concentration between about 1 mg/ml and about 40 mg/ml. In some aspects, the FGF-21 polypeptide is present at a concentration of about 10 mg/ml, about 20 mg/ml, about 30 mg/ml, or about 40 mg/ml. In some aspects, the FGF-21 polypeptide (e.g., modified FGF-21 polypeptide such as PEG-FGF-21) is present at a concentration between about 1 mg/ml and 5 mg/ml, between about 5 mg/ml and about 10 mg/ml, between about 10 mg/ml and about 15 mg/ml, between about 15 mg/ml and about 20 mg/ml, between about 20 mg/ml and about 25 mg/ml, between about 25 mg/ml and about 30 mg/ml, between about 30 mg/ml and about 35 mg/ml, or between about 35 mg/ml and about 40 mg/ml.

In some aspects, the FGF-21 polypeptide (e.g., modified FGF-21 polypeptide such as PEG-FGF-21) is present at a concentration of 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, or 40 mg/ml. In some aspects, the concentration of the FGF-21 polypeptide is determined according to methods known in the art, or the specific methods disclosed in the Examples section of the present specification.

In some aspects, the FGF-21 polypeptide (e.g., a modified FGF-21 polypeptide such as PEG-FGF-21) is present in a formulation disclosed herein in an amount between about 1 mg and about 40 mg per dose. In some aspects, the FGF-21 polypeptide (e.g., a modified FGF-21 polypeptide such as PEG-FGF-21) is present in a formulation disclosed herein in an amount between about 1 mg and about 5 mg per dose, between about 5 mg and about 10 mg per dose, or between about 10 mg and about 15 mg per dose, between about 15 mg and about 20 mg per dose, or between about 20 mg and about 25 mg per dose, between about 25 mg and about 30 mg per dose, or between about 30 mg and about 35 mg per dose, or between about 35 mg and about 40 mg per dose. In some aspects, the FGF-21 polypeptide, e.g., a modified FGF-21 polypeptide such as PEG-FGF-21, is present in a formulation disclosed herein in an amount higher than 40 mg per dose.

In some aspects, the FGF-21 polypeptide (e.g., a modified FGF-21 polypeptide such as PEG-FGF-21) is present in a formulation disclosed herein in an amount of about 1 mg per dose, about 2 mg per dose, about 3 mg per dose, about 4 mg per dose, about 5 mg per dose, about 6 mg per dose, about 7 mg per dose, about 8 mg per dose, about 9 mg per dose, about 10 mg per dose, about 11 mg per dose, about 12 mg per dose, about 13 mg per dose, about 14 mg per dose, about 15 mg per dose, about 16 mg per dose, about 17 mg per dose, about 18 mg per dose, about 19 mg per dose, about 20 mg per dose, about 21 mg per dose, about 22 mg per dose, about 23 mg per dose, about 24 mg per dose, about 25 mg per dose, about 26 mg per dose, about 27 mg per dose, about 28 mg per dose, about 29 mg per dose, about 30 mg per dose, about 31 mg per dose, about 32 mg per dose, about 33 mg per dose, about 34 mg per dose, about 35 mg per dose, about 36 mg per dose, about 37 mg per dose, about 38 mg per dose, about 39 mg per dose, or about 40 mg per dose.

In some aspects, the pharmaceutical formulation is formulated for subcutaneous administration. As discussed below, other the pharmaceutical formulations disclosed herein can be administered via other routes. In some aspects, the pharmaceutical formulation is formulated for subcutaneous administration, e.g., with a safety syringe. In some aspects, the formulation is formulated for daily or weekly administration, for example, every 1, 2, 3, 4, 5, 6, days, every week, or every two weeks. In some aspects, the formulation is an aqueous formulation.

In some aspects, the present disclosure provides a pharmaceutical formulation comprising (i) a FGF-21 polypeptide, e.g., a modified FGF-21 polypeptide such as PEG-FGF-21; (ii) histidine at a concentration between about 10 mM and about 50 mM; (iii) sucrose at a concentration between about 100 mM and about 1M; (iv) Polysorbate 80 at a concentration between about 0.01% and about 0.1% (w/v); and, (v) DTPA at a concentration between about 10 UM and about 100 µM; wherein the pH of the formulation is between about 6.7 and about 7.5.

Also provided is a pharmaceutical formulation comprising (i) a FGF-21 polypeptide, e.g., a modified FGF-21 polypeptide such as PEG-FGF-21; (ii) histidine at a concentration of 20 mM; (iii) sucrose at a concentration of about 600 mM; (iv) Polysorbate 80 at a concentration of about 0.05% (w/v); and (v) DTPA at a concentration of about 50 µM; wherein the pH is about 7.1.

Also provided is a pharmaceutical formulation comprising (i) a FGF-21 polypeptide, e.g., a modified FGF-21 polypeptide such as PEG-FGF-21; (ii) histidine at a concentration of 20 mM; (iii) sucrose at a concentration of 600 mM; (iv) Polysorbate 80 at a concentration of 0.05% (w/v); and (v) DTPA at a concentration of 50 µM; wherein the pH is 7.1.

Also provided is a pharmaceutical formulation comprising (i) a FGF-21 polypeptide, e.g., a modified FGF-21 polypeptide such as PEG-FGF-21; (ii) histidine at a concentration of about 20 mM; and (iii) sucrose at a concentration of about 600 mM; wherein the pH is about 7.0.

Also provided is a pharmaceutical formulation comprising (i) a FGF-21 polypeptide, e.g., a modified FGF-21 polypeptide such as PEG-FGF-21; (ii) histidine at a concentration of 20 mM; and (iii) sucrose at a concentration of 600 mM; wherein the pH is 7.0.

In some specific aspects, the present disclosure provide a pharmaceutical formulation comprising (i) PEG-FGF-21 (SEQ ID NO: 2) at a concentration of about 10 mg/mL; (ii) histidine at a concentration of about 20 mM; (iii) sucrose at a concentration of about 600 mM; (iv) Polysorbate 80 at a concentration of about 0.05% (w/v); and (v) DTPA at a concentration of about 50 M; wherein the pH is about 7.1.

Also provided is a pharmaceutical formulation comprising (i) PEG-FGF-21 at a concentration of about 20 mg/mL; (ii) histidine at a concentration of about 20 mM; (iii) sucrose at a concentration of about 600 mM; (iv) Polysorbate 80 at a concentration of about 0.05% (w/v); and (v) DTPA at a concentration of about 50 µM; wherein the pH is about 7.1.

Also provided is a pharmaceutical formulation comprising (i) PEG-FGF-21 at a concentration of 10 mg/mL; (ii) histidine at a concentration of 20 mM; (iii) sucrose at a concentration of 600 mM; (iv) Polysorbate 80 at a concentration of 0.05% (w/v); and (v) DTPA at a concentration of 50 µM; wherein the pH is 7.1.

Also provided is a pharmaceutical formulation comprising (i) PEG-FGF21 at a concentration of 20 mg/mL; (ii) histidine at a concentration of 20 mM; (iii) sucrose at a concentration of 600 mM; (iv) Polysorbate 80 at a concentration of 0.05% (w/v); and (v) DTPA at a concentration of 50 µM; wherein the pH is 7.1.

The present disclosure also provides pharmaceutical formulation prepared according to any of the methods to improve the stability of a formulation comprising FGF-21 (e.g., a modified FGF-21 such as PEG-FGF-21) disclosed below.

II. Methods of Manufacture

The present disclosure also provides methods to improve or enhance the stability of a pharmaceutical formulation comprising a FGF-21 polypeptide, e.g., a modified FGF-21 polypeptide such as PEG-FGF-21, comprising admixing an aminopolycarboxylic acid cation chelator, e.g., DTPA, wherein the formulation has improved stability compared to a reference formulation that does not contain the aminopolycarboxylic acid cation chelator. These methods of stabilization comprise (i) the admixture of an aminopolycarboxylic acid cation chelator to the formulation, (ii) the admixture of a polysorbate surfactant, e.g., polysorbate 80, (iii) adjusting the pH of the formulation to approximately 7.1, or (iv) any combination thereof.

In some aspects, a pharmaceutical formulation described herein is made by the process of admixing (i) PEG-FGF-21 in amount to achieve a final concentration of about 10 mg/mL; (ii) histidine in amount to achieve a final concentration of about 20 mM; (iii) sucrose in amount to achieve a final a concentration of about 600 mM; (iv) Polysorbate 80 in amount to achieve a final concentration of about 0.05%

(w/v); and (v) DTPA in amount to achieve a final concentration of about 50 µM; and adjust the pH at about 7.1.

In some aspects, a pharmaceutical formulation described herein is made by the process of admixing (i) PEG-FGF-21 in amount to achieve a final concentration of about 20 mg/mL; (ii) histidine in amount to achieve a final concentration of about 20 mM; (iii) sucrose in amount to achieve a final a concentration of about 600 mM; (iv) Polysorbate 80 in amount to achieve a final concentration of about 0.05% (w/v); and (v) DTPA in amount to achieve a final concentration of about 50 µM; and adjust the pH at about 7.1.

In some aspects, a pharmaceutical formulation described herein is made by the process of admixing (i) PEG-FGF-21 in amount to achieve a final concentration of 10 mg/mL; (ii) histidine in amount to achieve a final concentration of 20 mM; (iii) sucrose in amount to achieve a final a concentration of 600 mM; (iv) Polysorbate 80 in amount to achieve a final concentration of 0.05% (w/v); and (v) DTPA in amount to achieve a final concentration of 50 µM; and adjust the pH at 7.1.

In some aspects, a pharmaceutical formulation described herein is made by the process of admixing (i) PEG-FGF-21 in amount to achieve a final concentration of 20 mg/mL; (ii) histidine in amount to achieve a final concentration of 20 mM; (iii) sucrose in amount to achieve a final a concentration of 600 mM; (iv) Polysorbate 80 in amount to achieve a final concentration of 0.05% (w/v); and (v) DTPA in amount to achieve a final concentration of 50 µM; and adjust the pH at 7.1.

As used herein the term "admixing" refers to the combination of the components of the formulations disclosed herein in no predetermined order to reach the disclosed concentrations by any means known in the art. For example, the excipients in a pharmaceutical formulation disclosed herein can be sequentially or simultaneously added to a FGF-21 polypeptide solution. Alternatively, a concentrated FGF-21 polypeptide solution can be added to a solution comprising all or part of the excipients in the formulation. In other aspects, the excipients can be incorporated to the formulation using, e.g., dialysis or filtration.

In some aspects, the improvements in stability resulting from the application of the disclosed method comprise, for example, (i) an increase on physical stability with respect to a reference formulation, (ii) an increase in chemical stability with respect to a reference formulation, or (iii) a combination thereof.

In some aspects, the increase in physical stability comprises (i) prevention or decrease of polypeptide aggregation, (ii) prevention or decrease of polypeptide fragmentation, or (iii) a combination thereof. In some aspects, the polypeptide aggregation observed in a pharmaceutical composition disclosed herein is about 90%, about 85%, about 80%, about 75%, about 70%, about 65%, about 60%, about 55%, about 50%, about 45%, about 40%, about 35%, about 30%, about 25%, about 20%, about 15%, or about 10% of the aggregation observed in a reference formulation. In some aspects, the polypeptide aggregation observed in a pharmaceutical composition disclosed herein is less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% of the aggregation observed in a reference formulation. In some aspects, the polypeptide fragmentation observed in a pharmaceutical composition disclosed herein is about 90%, about 85%, about 80%, about 75%, about 70%, about 65%, about 60%, about 55%, about 50%, about 45%, about 40%, about 35%, about 30%, about 25%, about 20%, about 15%, or about 10% of the fragmentation observed in a reference formulation. In some aspects, the polypeptide fragmentation observed in a pharmaceutical composition disclosed herein is less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% of the fragmentation observed in a reference formulation.

In some aspects, the increase in chemical stability comprises (i) prevention or decrease of polypeptide deamidation, (ii) prevention or decrease of polypeptide oxidation, or (iii) a combination thereof. In some aspects, the polypeptide deamidation observed in a pharmaceutical composition disclosed herein is about 90%, about 85%, about 80%, about 75%, about 70%, about 65%, about 60%, about 55%, about 50%, about 45%, about 40%, about 35%, about 30%, about 25%, about 20%, about 15%, or about 10% of the polypeptide deamidation observed in a reference formulation. In some aspects, the polypeptide deamidation observed in a pharmaceutical composition disclosed herein is less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% of the polypeptide deamidation observed in a reference formulation. In some aspects, the polypeptide oxidation observed in a pharmaceutical composition disclosed herein is about 90%, about 85%, about 80%, about 75%, about 70%, about 65%, about 60%, about 55%, about 50%, about 45%, about 40%, about 35%, about 30%, about 25%, about 20%, about 15%, or about 10% of the polypeptide oxidation observed in a reference formulation. In some aspects, the polypeptide oxidation observed in a pharmaceutical composition disclosed herein is less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% of the polypeptide oxidation observed in a reference formulation.

In some aspects, the methods to stabilize (improve or enhance the stability) a formulation disclosed herein can lower not only the level of degradation but also the rate of degradation: for example, the disclosed methods can lower the rate of polypeptide deamidation, lower the rate of polypeptide oxidation, lower the rate of polypeptide aggregation, lower the rate of proteolytic degradation, or any combination thereof, with respected to a reference formulation.

For example, the admixture of an aminopolycarboxylic acid cation chelator such as DTPA in a pharmaceutical formulation disclosed herein can lower the rate of deamidation of the FGF-21 polypeptide, e.g., a modified FGF-21 polypeptide such as PEG-FGF-21, when stored at a certain temperature for a certain period of time with respect to the reference formulation.

In some aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of deamidation of the FGF-21 polypeptide when the pharmaceutical formulation stored, for example, at about 25° C., at about 30° C., at about 35° C., at about 40° C., or at about 45° C. with respect to the reference formulation. In some aspects, the aminopolycarboxylic acid cation chelator (e.g., DTPA) can lower the rate of deamidation of the FGF-21 polypeptide, e.g., a modified FGF-21 polypeptide such as PEG-FGF-21, when the pharmaceutical formulation is stored at a temperature above 25° C., above 30° C., above 35° C., about 40° C., or about 45° C. with respect to the reference formulation. In some aspects, the aminopolycarboxylic acid cation chelator (e.g., DTPA) can lower the rate of deamidation of the FGF-21 polypeptide, e.g., a modified FGF-21 polypeptide such as PEG-FGF-21, when the pharmaceutical formulation is stored between about 20° C. and about 25° C., about 25° C. and about 30° C., about 30° C. and about 35° C., or about 40° C. and about 45° C. with respect to the reference formulation.

In some aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of deamidation of the FGF-21 polypeptide when the pharmaceutical formulation is stored at a temperature or temperature range disclosed above for about 1 week, about 2 weeks, about 3 weeks, about 1 month, about 2 months, about 3 months, or about 4 months with respect to the reference formulation.

In a specific aspect, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of deamidation of the FGF-21 polypeptide when the pharmaceutical formulation is stored at 40° C. for about a month with respect to the reference formulation.

In some aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of high molecular weight (HMW) aggregation of the FGF-21 polypeptide when the pharmaceutical formulation is stored at about 25° C., at about 30° C., at about 35° C., at about 40° C., or at about 45° C. with respect to the reference formulation.

In some aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of HMW aggregation of the FGF-21 polypeptide when the pharmaceutical formulation is stored at a temperature above 25° C., above 30° C., above 35° C., about 40° C., or about 45° C. with respect to the reference formulation. In some aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of HMW aggregation of the FGF-21 polypeptide when the pharmaceutical formulation is stored between at a temperature about 20° C. and about 25° C., about 25° C. and about 30° C., about 30° C. and about 35° C., or about 40° C. and about 45° C. with respect to the reference formulation.

In some aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of HMW aggregation of the FGF-21 polypeptide when the pharmaceutical formulation is stored at a temperature or temperature range disclosed above for about 1 week, about 2 weeks, about 3 weeks, about 1 month, about 2 months, about 3 months, or about 4 months with respect to the reference formulation.

In a specific aspect, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can lower the rate of HMW aggregation of the FGF-21 polypeptide when the pharmaceutical formulation is stored at 40° C. for about a month with respect to the reference formulation.

In some aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can prevent or mitigate the oxidation of one or more methionines in the FGF-21 polypeptide.

In particular aspects, the admixture of an aminopolycarboxylic acid cation chelator (e.g., DTPA) to a pharmaceutical formulation comprising an FGF-21 polypeptide (e.g., a modified FGF-21 polypeptide such as PEG-FGF-21) can prevent or mitigate the oxidation of amino acid 1 and/or amino acid 169 of SEQ ID NO: 3 (or the corresponding amino acids in SEQ ID NOS: 1, 2 or any other FGF-21 polypeptide), e.g., at 25° C. and/or at 40° C.

The disclosed methods can use the aminopolycarboxylic acid cation chelator DTPA. However, in some other aspects, the aminopolycarboxylic acid cation chelator can be, e.g., another aminopolycarboxylic acid cation chelator such as EDTA, EGTA, DOTA, a DTPA-related compound such as tiuxetan, or any chelating agents related to DTPA and EDTA known in the art, e.g. DTPA.BMA and EDTA.BMA.

In some aspects, the DTPA cation chelator can be admixed to an amount between about 10 µM and about 100 µM, between 15 µM and about 95 µM, between about 20 µM and about 90 µM, between about 25 µM and about 85 µM, between about 30 µM and about 80 µM, between about 35 µM and about 75 M, between about 40 UM and about 70 µM, between about 45 µM and about 65 µM, between about 50 µM and about 60 µM, between about 25 µM and about 75 µM, between about 40 µM and about 60 µM, between about 30 µM and about 70 µM, or between about 40 µM and about 75 µM.

In some aspects, the DTPA cation chelator can be admixed to an amount of about 10µ, about 15µ, about 20µ, about 25µ, about 30µ, about 35µ, about 40µ M, about 45 µM, about 50 µM, about 55 µM, about 60 µM, about 65 µM, about 70 µM, about 75 µM, about 80 µM, about 85 µM, about 90 µM, about 95 µM or about 100 µM.

In some aspects, the DTPA cation chelator can be admixed to an amount of at least about 15 µM, at least about 20 µM, at least about 25 µM, at least about 30 µM, at least about 35 µM, at least about 40 µM, at least about 45 µM, at least about 50 µM, at least about 55 M, at least about 60 µM, at least about 65 µM, at least about 70 µM, or at least about 75 µM.

In a specific aspect, the aminopolycarboxylic acid cation chelator, e.g., DTPA, is admixed to an amount of 50 µM.

In some aspects of the methods disclosed herein, the pH of the formulation is adjusted to a pH above about 6.5, above about 6.6, above about 6.7, above about 6.8, above about 6.9, above about 7.0, above about 7.1, above about 7.2, above about 7.3, above about 7.4, or above about 7.5.

In some aspects, the pH of the formulation is adjusted to a pH above 6.5, above 6.6, above 6.7, above 6.8, above 6.9, above 7.0, above 7.1, above 7.2, above 7.3, above 7.4, or above 7.5.

In some aspects, the pH of the formulation is adjusted to a pH of 6.5, 6.6, 6.7, 6.8, 6.9, 7.0, 7.1, 7.2, 7.3, 7.4, or 7.5.

In some aspects, the pH of the formulation is adjusted to a pH between about 6.5 and about 7.5, about 6.6 and about 7.5, about 6.7 and about 7.5, about 6.8 and about 7.5, about 6.9 and about 7.5, about 7.0 and about 7.5, about 7.1 and about 7.5, about 7.2 and about 7.5, about 7.3 and about 7.5, about 7.4 and about 7.5, about 6.5 and about 7.4, about 6.5 and about 7.3, about 6.5 and about 7.2, about 6.5 and about 7.1, about 6.5 and about 7.0, about 6.5 and about 6.9, about 6.5 and about 6.8, about 6.5 and about 6.7, about 6.6 and about 7.4, about 6.7 and about 7.4, about 6.8 and about 7.4, about 6.9 and about 7.4, about 7.0 and about 7.4, about 7.1 and about 7.4, about 7.2 and about 7.4, about 7.3 and about 7.4, about 6.5 and about 7.3, about 6.6 and about 7.3, about 6.7 and about 7.3, about 6.7 and about 7.3, about 6.8 and about 7.3, about 6.9 and about 7.3, about 7.0 and about 7.3, about 7.1 and about 7.3, about 7.2 and about 7.3, about 6.5 and about 7.2, about 6.6 and about 7.2, about 6.7 and about 7.2, about 6.8 and about 7.2, about 6.9 and about 7.2, about 7.0 and about 7.2, about 7.1 and about 7.2, about 6.9 and about 7.1, or about 7.0 and about 7.1, In some aspects, the pH of the formulation is adjusted to a pH of about 6.8, about 6.9, about 7.0, about 7.1, about 7.2, about 7.3, about 7.4, or about 7.5. In some aspects, the pharmaceutical formulation, after adjusting the pH, is more stable than a reference formulation with a pH of 6.5.

In some aspects, the pH of the formulation is adjusted to a pH of 6.8, 6.9, 7.0, 7.1, 7.2, 7.3, 7.4, or 7.5. In some aspects, the pharmaceutical formulation, after adjusting the pH, is more stable than a reference formulation with a pH of 6.5.

In some aspects, the method to improve the stability of a pharmaceutical formulation comprising a FGF-21 polypeptide (e.g., a modified FGF-21 polypeptide such as PEG-FGF-21) further comprises admixing a surfactant. In some aspects, the admixed surfactant is a nonionic surfactant, i.e., a surfactant that tends to have no net charge in neutral solutions. In some aspects, the admixed nonanionic surfactant is a polysorbate. In some aspects, the non-ionic surfactant is admixed in an amount above the critical micelle concentration (CMC), which for polyoxyethylene sorbitan fatty acid esters is approximately an amount of at least 0.01 mg/ml. See Wan and Lee, Journal of Pharm Sci, 63, p. 136, 1974. In some aspects of the present methods, the polysorbate is polysorbate 80 (PS80).

In some aspects, the PS80 surfactant is admixed to the pharmaceutical formulation in an amount of about 0.01% to about 0.1% (w/v), about 0.02% to about 0.1% (w/v), about 0.03% to about 0.1% (w/v), about 0.04% to about 0.1% (w/v), about 0.05% to about 0.1% (w/v), about 0.06% to about 0.1% (w/v), about 0.07% to about 0.1% (w/v), about 0.08% to about 0.1% (w/v), about 0.09% to about 0.1% (w/v), about 0.02% to about 0.09% (w/v), about 0.03% to about 0.09% (w/v), about 0.04% to about 0.09% (w/v), about 0.05% to about 0.09% (w/v), about 0.06% to about 0.09% (w/v), about 0.07% to about 0.09% (w/v), about 0.08% to about 0.09% (w/v), about 0.03% to about 0.08% (w/v), about 0.04% to about 0.08% (w/v), about 0.05% to about 0.08% (w/v), about 0.06% to about 0.08% (w/v), about 0.07% to about 0.08% (w/v), about 0.04% to about 0.07% (w/v), about 0.05% to about 0.07% (w/v), about 0.06% to about 0.07% (w/v), or about 0.05% to about 0.06% (w/v).

In some aspects, the polysorbate 80 surfactant is admixed in an amount of at least about 0.01% (w/v), at least about 0.02% (w/v), at least about 0.03% (w/v), at least about 0.04% (w/v), at least about 0.05% (w/v), at least about 0.06% (w/v), at least about 0.07% (w/v), at least about 0.08% (w/v), at least about 0.09% (w/v) or at least about 0.1% (w/v). In some aspects, the surfactant, e.g., PS80 is admixed in an amount sufficient to mitigates or prevent particulate formation and/or air bubble formation, e.g., when the formulation agitated (for example, on a shaker).

In some aspects, the method to improve the stability of a pharmaceutical formulation comprising a FGF-21 polypeptide (e.g., a modified FGF-21 polypeptide such as PEG-FGF-21) further comprises admixing an amino acid buffering agent, e.g., histidine (i.e., L-histidine, D-histidine, a solvated histidine, a hydrated histidine, an anhydrous histidine, or a mixture thereof).

In some aspects, the histidine buffering agent is admixed in an amount of about 10 mM to about 100 mM histidine, about 15 mM to about 100 mM histidine, about 20 mM to about 100 mM histidine, about 25 mM to about 100 mM histidine, about 30 mM to about 100 mM histidine, about 35 mM to about 100 mM histidine, about 40 mM to about 100 mM histidine, about 45 mM to about 100 mM histidine, about 50 mM to about 100 mM histidine, about 55 mM to about 100 mM histidine, about 60 mM to about 100 mM histidine, about 65 mM to about 100 mM histidine, about 70 mM to about 100 mM histidine, about 75 mM to about 100 mM histidine, about 80 mM to about 100 mM histidine, about 85 mM to about 100 mM histidine, about 90 mM to about 100 mM histidine, about 95 mM to about 100 mM histidine, about 20 mM to about 90 mM histidine, about 25 mM to about 90 mM histidine, about 30 mM to about 90 mM histidine, about 35 mM to about 90 mM histidine, about 40 mM to about 90 mM histidine, about 45 mM to about 90 mM histidine, about 50 mM to about 90 mM histidine, about 55 mM to about 90 mM histidine, about 60 mM to about 90 mM histidine, about 65 mM to about 90 mM histidine, about 70 mM to about 90 mM histidine, about 75 mM to about 90 mM histidine, about 80 mM to about 90 mM histidine, about 85 mM to about 90 mM histidine, about 30 mM to about 80 mM histidine, about 35 mM to about 80 mM histidine, about 40 mM to about 80 mM histidine, about 45 mM to about 80 mM histidine, about 50 mM to about 80 mM histidine, about 55 mM to about 80 mM histidine, about 60 mM to about 80 mM histidine, about 65 mM to about 80 mM histidine, about 70 mM to about 80 mM histidine, about 75 mM to about 80 mM histidine, about 40 mM to about 70 mM histidine, about 45 mM to about 70 mM histidine, about 50 mM to about 70 mM histidine, about 55 mM to about 70 mM histidine, about 60 mM to about 70 mM histidine, about 65 mM to about 70 mM histidine, about 10 mM to about 30 mM histidine, about 15 mM to about 30 mM histidine, about 20 mM to about 30 mM histidine, about 25 mM to about 30 mM histidine, about 15 mM to about 25 mM histidine, about 20 mM to about 25 mM, about 15 mM to about 20 mM histidine, about 40 mM to about 60 mM histidine, about 45 mM to about 60 mM histidine, about 50 mM to about 60 mM histidine, about 15.5 mM to about 24.5 mM histidine, about 16 mM to about 24 mM histidine, about 16.5 mM to about 23.5 mM histidine, about 17 mM to about 23 mM histidine, about 17.5 mM to about 22.5 mM histidine, about 18 mM to about 22 mM histidine, about 18.5 mM to about 21.5 mM histidine, about 19 mM to about 21 mM histidine, or about 19.5 mM to about 20.5 mM histidine.

In some aspects, the histidine buffering agent is admixed in an amount of about 10 mM histidine, about 11 mM histidine, about 12 mM histidine, about 13 mM histidine, about 14 mM histidine, about 15 mM histidine, about 16 mM histidine, about 17 mM histidine, about 18 mM histidine, about 19 mM histidine, about 20 mM histidine, about 21 mM histidine, about 22 mM histidine, about 23 mM histidine, about 24 mM histidine, about 25 mM histidine, about 26 mM histidine, about 27 mM histidine, about 28 mM histidine, about 29 mM histidine, about 30 mM histidine, about 31 mM histidine, about 32 mM histidine, about 33 mM histidine, about 34 mM histidine, about 35 mM histidine, about 36 mM histidine, about 37 mM histidine, about 38 mM histidine, about 39 mM histidine, about 40 mM histidine, about 41 mM histidine, about 42 mM histidine, about 43 mM histidine, about 44 mM histidine, about 45 mM histidine, about 46 mM histidine, about 47 mM histidine, about 48 mM histidine, about 49 mM histidine, or about 50 mM histidine.

In some aspects, the method to improve the stability of a pharmaceutical formulation comprising a FGF-21 polypeptide (e.g., a modified FGF-21 polypeptide such as PEG-FGF-21) further comprises admixing an osmotic regulator (tonicity agent). According to the present disclosure the osmotic regulator (tonicity agent) can comprises a polyol, a saccharide, a carbohydrate, a salt, such as sodium chloride, or mixtures thereof. Exemplary polyols comprise those with a molecular weight that is less than about 600 kD (e.g., in the range from 120 to 400 kD), e.g., mannitol, trehalose, sorbitol, erythritol, isomalt, lactitol, maltitol, xylitol, glycerol, lactitol, propylene glycol, polyethylene glycol, inositol, or mixtures thereof. Saccharide or carbohydrate osmotic regulators comprise monosaccharides, disaccharides and polysaccharides or mixtures thereof. In some aspects, the saccharide or carbohydrate is selected from the group consisting of fructose, glucose, mannose, sucrose, sorbose, xylose, lactose, maltose, sucrose, dextran, pullulan, dextrin, cyclodextrins, soluble starch, hydroxyethyl starch, water-soluble glucans, and mixtures thereof. In some aspects, the osmotic regulator comprises a saccharide selected from the group of reducing sugar or non reducing sugar or mixtures thereof. In some aspects, the osmotic regulator the tonicity agent comprises a saccharide which is a non-reducing sugar, preferably selected from the group consisting of sucrose, trehalose, and mixtures thereof. In some specific aspects, the non-reducing sugar is sucrose.

In some aspects, the sucrose osmotic regulator is admixed in an amount of about 100 mM to about 1 M sucrose, about 200 mM to about 1 M sucrose, about 300 mM to about 1 M sucrose, about 400 mM to about 1 M sucrose, about 500 mM to about 1 M sucrose, about 600 mM to about 1 M sucrose, about 700 mM to about 1 M sucrose, about 800 mM to about 1 M sucrose, about 900 mM to about 1 M sucrose, about 200 mM to about 900 mM sucrose, about 300 mM to about 900 mM sucrose, about 400 mM to about 900 mM sucrose, about 500 mM to about 900 mM sucrose, about 600 mM to about 900 mM sucrose, about 700 mM to about 900 mM sucrose, about 800 mM to about 900 mM sucrose, about 300 mM to about 800 mM sucrose, about 400 mM to about 800 mM sucrose, about 500 mM to about 800 mM sucrose, about 600 mM to about 800 mM sucrose, about 700 mM to about 800 mM sucrose, about 400 mM to about 700 mM sucrose, about 500 mM to about 700 mM sucrose, about 600 mM to about 700 mM sucrose, or about 500 mM to about 600 mM sucrose.

In some aspects, the sucrose osmotic regulator is admixed in an amount of about 100 mM sucrose, about 150 mM sucrose, about 200 mM sucrose, about 250 mM sucrose, about 300 mM sucrose, about 350 mM sucrose, about 400 mM sucrose, about 450 mM sucrose, about 500 mM sucrose, about 550 mM sucrose, about 600 mM sucrose, about 650 mM sucrose, about 700 mM sucrose, about 750 mM sucrose, about 800 mM sucrose, about 850 mM sucrose, about 900 mM sucrose, about 950 mM sucrose, or about 1M sucrose.

In some aspects, the FGF-21 polypeptide is a modified FGF-21 polypeptide. Numerous modified FGF-21 polypeptides known in the art can be used in the methods disclosed herein, for example those disclosed in U.S. Pat. Nos. 8,012,931 and 9,434,788, both of which are herein incorporated by reference in their entireties. Additional FGF-21 that can be formulated as disclosed in the present application as described more in detail below.

In some aspects, the modified FGF-21 polypeptide useful in the methods disclosed herein comprises a polypeptide having at least about 70%, at least about 75%, at least about 80%, at least about 85%, at least about 90%, at least about 95%, at least about 96%, at least about 97%, at least about 98%, or at least about 99% amino acid sequence identity to the amino acid sequence of SEQ ID NO: 3 (wild type human FGF-21), wherein the polypeptide has a FGF-21 activity.

In some aspects, the modified FGF-21 polypeptide useful in the methods disclosed herein consists or consists essentially of a polypeptide having at least about 70%, at least about 75%, at least about 80%, at least about 85%, at least about 90%, at least about 95%, at least about 96%, at least about 97%, at least about 98%, or at least about 99% amino acid sequence identity to the amino acid sequence of SEQ ID NO: 3 (wild type human FGF-21), wherein the polypeptide has a FGF-21 activity.

In some aspects, the modified FGF-21 polypeptide useful in the methods disclosed herein is linked to a half-life extending moiety, e.g., via the side chain of a non-naturally encoded amino in the sequence of the FGF-21 polypeptide. Half-life extending moieties that can be linked to a FGF-21 polypeptide of the present disclosure, e.g., a modified FGF-21 polypeptide of SEQ ID NO: 1 comprise, e.g., albumin, an immunoglobulin constant region or a portion thereof, an immunoglobulin-binding polypeptide, an IgG, an ABP, a PASylation moiety, a HESylation moiety, an XTEN, an Fc region, and any combination thereof. Half-life extending moieties that can be used to modify FGF-21 polypeptides are described more in detail below.

In some aspects, the half-life extending moiety useful in the methods disclosed herein comprises a water soluble polymer, e.g., a polyethylene glycol (PEG). In some aspects, the PEG has an average molecular weight between about 10 kDa and about 40 kDa, e.g., about 10 kDa, about 15 kDa, about 20 kDa, about 25 kDa, about 30 kDa, about 35 kDa, or about 40 kDa. In some aspects, the PEG has an average molecular weight of about 30 kDa. In some aspects, the PEG is an average molecular weight between about 15 kDa and about 40 kDa, between about 20 kDa and about 40 kDa, between about 25 kDa and about 40 kDa, between about 30 kDa and about 40 kDa, between about 35 kDa and about 40 kDa, between about 15 kDa and about 35 kDa, between about 15 kDa and about 30 kDa, between about 15 kDa and about 25 kDa, between about 15 kDa and about 20 kDa, between about 20 kDa and about 35 kDa, between about 25 kDa and about 35 kDa, or between 30 kDa and about 35 kDa.

In some aspects, the half-life extending moiety, e.g., PEG, is linked to the FGF-21 polypeptide, via a non-naturally encoded amino acid, e.g., a phenylalanine derivative. In some aspects, the phenylalanine derivative is para-acetyl-L-phenylalanine. In some aspects, the half-life extending moiety is linked to the non-naturally encoded amino acid via an oxime linkage. In some aspects, the non-naturally encoded amino acid replaces amino acid Glutamine 109 of SEQ ID NO: 3. In some aspects, the FGF-21 polypeptide is PEG-FGF-21 (SEQ ID NO: 2), i.e., the FGF-21 of SEQ ID NO: 1 in which glutamine 109 has been replaced with paraacetyl-L-phenylalanine and a 30 kDa PEG chain has been covalently attached to the para-acetyl-L-phenylalanine via an oxime linkage.

In some aspects of the methods disclosed herein, the FGF-21 polypeptide is present at a concentration between about 1 mg/ml and about 40 mg/ml. In some aspects, the FGF-21 polypeptide is present at a concentration of about 10 mg/ml, about 20 mg/ml, about 30 mg/ml, or about 40 mg/ml. In some aspects, the concentration of the FGF-21 polypeptide is determined according to methods known in the art, or the specific methods disclosed in the Examples section of the instant specification.

In some aspects of the methods disclosed herein, the formulation is formulated for subcutaneous administration. In some aspects, the formulation is formulated for subcutaneous administration with a safety syringe. In some aspects, the formulation is formulated for daily or weekly administration. In some aspects, the formulation is an aqueous formulation.

The present disclosure provides a method to improve the stability of a formulation comprising a FGF-21 polypeptide, e.g., a modified FGF-21 polypeptide such as PEG-FGF-21, comprising admixing (i) histidine at a concentration between about 10 mM and about 50 mM; (ii) sucrose at a concentration between about 100 mM and about 1M; (iii) Polysorbate 80 at a concentration between about 0.01% and about 0.1% (w/v); and, (iv) DTPA at a concentration between about 10 UM and about 100 µM; wherein the pH of the formulation is between about 6.7 and about 7.5.

The present disclosure provides a method to improve the stability of a formulation comprising a FGF-21 polypeptide, e.g., a modified FGF-21 polypeptide such as PEG-FGF-21, comprising admixing (i) histidine at a concentration between about 15 mM and about 45 mM; (ii) sucrose at a concentration between about 200 mM and about 900 mM; (iii) Polysorbate 80 at a concentration between about 0.02% and about 0.09% (w/v); and, (iv) DTPA at a concentration between about 20 µM and about 90 µM; wherein the pH of the formulation is between about 6.8 and about 7.4.

The present disclosure provides a method to improve the stability of a formulation comprising a FGF-21 polypeptide, e.g., a modified FGF-21 polypeptide such as PEG-FGF-21, comprising admixing (i) histidine at a concentration between about 15 mM and about 40 mM; (ii) sucrose at a concentration between about 300 mM and about 800 mM; (iii) Polysorbate 80 at a concentration between about 0.03% and about 0.08% (w/v); and, (iv) DTPA at a concentration between about 30 µM and about 80 µM; wherein the pH of the formulation is between about 6.9 and about 7.3.

The present disclosure provides a method to improve the stability of a formulation comprising a FGF-21 polypeptide, e.g., a modified FGF-21 polypeptide such as PEG-FGF-21, comprising admixing (i) histidine at a concentration between about 15 mM and about 30 mM; (ii) sucrose at a concentration between about 400 mM and about 800 mM; (iii) Polysorbate 80 at a concentration between about 0.04% and about 0.07% (w/v); and, (iv) DTPA at a concentration between about 40 µM and about 70 µM; wherein the pH of the formulation is between about 7 and about 7.2.

The present disclosure provides a method to improve the stability of a formulation comprising a FGF-21 polypeptide, e.g., a modified FGF-21 polypeptide such as PEG-FGF-21, comprising admixing (i) histidine at a concentration between about 15 mM and about 25 mM; (ii) sucrose at a concentration between about 500 mM and about 700 mM; (iii) Polysorbate 80 at a concentration between about 0.04% and about 0.06% (w/v); and, (iv) DTPA at a concentration between about 45 UM and about 55 µM; wherein the pH of the formulation is between about 7 and about 7.1.

The present disclosure also provides a method to improve the stability of a formulation comprising a FGF-21 polypeptide, e.g., a modified FGF-21 polypeptide such as PEG-FGF-21, comprising admixing (i) histidine at a concentration of about 20 mM; (ii) sucrose at a concentration of about 600 mM; (iii) Polysorbate 80 at a concentration of about 0.05% (w/v); and (iv) DTPA at a concentration of about 50 M; wherein the pH is about 7.1.

The present disclosure also provides a method to improve the stability of a formulation comprising a FGF-21 polypeptide, e.g., a modified FGF-21 polypeptide such as PEG-FGF-21, comprising admixing (i) histidine at a concentration of 20 mM; (ii) sucrose at a concentration of 600 mM; (iii) Polysorbate 80 at a concentration of 0.05% (w/v); and (iv) DTPA at a concentration of 50 µM; wherein the pH is 7.1.

The present disclosure provides a method to improve the stability of a formulation comprising a FGF-21 polypeptide, e.g., a modified FGF-21 polypeptide such as PEG-FGF-21, comprising admixing (i) histidine at a concentration of about 20 mM; and (ii) sucrose at a concentration of about 600 mM; wherein the pH is about 7.0.

The present disclosure provides a method to improve the stability of a formulation comprising a FGF-21 polypeptide, e.g., a modified FGF-21 polypeptide such as PEG-FGF-21, comprising admixing (i) histidine at a concentration of 20 mM; and (ii) sucrose at a concentration of 600 mM; wherein the pH is 7.0.

The present disclosure provides a method to improve the stability of a formulation comprising a PEG-FGF-21 (SEQ ID NO: 2) at a concentration of about 10 mg/mL comprising admixing (i) histidine at a concentration of about 20 mM; (ii) sucrose at a concentration of about 600 mM; (iii) Polysorbate 80 at a concentration of about 0.05% (w/v); and (iv) DTPA at a concentration of about 50 µM; wherein the pH is about 7.1.

The present disclosure provides a method to improve the stability of a formulation comprising a PEG-FGF-21 (SEQ ID NO: 2) at a concentration of about 20 mg/mL comprising admixing (i) histidine at a concentration of about 20 mM; (ii) sucrose at a concentration of about 600 mM; (iii) Polysorbate 80 at a concentration of about 0.05% (w/v); and (iv) DTPA at a concentration of about 50 µM; wherein the pH is about 7.1.

The present disclosure provides a method to improve the stability of a formulation comprising a PEG-FGF-21 (SEQ ID NO: 2) at a concentration of about 10 mg/mL comprising admixing (i) histidine at a concentration of 20 mM; (ii) sucrose at a concentration of 600 mM; (iii) Polysorbate 80 at a concentration of 0.05% (w/v); and (iv) DTPA at a concentration of 50 µM; wherein the pH is 7.1.

The present disclosure provides a method to improve the stability of a formulation comprising a PEG-FGF-21 (SEQ ID NO: 2) at a concentration of about 20 mg/mL comprising admixing comprising admixing (i) histidine at a concentration of 20 mM; (ii) sucrose at a concentration of 600 mM; (iii) Polysorbate 80 at a concentration of 0.05% (w/v); and (iv) DTPA at a concentration of 50 µM; wherein the pH is 7.1.

In some embodiments, the concentration of individual excipients included in the pharmaceutical formulation (e.g., DTPA, PS80, Histidine, Sucrose) can be determined/calculated to be the amount (weight, moles etc.) of the individual excipient added to the pharmaceutical formulation in the course of its manufacture per final volume unit of the finished pharmaceutical formulation. In other embodiments, the concentration of excipients included in the pharmaceutical formulation (e.g., DTPA, PS80, Histidine, Sucrose) is based on the actual amount of the individual excipient in the pharmaceutical formulation.

III. Methods of Treatment

The present disclosure also provides methods of treating or preventing a disease or condition associated with fibrosis and/or diabetes in a subject in need thereof comprising administering to the subject an effective amount of a pharmaceutical formulation comprising FGF-21 (e.g., a modified FGF-21 such as PEG-FGF-21) disclosed herein.

In some aspects, the disease or condition is diabetes, e.g., type 2 diabetes. In some aspects, the disease or condition is nonalcoholic steatohepatitis (NASH).

In some aspects, the FGF-21 polypeptide, e.g., a modified FGF-21 polypeptide such as PEG-FGF-21, can be used in the methods of treatment or prevention disclosed herein in an amount between about 1 mg and about 40 mg per dose. In some aspects, the FGF-21 polypeptide, e.g., a modified FGF-21 polypeptide such as PEG-FGF-21, can be used in the methods of treatment or prevention disclosed herein in an amount between about 1 mg and about 5 mg per dose, or between about 5 mg and about 10 mg per dose, or between about 10 mg and about 15 mg per dose, or between about 15 mg and about 20 mg per dose, or between about 20 mg and about 25 mg per dose, or between about 25 mg and about 30 mg per dose, or between about 30 mg and about 35 mg per dose, or between about 35 mg and about 40 mg per dose. In some aspects, the FGF-21 polypeptide, e.g., a modified FGF-21 polypeptide such as PEG-FGF-21, can be used in the methods of treatment or prevention disclosed herein in an amount higher than 40 mg per dose.

In some aspects, the FGF-21 polypeptide, e.g., a modified FGF-21 polypeptide such as PEG-FGF-21, can be used in the methods of treatment or prevention disclosed herein in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg per dose.

In some aspects, the pharmaceutical formulation is administered subcutaneously, e.g., using a safety syringe. In some aspects, the pharmaceutical formulation is administered daily or weekly.

In some aspects, administration of an effective amount of the pharmaceutical formulation comprising FGF-21 (e.g., a modified FGF-21 such as PEG-FGF-21) disclosed herein to the subject decreases liver stiffness, decreases percentage body fat, decreases body weight, decreases liver-to-body weight ratio, decreases liver lipid content, decreases liver fibrosis area, decreases fasting blood glucose levels, decreases fasting triglyceride levels, decreases LDL cholesterol levels, decreases ApoB levels, decreases ApoC levels, increases HDL cholesterol, or any combination thereof.

In some aspects, the administration of the pharmaceutical formulation comprising a FGF-21 polypeptide (e.g., a modified FGF-21 polypeptide such as PEG-FGF-21) disclosed herein according to the methods of treatment disclosed herein to the subject results in (i) reduction in levels of liver fat; (ii) reduction in levels of liver injury; (iii) reduction in levels of fibrosis; (iv) decrease in levels of fibrosis biomarker serum Pro-C3 (N-terminal type III collagen propeptide); (v) decrease in levels of alanine aminotransferase (ALT); (vi) decrease in levels of aspartate aminotransferase (AST); (vii) increase in levels of serum adiponectin; (viii) decrease in levels of plasma LDL; (ix) increase in levels of plasma HDL; (x) decrease in levels of plasma triglyceride; (xi) reduction in level of liver stiffness; or (xii) any combination thereof, compared to the levels in untreated subjects or to the subject prior to the administration of the pharmaceutical formulation.

The present disclosure provides a method of treating a disease associated with fibrosis comprising administering to a subject in need thereof an effective amount of a pharmaceutical formulation comprising an FGF-21 polypeptide disclosed herein. In some aspects, the disease associated with fibrosis may affect an organ or tissue such as the pancreas, lung, heart, kidney, liver, eyes, nervous system, bone marrow, lymph nodes, endomyocardium, and/or retroperitoneum. In some aspects, the disease associated with fibrosis may be liver fibrosis or pre-cirrhosis. In some aspects, the disease associated with fibrosis may be selected from: nonalcoholic steatohepatitis (NASH), cirrhosis, diffuse parenchymal lung disease, cystic fibrosis, pulmonary fibrosis, progressive massive fibrosis, idiopathic pulmonary fibrosis, injection fibrosis, renal fibrosis, chronic kidney disease, diabetic kidney disease, focal segmental glomerulosclerosis, membranous nephropathy, IgA nephropathy, myelofibrosis, heart failure, acute heart failure, chronic heart failure, metabolic heart failure, cardiac fibrosis, cataract fibrosis, cataract, ocular scarring, pancreatic fibrosis, skin fibrosis, intestinal fibrosis, intestinal strictures, endomyocardial fibrosis, atrial fibrosis, mediastinal fibrosis, Crohn's disease, retroperitoneal fibrosis, keloid, nephrogenic systemic fibrosis, scleroderma, systemic sclerosis, arthrofibrosis, Peyronie's syndrome, Dupuytren's contracture, diabetic neuropathy, adhesive capsulitis, alcoholic liver disease, hepatosteatosis, viral hepatitis, biliary disease, primary hemochromatosis, drug-related cirrhosis, cryptogenic cirrhosis, Wilson's disease, and, alpha 1-antitrypsin deficiency, interstitial lung disease (ILD), human fibrotic lung disease, liver fibrosis, macular degeneration, retinal retinopathy, vitreal retinopathy, myocardial fibrosis, Grave's ophthalmopathy, drug induced ergotism, cardiovascular disease, atherosclerosis/restenosis, hypertrophic scars, primary or idiopathic myelofibrosis, and inflammatory bowel disease (including, but not limited to, collagenous colitis). In some aspects, the disease associated with fibrosis results from one or more of pulmonary disease, lung cancer, drug therapy, chemotherapy, or radiation therapy. In some aspects, the disease associated with fibrosis results from one or more of aging, heart attack, stroke, myocardial damage, or left ventricular dysfunction. In some aspects, the disease associated with fibrosis may be selected from renal fibrosis, glomerular nephritis, chronic kidney disease, chronic kidney failure, and nephritis associated with systemic lupus, cancer, physical obstructions, toxins, metabolic disease, immunological diseases, or diabetic nephropathy. In some aspects, the disease associated with fibrosis results from one or more of trauma, spinal injury, infection, surgery, ischemic injury, heart attack, burns, environmental pollutant exposure, pneumonia, tuberculosis, or acute respiratory distress syndrome. In some aspects, the disease associated with fibrosis may be selected from pulmonary fibrosis, interstitial lung disease, human fibrotic lung disease, idiopathic pulmonary fibrosis, liver fibrosis, cardiac fibrosis, myocardial fibrosis, macular degeneration, retinal retinopathy, vitreal retinopathy, Grave's ophthalmopathy, drug induced ergotism, cardiovascular disease, atherosclerosis/restenosis, keloids and hypertrophic scars, primary or idiopathic myelofibrosis, inflammatory bowel disease, collagenous colitis, ocular scarring and cataract fibrosis. In some aspects, the disease associated with fibrosis may be selected from NASH, liver fibrosis, and cirrhosis. In some aspects, the disease associated with fibrosis may be NASH. In some aspects, the disease associated with fibrosis may be selected from diabetic kidney disease, chronic kidney disease, and renal fibrosis. In some aspects, the disease associated with fibrosis may be selected from metabolic heart failure and cardiac fibrosis. In some aspects, the disease associated with fibrosis may be lung fibrosis.

In some aspects, the present disclosure provides a method of decreasing the hepatic fat fraction in a subject in need thereof, comprising administering to the subject an effective amount of a pharmaceutical formulation comprising an FGF-21 polypeptide described herein, wherein optionally the subject is at risk of developing or has been diagnosed with NASH.

In some aspects, the present disclosure provides a method of decreasing liver stiffness, decreasing percentage body fat, decreasing body weight, decreasing liver-to-body weight ratio, decreasing liver lipid content, decreasing liver fibrosis area, decreasing fasting blood glucose levels, fasting triglyceride, decreasing LDL cholesterol, decreasing ApoB, decreasing ApoC, and/or increasing HDL cholesterol in a subject in need thereof, comprising administering to the subject an effective amount of a pharmaceutical formulation comprising an FGF-21 polypeptide described herein, wherein optionally the subject is at risk of developing or has been diagnosed with NASH.

In some aspects, the present disclosure provides a method of increasing adiponectin levels in a subject in need thereof, comprising administering to the subject an effective amount of a pharmaceutical formulation comprising an FGF-21 polypeptide, wherein optionally said subject is at risk of developing or has been diagnosed with NASH.

In some aspects, the present disclosure provides a method of treating one or more symptoms associated with NASH in a subject in need thereof, comprising administering to the subject an effective amount of a pharmaceutical formulation comprising an FGF-21 polypeptide.

Provided herein are also methods of treating or preventing NASH in a subject in need thereof, comprising administering to the subject a therapeutically effective amount of a pharmaceutical formulation disclosed herein comprising a modified FGF-21 polypeptide comprising SEQ ID NO: 1, wherein the pAF residue thereof is linked to a poly(ethylene glycol) moiety with a molecular weight of about 30 kDa (PEG-FGF-21).

In some aspects, the subject may exhibit NASH CRN fibrosis stage 1-3, which optionally is determined by a liver biopsy. In some aspects, prior to treatment the subject may exhibit a fatty liver index of at least about 60. In some aspects, prior to treatment the subject may exhibit a hepatic fat fraction percentage of at least 10%, which optionally is determined by magnetic resonance imaging.

In some aspects, the disclosure provides a method of treating type 1 diabetes or type 2 diabetes in a subject in need thereof, comprising administering to the subject a therapeutically effective amount of a pharmaceutical formulation comprising an FGF-21 polypeptide described herein. In some aspects, the disclosure provides a method of treating obesity in a subject in need thereof, comprising administering to the subject a therapeutically effective amount of a pharmaceutical formulation comprising an FGF-21 polypeptide described herein. In some aspects the disclosure provides a method of regulating at least one of glucose and lipid homeostasis, glucose uptake, GLUT 1 expression, and/or serum concentrations of glucose, triglycerides, insulin or glucagon in a subject in need thereof, comprising administering to the subject an effective amount of a pharmaceutical formulation comprising an FGF-21 polypeptide described herein.

In some aspects, the disclosure provides a method of increasing insulin sensitivity, increasing levels of adiponectin, reducing levels of blood glucose, reducing levels of glucagon, reducing levels of triglyceride, reducing levels of fructosamine, reducing levels of low density cholesterol, or reducing levels of C-reactive protein in a subject in need thereof, comprising administering to the subject an effective amount of a pharmaceutical formulation comprising an FGF-21 polypeptide described herein.

In some aspects the disclosure provides a method of treating a condition or disorder selected from obesity, diabetes, pancreatitis, insulin resistance, hyperinsulinemia, glucose intolerance, hyperglycemia, metabolic syndrome, impaired glucose tolerance, inadequate glucose clearance, high blood glucose, and Prader-Willi syndrome in a subject in need thereof, comprising administering to the subject an effective amount of a pharmaceutical formulation comprising an FGF-21 polypeptide described herein.

In some aspects the disclosure provides a method of treating an insulin related condition or disorder selected from Type A Insulin Resistance, Type C Insulin Resistance (AKA HAIR-AN Syndrome), Rabson-Mendenhall Syndrome, Donohue's Syndrome or Leprechaunism, hyperandrogenism, hirsuitism, or acanthosis nigricans in a subject in need thereof, comprising administering to the subject an effective amount of a pharmaceutical formulation comprising an FGF-21 polypeptide described herein.

In some aspects, the pharmaceutical formulations comprising an FGF-21 polypeptide disclosed herein can be administered or via injection. In some aspects, the pharmaceutical formulations comprising an FGF-21 polypeptide disclosed herein can be administered via subcutaneous injection, IV injection, intraperitoneal injection, or intramuscular injection.

In some aspects, the pharmaceutical formulations comprising an FGF-21 polypeptide disclosed herein can be administered at a frequency of about once per day, or less frequently than about once per day. In some aspects, the pharmaceutical formulations comprising an FGF-21 polypeptide disclosed herein can be administered at a frequency of about twice per week, or less frequently than about twice per week. In some aspects, the pharmaceutical formulations comprising an FGF-21 polypeptide disclosed herein can be administered at a frequency of about once per week, or less frequently than about twice per week. In some aspects, the pharmaceutical formulations comprising an FGF-21 polypeptide disclosed herein can be administered at a frequency of about once per two weeks, or less frequently than about twice per week. In some aspects, the pharmaceutical formulations comprising an FGF-21 polypeptide disclosed herein can be administered at a frequency of about once per three weeks, or less frequently than about twice per week. In some aspects, the pharmaceutical formulations comprising an FGF-21 polypeptide disclosed herein can be administered at a frequency of about once per month, or less frequently than about once per month. In some aspects, the pharmaceutical formulations comprising an FGF-21 polypeptide disclosed herein can be administered at a frequency of once per four weeks. In some aspects, the pharmaceutical formulations comprising an FGF-21 polypeptide disclosed herein can be administered at a frequency of about once per day. In some aspects, the pharmaceutical formulations comprising an FGF-21 polypeptide disclosed herein can be administered at a frequency of about once per week.

In some aspects, the pharmaceutical formulations comprising an FGF-21 polypeptide disclosed herein can be administered in an amount selected from about 1 mg, about 2 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, and about 100 mg of FGF-21 polypeptide per dose.

For example, a pharmaceutical formulation comprising an FGF-21 polypeptide disclosed herein can be administered to a subject at a FGF-21 polypeptide concentration of between about 0.1 and 100 mg/kg of body weight of recipient subject. In some aspects, a pharmaceutical formulation comprising an FGF-21 polypeptide disclosed herein can be administered to a subject at a FGF-21 polypeptide concentration of about 0.5-5 mg/kg of body weight of recipient subject. In another aspect, a pharmaceutical formulation comprising an FGF-21 polypeptide disclosed herein can be administered to a recipient subject with a frequency of between once per day and once per two weeks, such as about once or twice per week, once every two days, once every three days, once every four days, once every five days, or once every six days.

Pharmaceutical formulations of the present disclosure can be administered by any conventional route suitable for proteins or peptides, including, but not limited to parenterally, e.g., injections including, but not limited to, subcutaneously or intravenously or any other form of injections or infusions.

IV. Modified FGF-21 Polypeptides

Modified FGF-21 polypeptides of the present disclosure encompass FGF-21 polypeptides comprising one or more amino acid substitutions, additions or deletions. For example, modified FGF-21 polypeptides of the present disclosure comprise one or more amino acid substitutions (for example with naturally occurring or non-naturally occurring amino acids), deletions (terminal or internal deletions), or modification such as the attachment of a heterologous moiety (C-terminal, N-terminal, or internal, either by intercalation/insertion in the amino acid sequence or by side-chain attachment). In some specific aspects, the modified FGF-21 polypeptide comprises a modified version of SEQ ID NO: 3 (wild type FGF-21), or SEQ ID NO: 1 (wild type sequence modified by substitution of glutamine 109 with para-acetyl-L-phenylalanine). In some specific aspects, the modified FGF-21 polypeptide is a derivative of SEQ ID NO: 1, e.g., via attachment of a heterologous moiety (e.g., PEG). In a specific aspect, the modified FGF-21 is PEG-FGF-21 (SEQ ID NO: 2).

TABLE 1

Sequences of FGF-21 polypeptides

| SEQ ID NO | Description | Sequence |
| --- | --- | --- |
| 1 | Q109 modified FGF-21 | MHPIPDSSPLLQFGGQVRQRYLYTDDAQQTEAHLEIREDGTVGGAADQSP ESLLQLKALKPGVIQILGVKTSRFLCQRPDGALYGSLHFDPEACSFRELL LEDGYNVY(pAF)SEAHGLPLHLPGNKSPHRDPAPRGPARFLPLPGLPPAPPEP PGILAPQPPDVGSSDPLSMVGPSQGRSPSYAS<br>pAF = para-acetyl-L-phenylalanine |
| 2 | PEG-FGF-21 PEGylated Q109 modified FGF-21 | MHPIPDSSPLLQFGGQVRQRYLYTDDAQQTEAHLEIREDGTVGGAADQSP ESLLQLKALKPGVIQILGVKTSRFLCQRPDGALYGSLHFDPEACSFRELL LEDGYNVY(pAF)SEAHGLPLHLPGNKSPHRDPAPRGPARFLPLPGLPPAPPEP PGILAPQPPDVGSSDPLSMVGPSQGRSPSYAS<br>wherein pAF is linked to a 30 kDa PEG |
| 3 | Native FGF-21 | MHPIPDSSPLLQFGGQVRQRYLYTDDAQQTEAHLEIREDGTVGGAADQSP ESLLQLKALKPGVIQILGVKTSRFLCQRPDGALYGSLHFDPEACSFRELL LEDGYNVYQSEAHGLPLHLPGNKSPHRDPAPRGPARFLPLPGLPPAPPEP PGILAPQPPDVGSSDPLSMVGPSQGRSPSYAS<br>The glutamine (Q) modified in SEQ ID NOS:1 and 2 is underlined. |

The term modified FGF-21 polypeptide also encompasses polymorphisms (e.g., naturally occurring FGF-21 sequence variants), e.g, the P-form or L-form of FGF-21.

Substitutions in a wide variety of amino acid positions in naturally-occurring FGF-21 have been described. Substitutions including but not limited to, those that modulate solubility or stability, increase agonist activity, increase in vivo or in vitro half-life, increase protease resistance, convert the polypeptide into an antagonist, reduce immunogenicity or toxicity, facilitate purification or manufacturability, or any combination thereof, and are also encompassed by the term modified FGF-21 polypeptide.

In some cases, the non-naturally encoded amino acid substitution(s) may be combined with other additions, substitutions or deletions within the modified FGF-21 polypeptide to affect other biological traits of the modified FGF-21 polypeptide relative to another FGF-21 polypeptide (e.g., the wild-type FGF-21 polypeptide of SEQ ID NO: 3, the modified FGF-21 polypeptide of SEQ ID NO: 1, the PEG-FGF-21 polypeptide of SEQ ID NO: 2, the same FGF-21 polypeptide without the addition, substitution, or deletion, or another unmodified or modified FGF-21 unmodified or modified polypeptide).

In some cases, the other additions, substitutions or deletions may increase the stability (including but not limited to, resistance to proteolytic degradation) of the modified FGF-21 polypeptide or increase affinity of the modified FGF-21 polypeptide for its receptor. In some cases, the other additions, substitutions or deletions may increase the pharmaceutical stability of the modified FGF-21 polypeptide. In some cases, the other additions, substitutions or deletions may increase the solubility of the modified FGF-21 polypeptide.

In some aspects, sites are selected for substitution with a naturally encoded or non-natural amino acid in addition to another site for incorporation of a non-natural amino acid that results in increasing the polypeptide solubility following expression in a recombinant host cell.

In some aspects, the modified FGF-21 polypeptides comprise another addition, substitution or deletion that modulates affinity for the FGF-21 polypeptide receptor, binding proteins, or associated ligand, modulates signal transduction after binding to the FGF-21 receptor, modulates circulating half-life, modulates release or bio-availability, facilitates purification, or improves or alters a particular route of administration.

In some aspects, the modified FGF-21 polypeptides comprise an addition, substitution or deletion that increases the affinity of the modified FGF-21 for its receptor. Similarly, modified FGF-21 polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, modified FGF-21 size reduction, or other traits of the polypeptide.

Multiple polymorphisms of FGF-21 have been identified. Leucine or proline have been described at the same position in U.S. Patent Publication No. 20010012628 and U.S. Pat. No. 6,716,626. N-terminal leader or signal sequences that differ by 1 amino acid (leucine) are shown in U.S. Pat. No. 6,716,626 and U.S. Patent Publication No. 20040259780. FGF-21 polypeptide variants or mutants include, but are not limited to, those disclosed in U.S. Pat. No. 6,716,626; U.S. Patent Publication Nos. 2005/0176631, 2005/0037457, 2004/0185494, 2004/0259780, 2002/0164713, and 2001/0012628; WO 01/36640; WO 03/011213; WO 03/059270; WO 04/110472; WO 05/061712; WO 05/072769; WO 05/091944; WO 05/113606; WO 06/028595; WO 06/028714; WO 06/050247; WO 06/065582; WO 06/078463; WO01/018172; WO09/149171; WO10/042747; WO12/066075; WO11/154349; WO13/052311; WO13/188181, which are incorporated by reference in their entirety herein.

The term modified FGF-21 polypeptide also includes biologically-active fragments, biologically active variants and stereoisomers of the naturally-occurring FGF-21 as well as agonist, mimetic, and antagonist variants of the naturally-occurring FGF-21 and polypeptide fusions thereof. Fusions comprising additional amino acids at the amino terminus, carboxyl terminus, or both, are encompassed by the term modified FGF-21 polypeptide.

Exemplary fusions include, but are not limited to, e.g., methionyl FGF-21 in which a methionine is linked to the N-terminus of FGF-21 resulting from the recombinant expression of the mature form of FGF-21 lacking the leader or signal peptide or portion thereof (a methionine is linked to the N-terminus of FGF-21 resulting from the recombinant expression, e.g. in E. coli), fusions for the purpose of purification (including, but not limited to, to poly-histidine or affinity epitopes), fusions with serum albumin binding peptides such as PKE adnectin and fusions with serum proteins such as serum albumin, and fusion proteins comprising FGF-21 and one or more other molecules (heterologous moieties), including but not limited to, serum albumin, Fc domain, immunoglobulin constant region, unstructured polypeptides such as XTEN, etc. Any such fragments can be prepared from the proteins by standard biochemical methods, or by expressing a polynucleotide encoding the fragment.

The term modified FGF-21 polypeptide includes polypeptides conjugated to a polymer such as PEG and may optionally comprise one or more additional derivatizations of cysteine, lysine, or other residues. In addition, the modified FGF-21 polypeptide may comprise a linker or polymer, wherein the amino acid to which the linker or polymer is conjugated may be a non-natural amino acid according to the present disclosure, or may be conjugated to a naturally encoded amino acid utilizing techniques known in the art such as coupling to lysine or cysteine.

The term modified FGF-21 polypeptide also includes glycosylated modified FGF-21, such as but not limited to, polypeptides glycosylated at any amino acid position, N-linked or O-linked glycosylated forms of the polypeptide. Variants containing single nucleotide changes are also considered as biologically active variants of FGF-21 polypeptide. In addition, splice variants are also included.

The term modified FGF-21 polypeptide also includes FGF-21 polypeptide heterodimers, homodimers, heteromultimers, or homomultimers of any one or more unmodified or modified FGF-21 polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

The term modified FGF-21 polypeptide also encompasses FGF-21 polypeptides comprising one or more amino acid substitutions, insertions or deletions. For example, modified FGF-21 polypeptides of the present disclosure may be comprised of modifications with one or more natural amino acids, optionally in conjunction with one or more non-natural amino acid modification. Exemplary substitutions, insertions or deletions in a wide variety of amino acid positions in FGF-21 polypeptides, including but not limited to substitutions that modulate pharmaceutical stability, that modulate one or more of the biological activities of the FGF-21 polypeptide, such as but not limited to, increase agonist activity, increase solubility of the polypeptide, decrease protease susceptibility, decrease deamidation, convert the polypeptide into an antagonist, reduce immunogenicity or toxicity, or facilitate purification or manufacturability, etc. are encompassed by the term modified FGF-21 polypeptide.

In some aspects, the modified FGF-21 polypeptides further comprise an additional insertion, substitution or deletion that modulates biological activity of the modified FGF-21 polypeptide. For example, the additions, substitutions or deletions may modulate one or more properties or activities of modified FGF-21. For example, the additions, substitutions or deletions may modulate affinity for the FGF-21 polypeptide receptor, modulate circulating half-life, modulate therapeutic half-life, modulate stability of the polypeptide, modulate cleavage by proteases, modulate dose, modulate release or bio-availability, facilitate purification, decrease deamidation, improve shelf-life, or improve or alter a particular route of administration. Similarly, modified FGF-21 polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term modified FGF-21 polypeptide also encompasses homodimers, heterodimers, homomultimers, and heteromultimers that are formed via fusion partners, such as Fc domains, or that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly (ethylene glycol) or polydextran, or polypeptides of various lengths.

In some aspects, a non-naturally encoded amino acid described herein may comprise a carbonyl group, an aminooxy group, a hydrazide group, a hydrazine group, a semicarbazide group, an azide group, or an alkyne group. In some aspects, the non-naturally encoded amino acid comprises a carbonyl moiety and is linked to a linker, polymer, biologically active molecule, or half-life extending moiety comprising an aminooxy, a hydrazine, a hydrazide or a semicarbazide moiety. In some aspects, the non-naturally encoded amino acid comprises an aminooxy, hydrazine, hydrazide or semicarbazide moiety which is linked to a linker, polymer, biologically active molecule, or half-life extending moiety through an amide linkage.

In some aspects, the non-naturally encoded amino acid comprises an alkyne moiety which is linked to a linker, polymer, biologically active molecule, or half-life extending moiety via an azide moiety. In some aspects, the non-naturally encoded amino acid comprises an azide moiety which is linked to a linker, polymer, biologically active molecule, or half-life extending moiety comprising an alkyne moiety. In some the, the one non-naturally encoded amino acid comprises an azide or alkyne moiety which is linked to a linker, polymer, biologically active molecule, or half-life extending moiety through an amide linkage.

In some aspects, the non-naturally encoded amino acid is linked to a linker, polymer, biologically active molecule, or half-life extending moiety through an oxime linkage. In some aspects, the non-naturally encoded amino acid is linked to a linker, polymer, biologically active molecule, or half-life extending moiety through an oxime linkage, wherein said oxime linkage has the structure resulting from the reaction of a carbonyl group and aminooxy group. In some aspects, the non-naturally encoded amino acid is linked to a linker, polymer, biologically active molecule, or half-life extending moiety through an oxime linkage, wherein said oxime linkage has the structure resulting from the reaction of a carbonyl group contained in said non-naturally encoded amino acid and aminooxy group contained in said linker, polymer, biologically active molecule, or half-life extending moiety.

In some aspects, the modified FGF-21 polypeptide described herein possesses at least one biological activity of the wild-type human FGF-21 polypeptide having the amino acid sequence of SEQ ID NO: 3.

In some aspects, the modified FGF-21 polypeptide comprises at least one non-naturally encoded amino acids linked to a water soluble polymer comprising a poly(ethylene glycol) moiety. In some aspects, one or more non-naturally encoded amino acids are incorporated in one or more of the following positions in modified FGF-21: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (amino acid positions corresponding to SEQ ID NO: 3).

In some aspects, the FGF-21 polypeptide in a pharmaceutical formulation disclosed herein is a modified FGF-21 polypeptide described, for example, in U.S. Pat. Nos. 9,273,106; 9,458,214; 9,744,213; 8,541,369; 8,188,040; 9,120,871; 9,895,417; 9,266,935; 6,716,626; 4,904,584; or 8,722,622; U.S. Appl. Publ. No. 2013/0231277; 2009/0305986; 2011/0195895; 2010/0216715; 2001/0012628; 2004/0259780; 2005/0176631; 20070293430; or 2012/0035099; or PCT Publ. Nos. WO2016048999; WO2010065439; WO2017093465; WO2003011213; WO2003059270; WO2005091944; WO2008121563; WO199967291, WO199903887, WO200026354; or WO2017220706; all of which are herein incorporated by reference in their entireties.

V. Half-Life Extending Moieties

The FGF-21 polypeptides of the present disclosure can comprise a heterologous moiety, which in some aspect is a half-life extending moiety. In some aspects, the half-life extending moiety is a polypeptide moiety, whereas in some other aspects the half-life extending moiety is a non-polypeptide moiety. In some aspects, the FGF-21 polypeptide comprises a single half-life extending moiety. However, in other aspects, a FGF-21 polypeptide disclosed herein can comprise more than one half-life extending moiety.

Half-life extending moieties includes non-proteinaceous and proteinaceous half-life extending moieties. Non-proteinaceous half-life extending moieties include, e.g., water soluble polymers such as polyethylene glycol (PEG), hydroxyethyl starch (HES), lipids, branched or unbranched acyl groups, branched or unbranched $C_8$-$C_{30}$ acyl groups, branched or unbranched alkyl groups, and a branched or unbranched $C_8$-$C_{30}$ alkyl groups. Proteinaceous half-life extending moieties include, e.g., serum albumin, transferrin, adnectins (e.g., albumin-binding or pharmacokinetics extending (PKE) adnectins), Fc domains, and unstructured polypeptides, such as XTEN and PAS (e.g. conformationally disordered polypeptide sequences composed of the amino acids Pro, Ala, and/or Ser), as well as a fragment of any of the foregoing.

An examination of the crystal structure of FGF-21 or FGF family member(s) and its interaction with the FGF receptor can indicate which certain amino acid residues have side chains that are fully or partially accessible to solvent. The side chain of a non-naturally encoded amino acid at these positions may point away from the protein surface and out into the solvent and thus be linked to, e.g., a water soluble polymer.

(a) Immunoglobulin Constant Region or Portion Thereof

In some aspects, the FGF-21 polypeptide is linked, e.g., fused or conjugated, to an immunoglobulin constant region or a portion thereof. An immunoglobulin constant region is comprised of domains denoted CH (constant heavy) domains (CH1, CH2, etc.). Depending on the isotype, (i.e.

IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the fusion protein of the present disclosure may be obtained from a number of different sources. In some aspects, an immunoglobulin constant region or a portion thereof is derived from a human immunoglobulin. It is understood, however, that the immunoglobulin constant region or a portion thereof may be derived from an immunoglobulin of another mammalian species, including for example, a rodent (e.g. a mouse, rat, rabbit, guinea pig) or non-human primate (e.g. chimpanzee, macaque) species. Moreover, the immunoglobulin constant region or a portion thereof may be derived from any immunoglobulin class, including IgM, IgG, IgD, IgA and IgE, and any immunoglobulin isotype, including IgG1, IgG2, IgG3 and IgG4. In one aspect, the human isotype IgG1 is used.

A variety of the immunoglobulin constant region gene sequences (e.g. human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present disclosure. It will further be appreciated that the scope of this disclosure encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, CA (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995.

An immunoglobulin constant region used herein can include all domains and the hinge region or portions thereof. In one aspect, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native immunoglobulin, i.e., as formed by the dimeric association of the respective Fc domains of its two heavy chains. A native Fc region forms a homodimer with another Fc region.

In one aspect, the "Fc region" refers to the portion of a single immunoglobulin heavy chain beginning in the hinge region just upstream of the papain cleavage site (i.e. residue 216' in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an immunoglobulin constant region, depending on the immunoglobulin isotype can include the CH2, CH3, and CH4 domains, as well as the hinge region. Fusion proteins comprising an Fc region of an immunoglobulin bestow several desirable properties on a fusion protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1).

In some aspects, the "Fc region" includes an amino acid sequence of an Fc domain or derived from an Fc domain. In certain aspects, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other aspects, an Fc region comprises a complete Fc domain (i.e., a hinge domain, a CH2 domain, and a CH3 domain). In some aspects, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other aspects, an Fc region lacks at least a portion of a CH2 domain (e.g., all or part of a CH2 domain). In a particular aspect, an Fc region comprises or consists of amino acids corresponding to EU numbers 221 to 447.

The Fc domains denoted as F, F1, or F2 herein may be obtained from a number of different sources. In one aspect, an Fc region of the polypeptide is derived from a human immunoglobulin. It is understood, however, that an Fc region may be derived from an immunoglobulin of another mammalian species, including for example, a rodent (e.g., a mouse, rat, rabbit, guinea pig) or non-human primate (e.g., chimpanzee, macaque) species. Moreover, the polypeptide of the Fc domains or portions thereof may be derived from any immunoglobulin class, including IgM, IgG, IgD, IgA and IgE, and any immunoglobulin isotype, including IgG1, IgG2, IgG3 and IgG4. In another aspect, the human isotype IgG1 is used.

In certain aspects, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other aspects, the Fc variant provides an engineered cysteine residue.

The Fc regions of the disclosure may employ art-recognized Fc variants which are known to impart a change (e.g., an enhancement or reduction) in effector function and/or FcR binding. Specifically, a binding molecule of the disclosure may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/063351A2, WO04/016750A2, WO04/029207A2, WO04/035752A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US2007/0248603, US2007/0286859, US20080057056; or U.S. Pat. Nos. 5,648,260; 5,739,277; 5,834,250; 5,869,046; 6,096,871; 6,121,022; 6,194,551; 6,242, 195; 6,277,375; 6,528,624; 6,538,124; 6,737,056; 6,821,505; 6,998,253; 7,083,784; 7,404,956, and 7,317,091. In one aspect, the specific change (e.g., the specific substitution of one or more amino acids disclosed in the art) may be made at one or more of the disclosed amino acid positions. In another aspect, a different change at one or more of the disclosed amino acid positions (e.g., the different substitution of one or more amino acid position disclosed in the art) may be made.

The Fc region of IgG can be modified according to well recognized procedures such as site directed mutagenesis and the like to yield modified IgG or Fc fragments or portions thereof that will be bound by Fc receptors. Such modifications include modifications remote from the Fc receptor contact sites as well as modifications within the contact sites that preserve or even enhance binding to the Fc receptors. For example, the following single amino acid residues in human IgG1 Fc (Fc γ1) can be substituted without significant loss of Fc binding affinity for Fc receptors: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific aspect incorporates the N297A mutation, removing a highly conserved N-glycosylation site. In addition to alanine other amino acids may be substituted for the wild type amino acids at the positions specified above. Mutations may be introduced into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the disclosure may be mutated and the other Fc region of the construct not mutated at all, or they both may be mutated but with different mutations.

Certain of the above mutations may confer new functionality upon the Fc region. For example, one aspect incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for Fc receptors may be increased beyond that of wild type in some instances. This increased affinity may reflect an increased "on" rate, a decreased "off" rate or both an increased "on" rate and a decreased "off" rate. Examples of mutations believed to impart an increased affinity for Fc receptors include, but are not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRII, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In certain aspects, the immunoglobulin constant region or a portion thereof is hemi-glycosylated. For example, the fusion protein comprising two Fc regions or FcRn binding partners may contain a first, glycosylated, Fc region (e.g., a glycosylated CH2 region) and a second, aglycosylated, Fc region (e.g., an aglycosylated CH2 region). In one aspect, a linker may be interposed between the glycosylated and aglycosylated Fc regions. In another aspect, the Fc region or FcRn binding partner is fully glycosylated, i.e., all of the Fc regions are glycosylated. In other aspects, the Fc region may be aglycosylated, i.e., none of the Fc moieties are glycosylated.

In certain aspects, a fusion protein of the disclosure comprises an amino acid substitution to an immunoglobulin constant region or a portion thereof (e.g., Fc variants), which alters the antigen-independent effector functions of the Ig constant region, in particular the circulating half-life of the protein.

Such proteins exhibit either increased or decreased binding to an Fc receptor when compared to proteins lacking these substitutions and, therefore, have an increased or decreased half-life in serum, respectively. Fc variants with improved affinity for an Fc receptor are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased Fc receptor binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased Fc receptor binding affinity are also less likely to cross the placenta and, thus, are also useful in the treatment of diseases or disorders in pregnant women.

In addition, other applications in which reduced Fc receptor binding affinity may be desired include those applications in which localization the brain, kidney, and/or liver is desired. In one exemplary aspect, the fusion protein of the disclosure exhibit reduced transport across the epithelium of kidney glomeruli from the vasculature. In another aspect, the fusion protein of the disclosure exhibit reduced transport across the blood brain barrier (BBB) from the brain, into the vascular space. In one aspect, a protein with altered Fc receptor binding comprises at least one Fc region (e.g., one or two Fc regions) having one or more amino acid substitutions within the "Fc receptor binding loop" of an Ig constant region. The Fc receptor binding loop is comprised of amino acid residues 280-299 (according to EU numbering) of a wild-type, full-length, Fc region.

In other aspects, an Ig constant region or a portion thereof of the disclosure having altered Fc receptor binding affinity comprises at least one Fc region having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered Fc receptor binding activity are disclosed in International PCT Publication No. WO05/047327.

(b) Albumin or Fragment, or Variant Thereof

In some aspects, the FGF-21 polypeptide is linked, e.g., fused or conjugated, to albumin or a functional fragment thereof.

Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof.

In some aspects, the half-life extension moiety linked to the FGF-21 polypeptide is albumin or a fragment or variant thereof, which extends (or is capable of extending) the half-life of the FGF-21 polypeptide. Further examples of albumin or the fragments or variants thereof are disclosed in US Pat. Publ. Nos. 2008/0194481 A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2.

(c) Albumin Binding Moiety

In certain aspects, the half-life extension moiety linked, e.g., fused or conjugated, to the FGF-21 polypeptide is an albumin binding moiety, which comprises an albumin binding peptide, a bacterial albumin binding domain, an albumin-binding antibody fragment, or any combinations thereof. For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) J. Immunol. Methods 218, 73-83). Other examples of albumin binding peptides that can be used as conjugation partner are, for instance, those having a Cys-Xaa 1-Xaa 2-Xaa 3-Xaa 4-Cys consensus sequence, wherein Xaa 1 is Asp, Asn, Ser, Thr, or Trp; Xaa 2 is Asn, Gln, H is, Ile, Leu, or Lys; Xaa 3 is Ala, Asp, Phe, Trp, or Tyr; and Xaa 4 is Asp, Gly, Leu, Phe, Ser, or Thr as described in US patent application 2003/0069395 or Dennis et al. (Dennis et al. (2002) J. Biol. Chem. 277, 35035-35043).

(d) PAS Sequence

In other aspects, the half-life extension moiety linked, e.g., fused or conjugated, to the FGF-21 polypeptide is a PAS sequence. A "PAS sequence," as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the fusion protein. Yet, the skilled person is aware that an amino acid polymer also may form random coil conformation when residues other than alanine, serine, and proline are added as a minor constituent in the PAS sequence. The term "minor constituent" as used herein means that amino acids other than alanine, serine, and proline may be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline may be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the FGF-21 polypeptide. Since the random coil domain does not adopt a stable structure or function by itself, the biological activity mediated by the FGF-21 is essentially preserved. In other aspects, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Exemplary PAS sequences are provided, e.g., in US Pat. Publ. No. 2010/0292130 A1 and PCT Appl. Publ. No. WO 2008/155134 A1, both of which are incorporated by reference in their entireties.

(e) HAP Sequence

In certain aspects, the half-life extension moiety linked, e.g., fused or conjugated, to the FGF-21 polypeptide is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length.

In one aspect, the HAP sequence is capable of extending half-life of a moiety fused to or linked to the HAP sequence.

Non-limiting examples of the HAP sequence includes, but are not limited to (Gly)n, (Gly4Ser)n or S (Gly4Ser)n, wherein n is 1, 2, 3, 4, 5, 6, 7, 8, 9, 10, 11, 12, 13, 14, 15, 16, 17, 18, 19, or 20. In one aspect, n is 20, 21, 22, 23, 24, 25, 26, 26, 28, 29, 30, 31, 32, 33, 34, 35, 36, 37, 38, 39, or 40. In another aspect, n is 50, 60, 70, 80, 90, 100, 110, 120, 130, 140, 150, 160, 170, 180, 190, or 200.

(f) Transferrin or Fragment Thereof

In certain aspects, the half-life extension moiety linked, e.g., fused or conjugated, to the FGF-21 polypeptide is transferrin or a fragment thereof. Any transferrin may be used to make the fusion proteins of the disclosure. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/). Transferrin comprises two domains, N domain and C domain. N domain comprises two subdomains, N1 domain and N2 domain, and C domain comprises two subdomains, C1 domain and C2 domain.

In one aspect, the transferrin portion of the fusion protein includes a transferrin splice variant. In one example, a transferrin splice variant can be a splice variant of human transferrin, e.g., Genbank Accession AAA61140. In another aspect, the transferrin portion of the fusion protein includes one or more domains of the transferrin sequence, e.g., N domain, C domain, N1 domain, N2 domain, C1 domain, C2 domain or any combinations thereof.

(g) Polymer, e.g., Polyethylene Glycol (PEG)

In other aspects, the half-life extension moiety linked, e.g., fused or conjugated, to the FGF-21 polypeptide is a soluble polymer known in the art, including, but not limited to, polyethylene glycol (PEG), ethylene glycol/propylene glycol copolymers, carboxymethylcellulose, dextran, or polyvinyl alcohol. Chemically modified derivatives of the FGF-21 polypeptides of the disclosure can provide additional advantages such as increased solubility, stability and circulating time of the polypeptide, or decreased immunogenicity (see U.S. Pat. No. 4,179,337). The soluble polymer can be attached to any positions within the FGF-21 polypeptide or its N- or C-terminus. The soluble polymer can be attached at random positions within the FGF-21 polypeptide sequence or at predetermined positions within the FGF-21 polypeptide and may include one, two, three or more attached soluble polymer moieties. In some aspects, the polymer is attached to a side chain of a naturally occurring amino acid. In other aspects, the polymer is attached to a side chain of a non-naturally encoded amino acid, e.g., a phenylalanine derivative such as para-acetyl-L-phenylalanine.

The soluble polymer can be of any molecular weight, and can be branched or unbranched. For PEG, in one aspect, the molecular weight is between about 1 kDa and about 100 kDa for ease in handling and manufacturing. In some aspects, the molecular weight of the soluble polymer, e.g., PEG, is about 30 kDa. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the PEG may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 Da.

In some aspects, the PEG may have a branched structure. Branched PEGs are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999).

The number of PEG moieties attached to the FGF-21 polypeptide may also vary. For example, the PEGylated proteins of the disclosure may be linked, on average, to 1, 2, 3, 4, 5, 6, 7, 8, 9, 10, 12, 15, 17, 20, or more PEG molecules. Similarly, the average degree of substitution may lie within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 PEG moieties per protein molecule. Methods for determining the degree of substitution are disclosed, for example, in Delgado et al., Crit. Rev. Thera. Drug Carrier Sys. 9:249-304 (1992).

In other aspects, the FGF-21 polypeptide used in the formulations of the present disclosure is conjugated to one or more polymers. The polymer can be water-soluble and covalently or non-covalently attached to the FGF-21 polypeptide or other moieties conjugated to the FGF-21 polypeptide. Non-limiting examples of the polymer can be poly(alkylene oxide), poly(vinyl pyrrolidone), poly(vinyl alcohol), polyoxazoline, or poly(acryloylmorpholine).

(h) Hydroxyethyl Starch (HES)

In certain aspects, the half-life extension moiety linked, e.g., fused or conjugated, to the FGF-21 polypeptide is hydroxyethyl starch (HES) or a derivative thereof. HES is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., Krankenhauspharmazie, 8 (8), 271-278 (1987); and Weidler et al., Arzneim.-Forschung/Drug Res., 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., Krankenhauspharmazie, 8 (8), 271-278 (1987), as cited above, in particular p. 273.

In one aspect, HES has a mean molecular weight (weight mean) of from 1 to 300 kD, from 2 to 200 kD, from 3 to 100 kD, or from 4 to 70 kD. hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific aspect, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. The characteristics of VOLUVEN® are a mean molecular weight of 130,000+/−20,000 D, a molar substitution of 0.4 and a C2: C6 ratio of about 9:1. In other aspects, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other aspects, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain aspects, the half-life extending moiety can be a mixture of HES having different mean molecular weights and/or different degrees of substitution and/or different ratios of C2: C6 substitution. Therefore, mixtures of HES may be employed having different mean molecular weights and different degrees of substitution and different ratios of C2: C6 substitution, or having different mean molecular weights and different degrees of substitution and the same or about the same ratio of C2: C6 substitution, or having different mean molecular weights and the same or about the same degree of substitution and different ratios of C2: C6 substitution, or having the same or about the same mean molecular weight and different degrees of substitution and different ratios of C2: C6 substitution, or having different mean molecular weights and the same or about the same degree of substitution and the same or about the same ratio of C2: C6 substitution, or having the same or about the same mean molecular weights and different degrees of substitution and the same or about the same ratio of C2: C6 substitution, or having the same or about the same mean molecular weight and the same or about the same degree of substitution and different ratios of C2: C6 substitution, or having about the same mean molecular weight and about the same degree of substitution and about the same ratio of C2: C6 substitution.

(i) Polysialic Acids (PSA)

In certain aspects, the half-life extension moiety linked, e.g., fused or conjugated, to the FGF-21 polypeptide is a polysialic acid (PSA) or a derivative thereof. PSAs are naturally occurring unbranched polymers of sialic acid produced by certain bacterial strains and in mammals in certain cells Roth J., et al. (1993) in Polysialic Acid: From Microbes to Man, eds Roth J., Rutishauser U., Troy F. A. (Birkhäuser Verlag, Basel, Switzerland), pp 335-348. They can be produced in various degrees of polymerization from n=about 80 or more sialic acid residues down to n=2 by limited acid hydrolysis or by digestion with neuraminidases, or by fractionation of the natural, bacterially derived forms of the polymer.

The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist-such as the alternating alpha-2,8 alpha-2,9 polysialic acid of *E. coli* strain K92 and group C polysaccharides of *N. meningitidis*. Sialic acid may also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during fetal development (wherein the polymer has an anti-adhesive function) Cho and Troy, P.N.A.S., USA, 91 (1994) 11427-11431, although there are no known receptors for polysialic acids in mammals. The alpha-2,8-linked polysialic acid of *E. coli* strain K1 is also known as 'colominic acid' and is used (in various lengths) to exemplify the present disclosure.

Various methods of attaching or conjugating polysialic acids to a polypeptide have been described (for example, see U.S. Pat. No. 5,846,951; WO-A-0187922, and US 2007/0191597 A1.

(j) XTEN Sequences

In some aspects, the half-life extension moiety linked, e.g., fused or conjugated, to the FGF-21 polypeptide is an XTEN sequence. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a fusion protein partner, XTENs can serve as a carrier, conferring certain desirable pharmacokinetic, physicochemical and pharmaceutical properties when linked to the FGF-21 polypeptide to create a fusion protein. Such desirable properties include but are not limited to enhanced pharmacokinetic parameters and solubility characteristics.

In some aspects, the XTEN sequence of the disclosure is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain aspects, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues.

The XTEN sequence of the disclosure can comprise one or more sequence motif of 9 to 14 amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids selected from the group consisting of glycine (G), alanine (A), serine(S), threonine (T), glutamate (E) and proline (P). See US 2010-0239554 A1.

In some aspects, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology. In other aspects, the XTEN comprises multiple units of motif sequences from two or more of the motif families. These sequences can be selected to achieve desired physical/chemical characteristics, including such properties as net charge, hydrophilicity, lack of secondary structure, or lack of repetitiveness that are conferred by the amino acid composition of the motifs, described more fully below. In other aspects, the motifs incorporated into the XTEN can be selected and assembled using the methods described herein to achieve an XTEN of about 36 to about 3000 amino acid residues.

In further aspects, the XTEN sequence used in the disclosure affects the physical or chemical property, e.g., pharmacokinetics, of the fusion protein of the present disclosure. The XTEN sequence used in the present disclosure can exhibit one or more of the following advantageous properties: conformational flexibility, enhanced aqueous solubility, high degree of protease resistance, low immunogenicity, low binding to mammalian receptors, or increased hydrodynamic (or Stokes) radii.

In some aspects, a XTEN sequence linked to an FGF-21 polypeptide can increase pharmacokinetic properties such as longer terminal half-life or increased area under the curve (AUC), so that the FGF-21 polypeptide stays in vivo for an increased period of time compared to a corresponding FGF-21 polypeptide without an XTEN. In further aspects, an XTEN sequence linked to an FGF-21 polypeptide disclosed herein can increase pharmacokinetic properties such as longer terminal half-life or increased area under the curve (AUC), so that the FGF-21 polypeptide stays in vivo for an increased period of time compared to a corresponding FGF-21 polypeptide without an XTEN.

A variety of methods and assays can be employed to determine the physical/chemical properties of proteins comprising the XTEN sequence. Such methods include, but are not limited to analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Amau et al., Prot Expr and Purif 48, 1-13 (2006).

Additional examples of XTEN sequences that can be used according to the present disclosure and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, all of which are herein incorporated by reference in their entireties.

(k) Immunoglobulin Binding Peptide (or Polypeptide)

In certain aspects, the half-life extension moiety linked, e.g., fused or conjugated, to the FGF-21 polypeptide is an immunoglobulin binding peptide. The immunoglobulin binding peptides can bind to an Fc region and can improve a half-life of the fusion protein described herein.

In some aspects, the immunoglobulin binding peptide useful for the disclosure is a peptide or a polypeptide having greater than about 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, or 500 amino acid residues.

In some aspects, the immunoglobulin binding peptide useful for the disclosure comprises a 13-mer IgG-Fc domain binding peptide (IgGBP). DeLano W L, et al. (2000) Science 287:1279-1283. In other aspects, the immunoglobulin binding peptide useful for the disclosure comprises the peptides disclosed in US Patent Publication No. 20170334954, US Patent Publication No. 20170210777, or PCT Publication No. WO/2017/069158.

VI. Articles of Manufacture and Kits

The present disclosure also provides an article or manufacture or kit comprising (i) a FGF-21 pharmaceutical formulation comprising a FGF-21 polypeptide (e.g., a modified FGF-21 such as PEG-FGF-21) disclosed herein, and (ii) instructions for use. The article of manufacture can comprise a container. Suitable containers include, for example, bottles, vials, syringes and test tubes. The container may be formed from a variety of materials such as glass, plastic or metals. The container holds the FGF-21 pharmaceutical formulation, e.g., a liquid formulation.

The label on, or associated with, the container may indicate directions for reconstitution and/or use. For example, the label may indicate that the FGF-21 pharmaceutical formulation is to be diluted to protein concentrations as described above. The label may further indicate that the subcutaneous formulation is useful or intended for subcutaneous administration.

The container holding the formulation may be a multi-use vial, which allows for repeat administrations (e.g., from 2 to 6 administrations, or more) of, for example, the subcutaneous formulation. Alternatively, the container may be a pre-filled syringe containing, for example, the subcutaneous formulation.

The article of manufacture or kit may further comprise a second container comprising, for example, a solvent. The article of manufacture may further include other materials desirable from a commercial and user standpoint, including other buffers, diluents, filters, needles, syringes, and package inserts with instructions for use.

It is to be appreciated that the Detailed Description section, and not the Summary and Abstract sections, is intended to be used to interpret the claims. The Summary and Abstract sections may set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

EXAMPLES

Example 1

PEG-FGF-21 Formulation Development

For initial studies, PEG-FGF-21 was formulated at 7.5 mg/mL in 20 mM Tris, 250 mM sucrose, pH 8.3. High deamidation rates observed in this formulation made it necessary to store the drug product frozen at −20° C. Therefore, additional work was performed to develop a ready-to use (RTU) formulation allowing 2-8° C. storage of the drug product.

PEG-FGF-21 (SEQ ID NO: 2) was made by attaching a linear 30-kDa PEG moiety to modified FGF-21 (SEQ ID NO: 1) in a site-specific manner. To achieve site-specific PEGylation, activated PEG was reacted by methods known in the art with the non-natural amino acid, para-acetyl phenylalanine (pAF), in position 109 of the FGF-21 molecule to form a chemically stable oxime-linked PEG-protein conjugate.

Lower formulation pH was shown to increase aggregation rates of the molecule, while higher formulation pH was shown to increase deamidation rates. At the target protein concentration of 10 mg/mL, pH 7.0 was found to be the best balance between aggregation and deamidation rates. Increasing sucrose concentration was shown to further stabilize the molecule against aggregation.

The formulation chosen for further studies was 10 mg/mL PEG-FGF-21 in 20 mM L-histidine, 600 mM sucrose, pH 7.0. Given a contemplated weekly dose of 20 mg, a higher concentration drug product in a pre-filled syringe was developed. To enable the higher concentration drug product, further optimization of the formulation was necessary.

Figure 5:
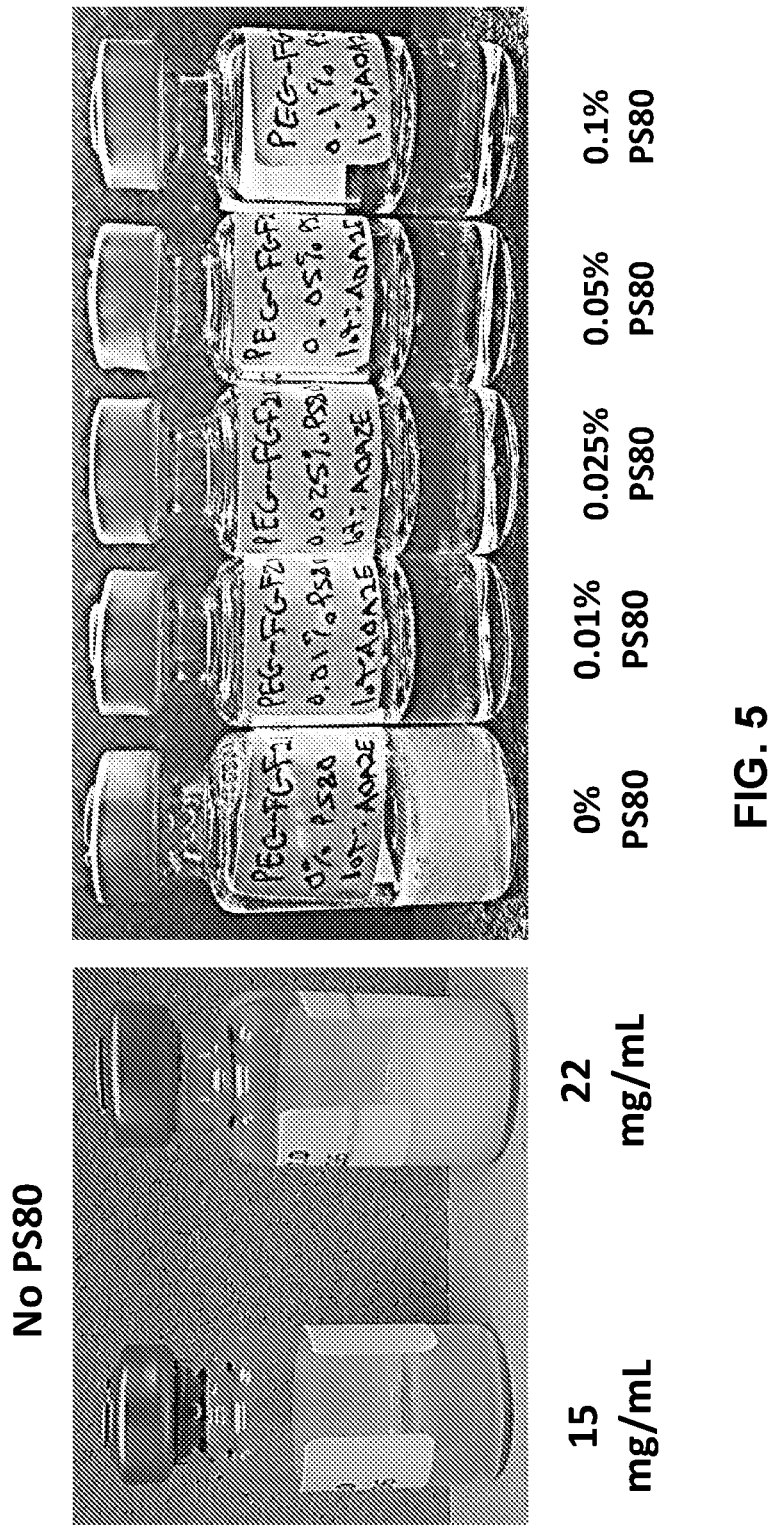
FIG. 5 shows that PEG-FGF-21 at higher concentration without PS80 turned cloudy after 300 rpm orbital shaker 24 h (left) or wrist action shaking for 6 h (right). Addition of polysorbate 80 between 0.01% and 0.1% (w/v) reduced the cloudiness of the samples.

Initial development of a higher concentration formulation was conducted in 3 mL type I glass vials. Upon agitation of 15 mg/mL and 22 mg/mL PEG-FGF-21 in 20 mM L-histidine, 600 mM sucrose, pH 7.0 air bubble entrapment was observed and the solutions became increasingly turbid (FIG. 5, left images). In an attempt to mitigate the issue, polysorbate 80 was used. Polysorbate 80 was able to prevent air bubble entrapment (FIG. 5, right images). Therefore, polysorbate 80 was added at a concentration of 0.05% (w/v) to the high concentration formulation of PEG-FGF-21.

Oxidation is a critical quality attribute of PEG-FGF-21 and oxidation of methionine-169 near the C-terminus abolishes receptor binding and thus activity of the molecule. Metal catalyzed oxidation is one of the mechanisms by which protein can be oxidized. Trace concentrations of metals can be present in protein formulation due to carry over from cell culture, contact with stainless steel vessels, impurities in excipients, formation process of pre-fillable syringes, etc.

Figure 2A:
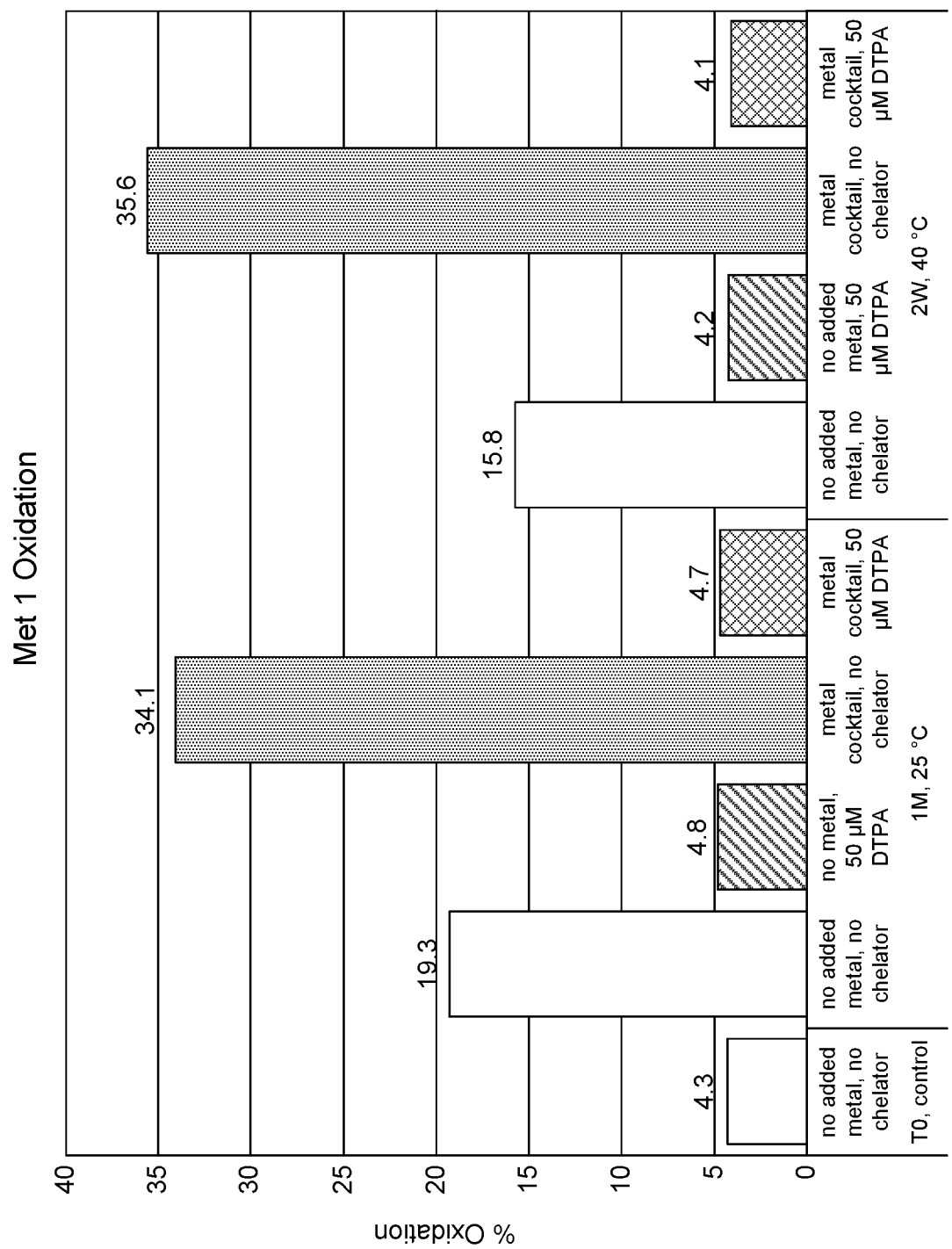
FIGS. 2A and 2B show metal catalyzed oxidation of PEG-FGF-21 polypeptide at methionine 1 (FIG. 2A) and methionine 169 (FIG. 2B) in the presence and absence of 50 µM DTPA (also known as pentetic acid).
Figure 2B:
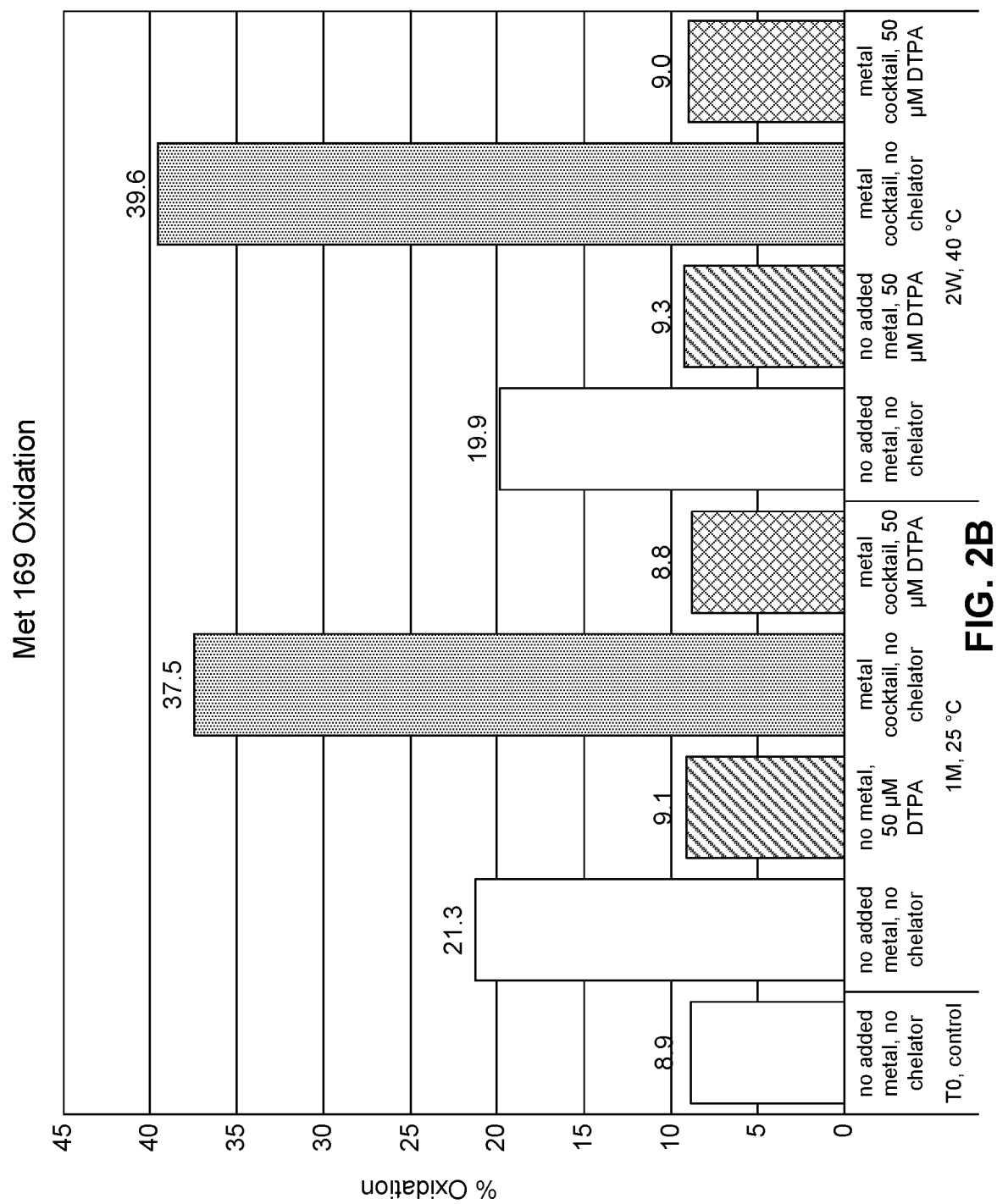

To test if PEG-FGF-21 was sensitive to metal catalyzed oxidation, samples with and without addition of a metal cocktail (250 ppm Fe, 10 ppm Cu, 15 ppm Cr, 15 ppm Ni, 10 ppm Mo) in the presence or absence of 0.05 mM pentetic acid (diethylenetriaminepentaacetic acid, DTPA) were incubated for one month at 25° C. and for two weeks at 40° C., respectively, and oxidation levels of methionine 1 and methionine 169 were determined by tryptic peptide mapping (FIGS. 2A and 2B).

In the absence of pentetic acid (DTPA), significant oxidation of both methionine residues was observed even in samples without added metal while in samples spiked with a metal cocktail oxidation levels were even higher. In samples with 50 μM pentetic acid, no increase in oxidation levels were observed for either methionine. This suggests that PEG-FGF-21 is sensitive to metal catalyzed oxidation and that there are already trace levels of metals present in the formulation. Pentetic acid effectively chelated the metals present in the formulation as well as additional metals spiked into the formulation and prevented metal catalyzed oxidation of methionines 1 and 169. Therefore, 50 μM pentetic acid was added to the high concentration formulation of PEG-FGF-21.

Figure 3A:
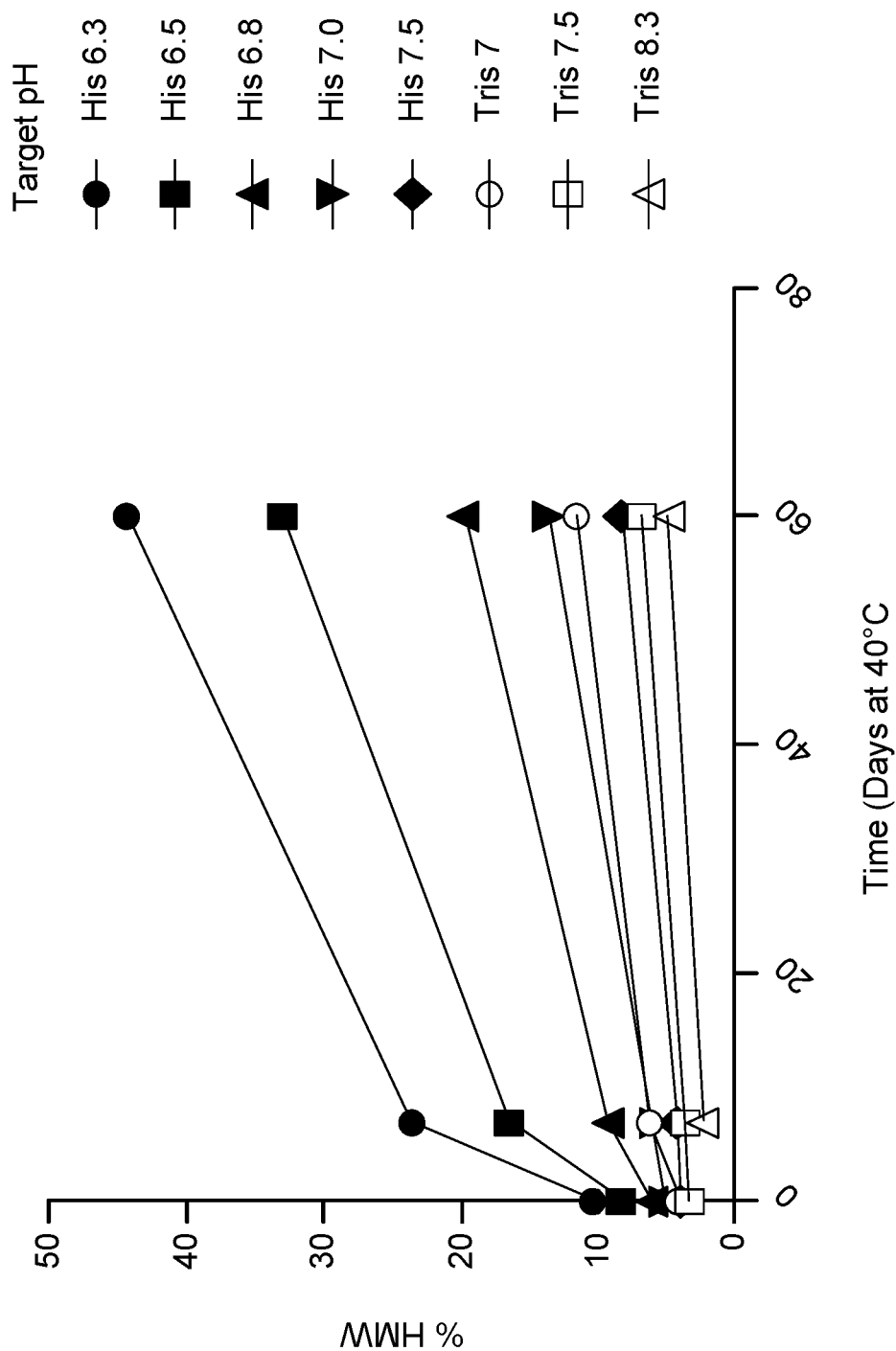
FIGS. 3A and 3B show the effect of pH on PEG-FGF-21 aggregation.
Figure 3B:
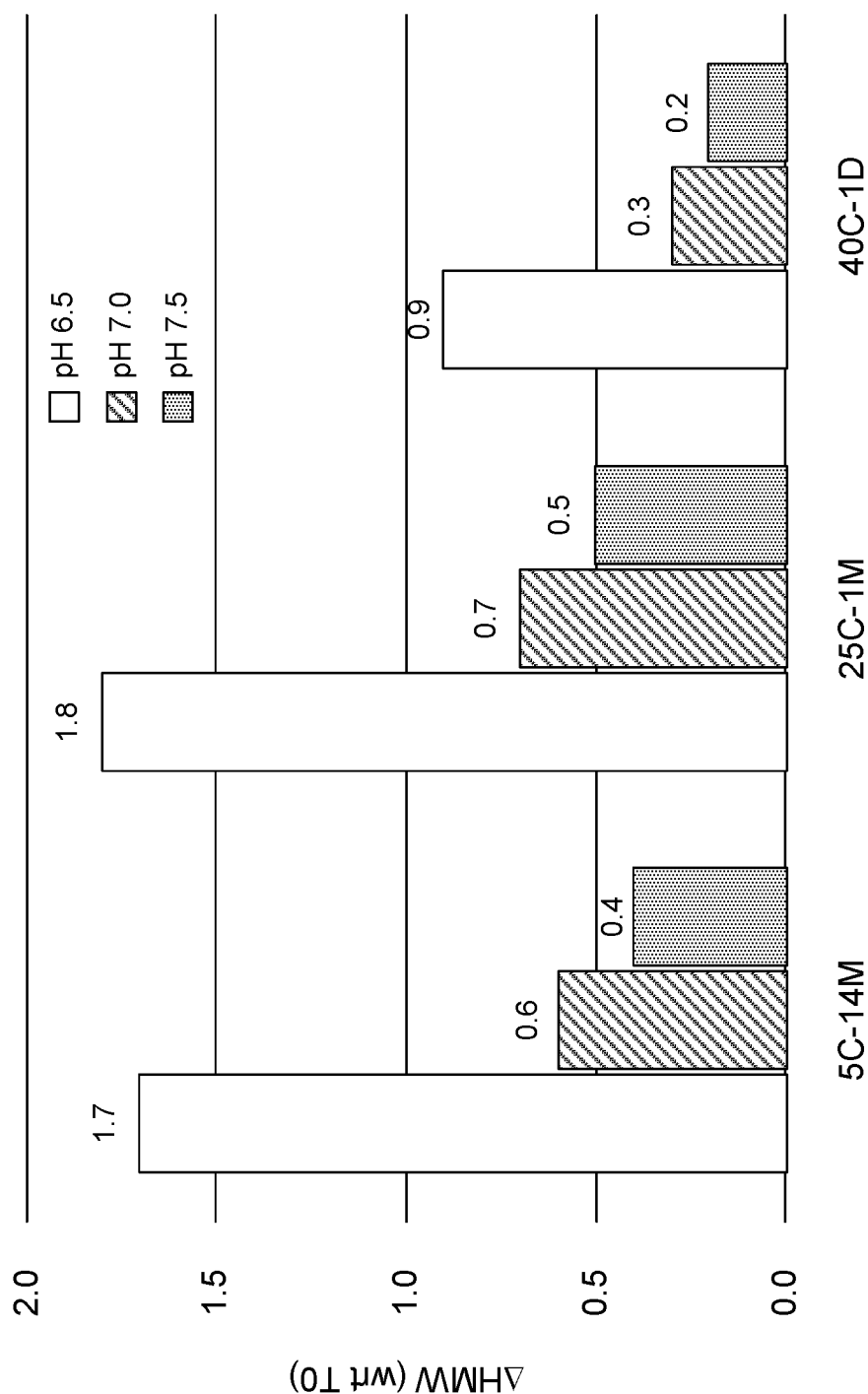
Figure 4A:
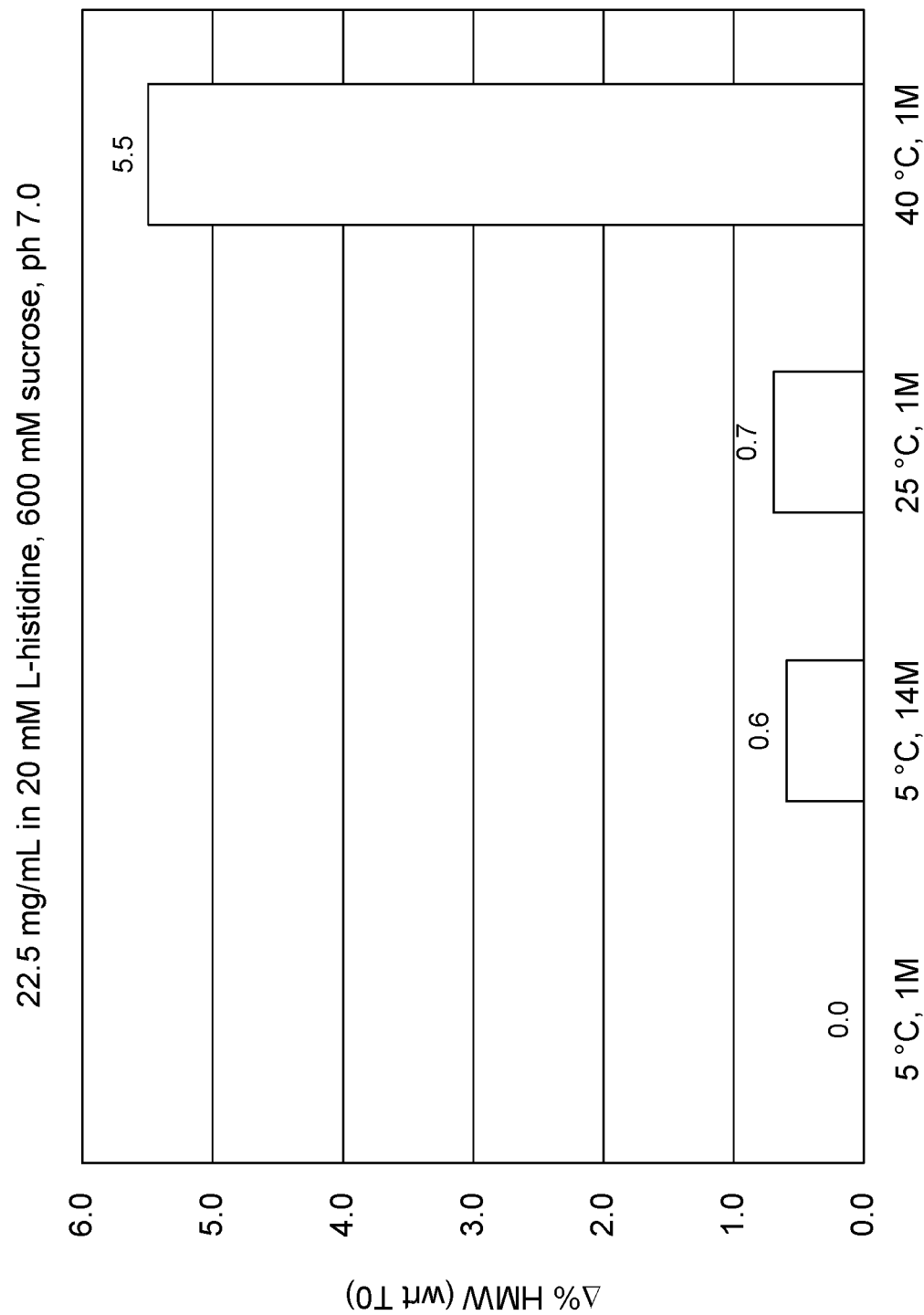
FIGS. 4A and 4B show aggregation of PEG-FGF-21 as a function of formulation composition.
Figure 4B:
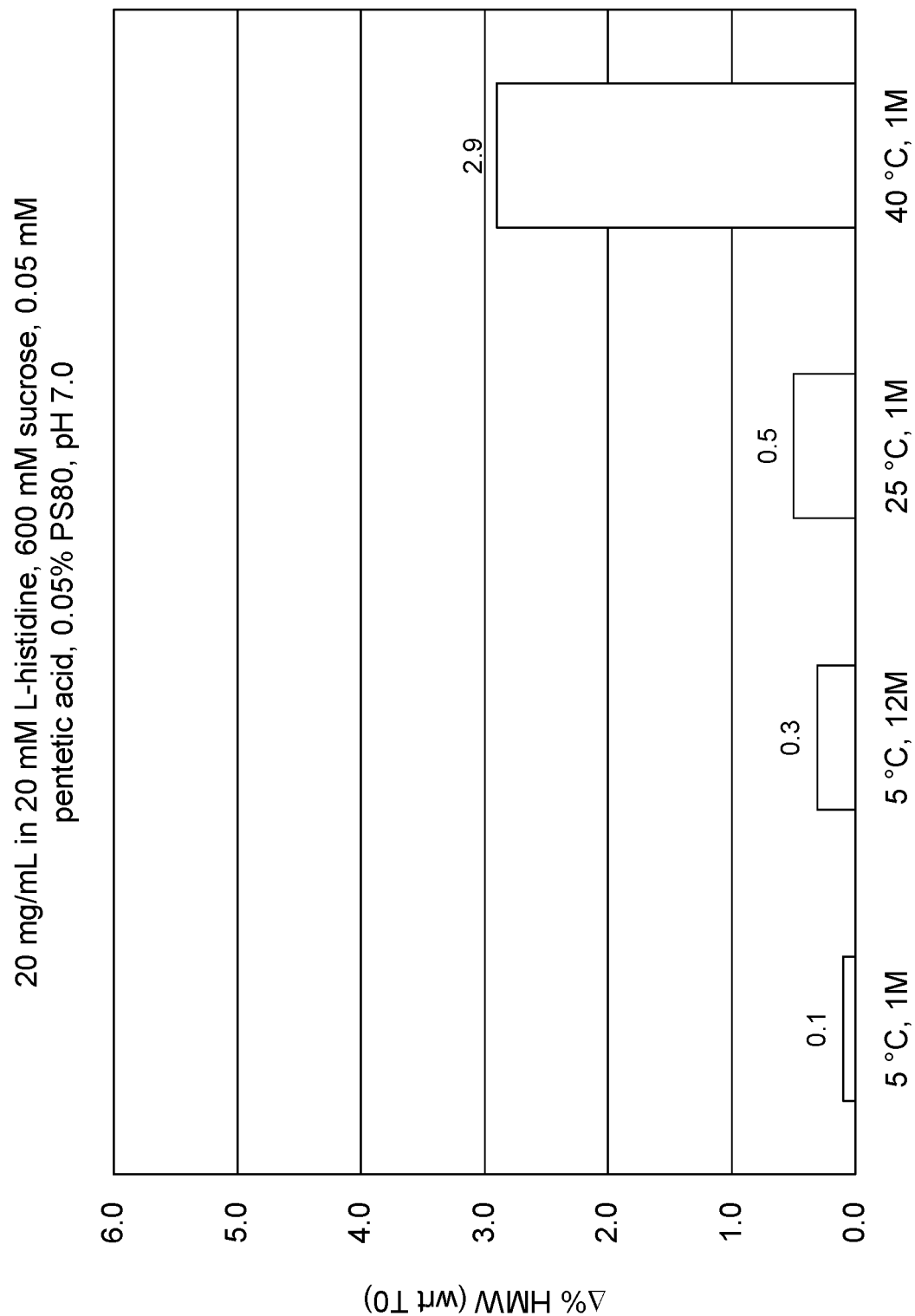

To optimize the pH for the higher concentration formulation, we reviewed aggregation data of PEG-FGF-21 collected between pH 6.3 and 8.5 showing that aggregation rates rapidly increased below pH 6.8 (FIGS. 3A and 3B). Therefore, we increased the target pH for the high concentration formulation from pH 7.0 to pH 7.1

To compare the new high concentration formulation to the previous formulation, PEG-FGF-21 at 20 mg/mL in 20 mM L-histidine, 600 mM sucrose, 0.05 mM pentetic acid, 0.05% (w/v) polysorbate 80, pH 7.0 (prior to pH optimization) was placed on stability and compared to PEG-FGF-21 at 22.5 mg/mL in 20 mM L-histidine, 600 mM sucrose, pH 7.0.

As shown in FIGS. 4A and 4B, FIGS. 1A and 1B, addition of polysorbate 80 and pentetic acid to the PEG-FGF-21 formulation resulted in lower aggregation rates at all temperatures and less deamidation at 40° C.

Test Methods

Aggregation: Aggregation was tested by size exclusion high performance liquid chromatography on a commercially available system (e.g., Agilent Technologies 1100 Series HPLC system with PDA detector or Waters Alliance e2695 Series HPLC with PDA detector) fitted with a commercially available analytical column (Tosoh TSK gel G3000SWXL, 7.8×300 mm, P/N: 08541). A mobile phase of 95% phosphate buffered saline (PBS) and 5% ethanol at a flow rate of 0.8 ml/min was used to separate high molecular weight species from protein monomer. Samples were diluted to a protein concentration of 0.5 mg/mL with PBS and 0.01 mg (0.02 mL) were injected for each experiment. The amount of aggregate was determined by dividing the area of high molecular weight peaks by the total area of all observed peaks using instrument software.

Deamidation: Deamidation was tested by anion exchange high performance liquid chromatography on a commercially available system (e.g., Agilent Technologies 1100 Series HPLC system with PDA detector or Waters Alliance e2695 Series HPLC with PDA detector) fitted with a commercially available analytical column (Agilent Bio WAX, non-porous, 5 μm column, 4.6×250 mm, P/N: 5190-2487). Mobile phase A consisted of 20 mM Tris, pH 8.2 and mobile phase B consisted of 20 mM Tris, 500 mM Sodium Chloride, pH 8.2. A linear gradient from 2% B to 67% B over 20 minutes at a flow rate of 1.0 ml/min was used to separate charged protein variants. Samples were diluted to a protein concentration of 1 mg/mL with mobile phase A and 0.075 mg (0.075 mL) were injected for each experiment. The amount of deamidation was determined by dividing the area of acidic variant peaks by the total area of all observed peaks using instrument software.

Oxidation: Oxidation was tested by tryptic peptide mapping. After protein samples were digested with trypsin, resulting peptides were separated by reverse phase ultra-high performance liquid chromatography on a commercially available system (e.g., Waters Acquity UPLC) fitted with a commercially available analytical column (Waters Acquity C18 BEH peptide RP UPLC column, 2.1×150 mm, 1.7-μm particle size, 130-Å pore size P/N: 186003556). Mobile phase A consisted of 0.2% trifluoroacetic acid (TFA) in water and mobile phase B consisted of 0.2% TFA in acetonitrile. A complex gradient from 10% B to 40% B over 27 minutes at a temperature of 60° C. and a flow rate of 0.3 ml/min was used to separate tryptic peptides. The amount of oxidation was determined by dividing the area of oxidized peptide peaks by the total area of oxidized and corresponding non-oxidized peaks using instrument software.

Particulate Formation and Air Bubble Formation: Visual Observation.

Concentration of PEG-FGF-21: The concentration of PEG-FGF-21 in the pharmaceutical formulation disclosed herein was measured by Slope Spectroscopy at 280 nm using an Extinction Coefficient of 0.87 (mL/(mg*cm)).

Determination of pH: pH was determined according to standard methods (USP<791>).

Concentration of excipients: The concentration of individual excipients in the pharmaceutical formulation disclosed herein (e.g., DTPA, PS80, Histidine, Sucrose) was determined/calculated to be the amount (weight, moles etc.) of the individual excipient added to the pharmaceutical formulation in the course of its manufacture per final volume unit of the finished pharmaceutical formulation. Alternatively, the concentration of excipients can be based on the actual amount of the individual excipient in the pharmaceutical formulation.

What is claimed is:

1. A pharmaceutical formulation comprising:
   (i) PEGylated FGF-21 polypeptide comprising the sequence set forth in SEQ ID NO: 2 (PEG-FGF-21) at a concentration of 20 mg/mL;
   (ii) histidine at a concentration of 20 mM;
   (iii) sucrose at a concentration of 600 mM;
   (iv) Polysorbate 80 at a concentration of 0.05% (w/v); and
   (v) Diethylenetriaminepentaacetic acid (DTPA) at a concentration of 50 µM;
   (vi) wherein the pH is 7.1,
   wherein DTPA functions as a structural stabilizer and the formulation exhibits:
   (a) a lower rate of PEGylated FGF-21 polypeptide deamidation when stored at 40° C. for about a month with respect to a reference formulation without DTPA;
   (b) a lower rate of high molecular weight (HMW) PEGylated FGF-21 polypeptide aggregation when stored at 40° C. for about a month with respect to the reference formulation without DTPA; or
   (c) both (a) and (b).

2. The pharmaceutical formulation of claim 1, wherein the formulation is formulated for subcutaneous administration.

3. A method of treating a disease or condition associated with fibrosis in a subject in need thereof comprising administering to the subject an effective amount of the pharmaceutical formulation of claim 1.

4. The method of claim 3, wherein the disease or condition is nonalcoholic steatohepatitis (NASH).

* * * * *

UNITED STATES PATENT AND TRADEMARK OFFICE
CERTIFICATE OF CORRECTION

| | | |
|---|---|---|
| PATENT NO. | : 12,226,451 B2 | Page 1 of 1 |
| APPLICATION NO. | : 17/257530 | |
| DATED | : February 18, 2025 | |
| INVENTOR(S) | : Thomas Palm et al. | |

It is certified that error appears in the above-identified patent and that said Letters Patent is hereby corrected as shown below:

On the Title Page

Column 2, Item (57), under "Abstract", Line 4, delete "DPTA." and insert -- DTPA. --, therefor.

Signed and Sealed this
Twenty-second Day of April, 2025

Coke Morgan Stewart
*Acting Director of the United States Patent and Trademark Office*